(12) United States Patent
Van Vranken et al.

(10) Patent No.: US 11,174,267 B2
(45) Date of Patent: Nov. 16, 2021

(54) SPIROINDOLINONES AND THERAPEUTIC USES THEREOF

(71) Applicant: The Regents of the University of California, Oakland, CA (US)

(72) Inventors: David Lee Van Vranken, Irvine, CA (US); Haoping Liu, Irvine, CA (US); Ilandari Dewage Udara Anulal Premachandra, Los Angeles, CA (US); Fuqiang Wang, Irvine, CA (US); Chengtian Shen, Irvine, CA (US); Kevin Andre Scott, Vista, CA (US); Shelley Ren-An Lane, Huntington Beach, CA (US); Aaron David Mood, Fullerton, CA (US); Stanley Chungsing Hiew, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 275 days.

(21) Appl. No.: 15/735,873

(22) PCT Filed: Jun. 13, 2016

(86) PCT No.: PCT/US2016/037251
§ 371 (c)(1),
(2) Date: Dec. 12, 2017

(87) PCT Pub. No.: WO2016/201440
PCT Pub. Date: Dec. 15, 2016

(65) Prior Publication Data
US 2020/0140449 A1    May 7, 2020

Related U.S. Application Data

(60) Provisional application No. 62/175,202, filed on Jun. 12, 2015.

(51) Int. Cl.
| C07D 487/20 | (2006.01) |
| A61P 31/10 | (2006.01) |
| C07D 487/14 | (2006.01) |
| A61K 45/06 | (2006.01) |

(52) U.S. Cl.
CPC ............ *C07D 487/14* (2013.01); *A61P 31/10* (2018.01); *C07D 487/20* (2013.01); *A61K 45/06* (2013.01)

(58) Field of Classification Search
CPC ................................ C07D 487/20; A61P 31/10
See application file for complete search history.

(56) References Cited

U.S. PATENT DOCUMENTS

| 6,358,750 B1 | 3/2002 | Fokas et al. |
| 8,759,400 B2 | 6/2014 | Georgopapadakou et al. |
| 2002/0143035 A1 | 10/2002 | Launay et al. |
| 2009/0275560 A1 | 11/2009 | Ang et al. |
| 2014/0094494 A1 | 4/2014 | Klein et al. |

FOREIGN PATENT DOCUMENTS

| EP | 421441 A2 | 4/1991 |
| EP | 1853251 B1 | 4/2013 |
| WO | 2007072179 A2 | 6/2007 |
| WO | 2016201440 | 12/2016 |

OTHER PUBLICATIONS

PubChem CID 4975280, National Center for Biotechnology Information. PubChem Database. CID=4975280, https://pubchem.ncbi.nlm.nih.gov/compound/4975280 (accessed on May 12, 2020), create date Sep. 17, 2005. (Year: 2005).*
Chemical Abstracts Registry No. 1014087-64-9, indexed in the Registry file on Apr. 13, 2008. (Year: 2008).*
Azizian et al., Letters in Organic Chemistry, 2006, 3, pp. 887-890. (Year: 2006).*
PubChem CID 6584729 {National Center for Biotechnology Information. "PubChem Compound Summary for CID 6584729" PubChem, https://pubchem.ncbi.nlm.nih.gov/compound/6584729. Accessed Sep. 11, 2020, create date May 23, 2006. (Year: 2006).*
Berge et al., Journal of Pharmaceutical Sciences, Jan. 1977, 66(1), pp. 1-19. (Year: 1977).*
International Preliminary Report on Patentability for International Application PCT/US2016/037251, Report issued Dec. 12, 2017, dated Dec. 21, 2017, 8 Pgs.
International Search Report and Written Opinion for International Application No. PCT/US2016/037251, Search completed Aug. 22, 2016, dated Sep. 13, 2016, 10 Pgs.

(Continued)

*Primary Examiner* — Laura L Stockton
(74) *Attorney, Agent, or Firm* — KPPB LLP

(57) ABSTRACT

Small molecules comprised of spiroindolinone analogues are provided. Some spiroindolinones are provided with a particular relative stereochemistry in which the indolone carbonyl and all three hydrogens are on the same face of the central pyrrolidine ring. A stereoselective method of synthesis is provided for making some of the spiroindolinones described above. Formulations and medicaments are also provided that are directed to the treatment of disease, such as, for example, fungal infections. Therapeutics are also provided containing a therapeutically effective dose of one or more small molecule compounds, present either as pharmaceutically effective salt or in pure form, including, but not limited to, formulations for oral, intravenous, or intramuscular administration.

21 Claims, 16 Drawing Sheets
Specification includes a Sequence Listing.

(56) References Cited

OTHER PUBLICATIONS

"Summary of Broad Institute MLPCN Reversing Antifungal Drug Resistance Project", National Center for Biotechnology Information, PubChem BioAssay Database, Oct. 22, 2009; AID=2007, Source=Broad Institute, https://pubchem.ncbi.nlm.nih.gov/assay/assay.cgi?aid=2007, 14 pgs.

"Flourescence Cell-Based Secondary Assay to Identify Inhibitors of Resistance C. albicans Growth in the Presence of Fluconazole", National Center for Biotechnology Information, PubChem BioAssay Database, Feb. 25, 2010; AID=2423, Source=Broad Institute, https://pubchem.ncbi.nlm.nih.gov/assay/assay.cgi?aid=2423, 15 pgs.

"Molinspiration property calculation service", http://www.molinspiration.com/cgi-bin/properties, Molinspiration Cheminformatics, 2002.

"FDA Drug Safety Communication:Use of long-term, high-dose Diflucan (fluconazole) during pregnancy may be associated with birth defects in infants", U.S. Department of Health and Human Services, Food & Drug Administration, Aug. 3, 2011, https://www.fda.gov/Drugs/DrugSafety/ucm266030.htm, 4 pgs.

Abbott et al., "Angioedema after fluconazole", The Lancet, Sep. 7, 1991, vol. 338, p. 633.

Abdelmegeed et al., "Cyclooxygenase Inhibitors Reduce biofilm formation and Yeast-Hypha Conversion of Fluconazole Resistant Candida albicans", Journal of Microbiology, Sep. 2013, vol. 51, pp. 598-604.

Ahmadi et al., "Invasive candidiasis in intensive care unit; consensus statement from an Iranian panel of experts, Jun. 2013", Journal of the Royal Society of Medicine Open, Mar. 3, 2014, vol. 5, No. 3, pp. 1-10.

Almansour et al., "A Facile Ionic Liquid Promoted synthesis, Cholinesterase Inhibitory Activity and Molecular Modeling Study of Novel Highly Functionalized Spiropyrrolidines", Molecules, 2015, vol. 20, pp. 2296-2309.

Amornraksa et al, "XY-ZH Systems as potential 1,3-dipoles. Part 8. Pyrrolidines and AΔ5-pyrrolines (3,7-diazabicyclo[3.3.0]octenes) from the reaction of imines of α-amino acids and their esters with cyclic dipolarophiles", Mechanism of racemisation of α-amino acids and their esters in the presence of aldehydes, Journal of the Chemical Society Perkin Transactions 1, Jan. 1, 1987, pp. 2285-2296.

Anaissie et al., "Management of invasive candidal infections: results of a prospective, randomized, multicenter study of fluconazole versus amphotericin B and review of the literature", Clin. Infect. Dis., Nov. 1996, vol. 23, p. 964 972.

Ardill et al., "X=Y-ZH compounds as potential 1,3-Dipoles. The iminium ion route to azomethine ylides. Background and reaction of amines with bifunctional ketones", Tetrahedron, 1990, vol. 46, pp. 6433-6448.

Arumugam et al., "Synthesis and antimicrobial activity of highly functionalised novel β-lactam grafted spiropyrrolidines and pyrrolizidines", European Journal of Medicinal Chemistry, Feb. 2011, vol. 46, Issue 2, pp. 600-607.

Azizian et al., "One-pot highly diastereo-selective synthesis of new 2-substituted 8-(sprio-3'- indolino-2'-one)-pyrrolo[3,4-a]-pyrrolizine-1,3-diones mediated by azomethine ylide induced by microwave irradiation", Synth. Commun. 2001, vol. 31, pp. 2727-2733.

Barchiesi et al., "In vitro activities of terbinafine in combination with fluconazole and itraconazole against isolates of *Candida albicans* with reduced susceptibility to azoles", Antimicrobial Agents and Chemotherapy, Aug. 1997, vol. 41, pp. 1812-1814.

Binanzer et al., "Catalytic Kinetic Resolution of Cyclic Secondary Amines", Journal of the American Chemical Society, Nov. 14, 2011, vol. 133, No. 49, pp. 19698-19701.

Chen et al., "Synthesis and Antitumor Activity Evaluation of Regioselective Spiro [pyrrolidine-2,3'-oxindole] Compounds", Heterocyclic Communications, Oct. 1, 2009, vol. 15, pp. 355-360.

Coulter et al., "Chiral induction in cycloaddition reactions of azomethine ylides derived from secondary α-amino acids by the decarboxylative route", Tetrahedron Letters, Jul. 1991, vol. 32, Issue 39, pp. 5417-5420.

Craig et al., "Desensitization for fluconazole hypersensitivity", J. Allergy Clin. Immunol., Oct. 1996, vol. 98, No. 4, pp. 845-846.

Cruz et al., "Calcineurin is essential for survival during membrane stress in Candida albicans", EMBO Journal, Feb. 15, 2002, vol. 21, No. 4, pp. 546-559.

Cuenca-Estrella, "Combinations of antifungal agents in therapy—what value are they?", Journal of Antimicrobial Chemotherapy, Sep. 16, 2004, vol. 54, pp. 854-869.

Czaika et al., "Detection of azole susceptibility patterns in clinical yeast strains isolated from 1998 to 2008", New Microbiol., Sep. 10, 2014, vol. 37, pp. 465-494.

Da Silva et al., "Synergistic Effect of the Flavonoid Catechin, quercetin, or Epigallocatechin Gallate with Fluconazole Induces Apoptosis in Candida tropicalis Resistant to Fluconazole", Antimicrobial Agents and Chemotherapy, Mar. 2014, vol. 58, No. 3, pp. 1468-1478.

Da Silva et al., "Synergistic Effects of Amiodarone and Fluconazole on Candida Tropicalis Resistant to Fluconazolei", Antimicrobial Agents and Chemotherapy, Apr. 2013, vol. 57, No. 4, pp. 1691-1700.

Denardi et al., "Synergistic effects of tacrolimus and azole antifungal compounds in fluconazole-susceptible and fluconazole-resistant Candida glabrata isolates", Brazilian Journal of Microbiology, Mar. 31, 2015, vol. 46, No. 1, pp. 125-129.

Denardi et al., "Antifungal activities of diphenyl diselenide alone and in combination with fluconazole or amphotericin B against *Candida glabrata*", Mycopathologia, Jun. 23, 2013, vol. 176, Issue 1-2, pp. 165-169.

Dondas et al., "1,3-Dipolar cycloaddition of stabilised and non-stabilised azomethine ylides derived from uracil polyoxin C (UPoC): access to nikkomycin analogues", Tetrahedron, Feb. 12, 2004, vol. 60, Issue 15, pp. 3473-3485.

Elboray et al., "Skeletal diversity via Pd(0) catalyzed three-component cascades of allene and halides or triflates with protected hydroxylamines and formamide", Tetrahedron, Feb. 4, 2012, vol. 68. No. 14, pp. 3103-3111.

Felluga et al., "Application of 1,3-Azomethine Ylides Derived from α-Dicarbonyl Compounds and L-Proline to the Synthesis of Pyrrolizidines", Journal of Heterocyclic Chemistry, May 2010, vol. 47, No. 3, pp. 664-670.

Filippone et al., "On the Mechanism of the Thermal Retrocycloaddition of Pyrrolidinofullerenes (Retro-Prato Reaction)", Chemistry, Apr. 25, 2008, vol. 14, Issue 17, pp. 5198-5206.

Flowers et al., "Gain-of-function mutations in UPC2 are a frequent cause of ERG11 upregulation in azole-resistant clinical isolates of Candida albicans", Eukaryotic Cell, Oct. 2012, vol. 11, No. 10, pp. 1289-1299.

Fokas et al., "Solution Phase Synthesis of a Spiro[pyrrolidine-2,3'-oxindole] Library via a Three-Component 1,3-Dipolar Cycloaddition Reaction", Tetrahedron Letters, Jan. 16, 1998, vol. 39, No. 16, pp. 2235-2238.

Ganguly et al, "Solution-and solid-phase synthesis of enantiomerically pure spiro oxindoles", Tetrahedron Letters, Sep. 19, 2002, vol. 43, Issue 49, pp. 8981-8983.

Gao et al., "Synergistic effect of doxycycline and fluconazole against *Candida albicans* biofilms and the impact of calcium channel blockers", FEMS Yeast Research, May 2, 2013, vol. 13, pp. 453-462.

Grigg et al., "1,3-Dipolar Cycloaddition reactions of Imines of a-amino-acid Esters: X-Ray Crystal and Molecular Structure of Methyl 4-(2-Furyl)2-7-diphenyl-6,8-dioxo-3,7-diazabicyclo[3,3,0]octane-2=carboxylate", J. chem. Soc., Chem. Commun., Jan. 1, 1978, pp. 109-111.

Grigg et al., "X=y-zh systems as potential 1,3-dipoles : Part 22.1 cycloaddition reactions of pyridoxal imines, relevance to a-amino acid racemases and transaminases", Tetrahedron, Sep. 1988, vol. 44, Issue 23, pp. 7283-7292.

(56) References Cited

OTHER PUBLICATIONS

Guo et al., "In vitro synergy of pseudolaric acid B and fluconazole against clinical isolates of *Candida albicans*", Mycoses, Jun. 16, 2011, vol. 54, No. 5, pp. e400-e406.
Perez et al., "Discovery of Novel Protease Activated Receptors 1 Antagonists with Potent Antithrombotic Activity in Vivo", Journal of Medicinal Chemistry, Apr. 30, 2009, vol. 52, No. 19, pp. 5826-5836.
Pfaller et al., "In Vitro Activities of 5-Fluorocytosine against 8, 803 Clinical Isolates of *Candida* spp.: Global Assessment of Primary Resistance Using National Committee for Clinical Laboratory Standards Susceptibility Testing Methods", Antimicrobial Agents and Chemotherapy, Nov. 2002, vol. 46, No. 11, pp. 3518-3521.
Phillips et al., "Multicenter randomized trial of fluconazole versus amphotericin B for treatment of candidemia in non-neutropenic patients", Canadian Candidemia Study Group. Eur. J. Clin. Microbiol. Infect. Dis., May 1997, vol. 16, pp. 337-345.
Ponnala et al., "One pot synthesis of novel dispiro[oxindole-thiazolidinedione/thioxo-thiazolidinone/dihydro pyrazolone]-pyrrolidines via 1, 3-dipolar cycloaddition reaction of azomethine ylides", Journal of Heterocyclic Chemistry, Nov./Dec. 2006, vol. 43, Issue 6, pp. 1635-1640.
Powers et al., "Automated parallel synthesis of chalcone-based screening libraries", Tetrahedron, Apr. 16, 1998, vol. 54, Issue 16, pp. 4085-4096.
Premachandra et al., "Potent synergy between Spirocyclic Pyrrolidinoindolines and Fluconazole against Candida albicans", ChemMedChem, Aug. 12, 2015, vol. 10, Issue 10, pp. 1672-1686.
Proudfoot, "The evolution of synthetic oral drug properties", Bioorganic & Medicinal Chemistry Letters, Jan. 12, 2005, vol. 15, pp. 1087-1090.
Purushothaman et al., "Regioselective synthesis of spiropyrrolidine/spiropyrrolizidine/spirothiazolidine-grafted macrocycles through 1,3-dipolar cycloaddition methodology", Tetrahedron, Sep. 24, 2013, vol. 69, Issue 46, pp. 9742-9750.
Quan et al., "Potent In Vitro of Fluconazole and Berberine Chloride Against Clinical Isolates of Candida albicans Resistant to Fluconazole", Antimicrobial Agents and Chemotherapy, Mar. 2006, vol. 50, No. 3, pp. 1096-1099.
Rao et al., "An expedient diastereoselective synthesis of pyrrolidinyl spirooxindoles fused to sugar lactone via [3+2] cycloaddition of azomethine ylides", Feb. 15, 2012, vol. 53, Issue 7, pp. 854-858.
Rehn et al., "The three-component reaction between isatin, α-amino acids, and dipolarophiles", Eur. J. Org. Chem., Jan. 9, 2004, 413-418.
Revankar et al., "Candidiasis (Invasive)", Merck Manual, 2014, http://www.merckmanuals.com/professional/infectious-diseases/fungi/candidiasis-invasive, 5 pgs.
Revathy et al., "An efficient green chemistry protocol for the synthesis of novel spiropyrrolizidine compounds", RSC Advances, 2014, pp. 279-285.
Rex et al., "A randomized and blinded multicenter trial of high-dose fluconazole plus placebo versus fluconazole plus amphotericin B as therapy for candidemia and its consequences in nonneutropenic subjects", Clin. Infect. Dis., May 2003, vol. 36, pp. 1221-1228.
Rex et al., "A randomized trial comparing fluconazole with amphotericin B for the treatment of candidemia in patients without neutropenia", Candidemia Study Group and the National Institute, New England Journal of Medicine, Nov. 17, 1994, vol. 331, pp. 1325-1330.
Robbins et al., "An Antifungal Combination Matrix Identifies a Rich Pool of Adjuvant Molecules that Enhance Drug Activity Against Diverse Fungal Pathogens", Cell Reports, Nov. 17, 2015, vol. 13, pp. 1481-1492.
Rodriguez et al., "In vitro interaction of micafungin and fluconazole against Candida", Journal of Antimicrobial Chemotherapy, Aug. 2007, pp. 188-190, advance access publication May 24, 2007.
Saad et al., "Anticandidal activity of the essential oils of *Thymus maroccannus* and *Thymus broussonitii* and their synergism with amphotericin B and fluconazol", Phytomedicine, Nov. 2010, vol. 17, pp. 1057-1060.
Salahi et al., "An efficient, one-pot, three-component procedure for the synthesis of chiral spirooxindolopyrrolizidines via catalytic highly enantioselective 1,3-dipolar cycloaddition", Tetrahedron Letters, Feb. 26, 2014, vol. 55, Issue 9, pp. 1515-1518.
Sandmeyer, "Über Isonitrosoacetanilide und deren Kondensation zu Isatinen", Helvetica Chim. Acta, Nov. 10, 1919, vol. 2, pp. 234-242.
Sarrafi et al., "Synthesis of functionalized pyrrolizidines/pyrrolidines incorporating a spirooxindole motif through [3+2] cycloaddition", Synthesis, May 20, 2013, vol. 45, pp. 2294-2304.
Scalarone et al., "In vitro comparative evaluations of the postantifungal effect: synergistic interaction between flucytosine and fluconazole against *Candida albicans*", Mycoses, Sep. 1991, vol. 34, pp. 405-410.
Sekine et al., "In vitro and in vivo effects on *Candida* spp. of flucytosine combined with fluconazole", Chemotherapy, Feb. 1994, vol. 42, pp. 164-171, English Abstract Provided.
Serpa et al., "In vitro antifungal activity of the flavonoid baicalein against *Candida* species", Journal of Medical Microbiology, Aug. 2012, vol. 61, No. 12, pp. 1704-1708.
Slavin et al., "Efficacy and safety of fluconazole prophylaxis for fungal infections after marrow transplantation: a prospective, randomized, double-blind study", Journal of Infectious Disease, Jan. 20, 1995, vol. 171, pp. 1545-1552.
Spitzer et al., "Cross-species discovery of syncretic drug combinations that potentiate the antifungal fluconazole", Molecular Systems Biology, Jun. 21, 2011, vol. 7, Article 499, pp. 1-14.
Su et al., "Acute hepatitis and rash to fluconazole", Allergy, Jun. 3, 2003, vol. 58, pp. 1215-1216.
Sun et al., "In Vitro Interactions between Tacrolimus and Azoles against Candida albicans Determined by Different Methods", Antimicrobial Agents and Chemotherapy, Feb. 2008, vol. 52, No. 2, pp. 409-417.
Taghizadeh et al., "Synthesis of new enantiomerically pure spirooxindolopyrrolizidines via a three-component asymmetric 1,3-dipolar cycloaddition reaction of azomethine ylides derived from isatin", Tetrahedron Letters, Jul. 20, 2012, vol. 53, Issue 38, pp. 5148-5150.
Te Dorsthorst et al., "In Vitro Interaction of Flucytosine Combined with amphotericin B or Fluconazole Against Thirty-Five Yeast Isolates Determined by both the Fractional Inhibitory Concentration Index and the Response Surface Approach", Antimicrobial Agents and Chemotherapy, Sep. 2002, vol. 46, No. 9, pp. 2982-2989.
Tobudic et al., "Azole-resistant *Candida* spp.—emerging pathogens?", Mycoses, 2012, vol. 55, pp. 24-32.
Tsuge et al., "Simple Generation of Ester-Stabilized Azomethine Ylides from 2-Amino Esters and Carbonyl Compounds. Stereochemistry of Their Cycloadditions", Bull. Chem. Soc. Jpn., Nov. 1987, vol. 60, pp. 4067-4078.
Tsuge et al., "Stable Configuration of Ester-Stabilized Azomethine Ylides. Stabilization of anti-Form by 1,5-Dipolar Interaction and of syn-Form by Hudrogen Bonding", Chemistry Letters, 1986, pp. 1271-1274.
Tsuge et al., "Stereospecific Reversible Cycloadditon Reactions of a Biperfunctional Compouond, 1,3,6-Triphenylimidazo[1,2-c]thiaivzole", Chemistry Letters, The Chemical Society of Japan, 1983, pp. 85-88.
Warrilow et al., "Azole affinity of sterol 14α-demethylase (CYP51) enzymes from Candida albicans and*Homo sapiens*", Antimicrob. Agents Chemother., Mar. 2013, vol. 57, pp. 1352-1360.
Wei et al., "In vitro synergism between berberine and miconazole against planktonic and biofilm Candida cultures", Archives of Oral Biology, Jun. 1, 2011, vol. 56, Issue 6, pp. 565-572.
Xu et al., "Proteomic analysis reveals a synergistic mechanism of fluconazole and berberine against fluconazole-resistant *Candida albicans*', endogenous ROS augmentation", Journal of Proteome Research, Jun. 9, 2009, vol. 8, pp. 5296-5304.
Youngsaye et al., "Disrupting fluconazole resistance in Candida albicans clinical isolates with tetracyclic indoles", Bioorg. Med. Chem. Lett., May 1, 2012, vol. 22, No. 9, pp. 3362-3365.

(56) References Cited

OTHER PUBLICATIONS

Youngsaye et al., "ML212: A small-molecule probe for investigating fluconazole resistance mechanisms in Candida albicans", Beilstein Journal of Organic Chemistry, Jul. 26, 2013, vol. 9, pp. 1501-1507.
Youngsaye et al., "Piperazinyl quinolines as chemosensitizers to increase fluconazole susceptibility of Candida albicans clinical isolates", Bioorg. Med. Chem. Lett., Sep. 15, 2011, vol. 21, pp. 5502-5505.
Zhang et al., "Antifungal activity of geldanamycin alone or in combination with fluconazole against *Candida* species", Mycopathologia, Apr. 2013, vol. 175, pp. 273-279, doi: 10.1007/s11046-012-9612-1, published online Jan. 23, 2013.
Guo et al., "The study of combination of fluconazole with nystatin against isolates of vaginal Candida albicans in vitro", The Chinese Journal of Dermatovenereology, May 2007, vol. 21, pp. 277-279, English Abstract provided.
Gussenhoven et al., "Stevens-Johnson syndrome after fluconazole", Lancet, Jul. 13, 1991, vol. 338, p. 120.
Huisgen et al., "Stereospecific conversion of cis-trans Isomeric Aziridines to Open-Chain Azomethine Ylides", J. Am. Chem. Soc, Feb. 14, 1967, vol. 89, pp. 1753-1755.
Iwazaki et al., "In vitro antifungal activity of the berberine and its synergism with fluconazole", Antonie van Leeuwenhoek, Feb. 2010, vol. 97, pp. 201-205, published online Nov. 2, 2009.
Jansen et al., "Chemogenomic profiling predicts antifungal synergies", Molecular Systems Biology, Dec. 22, 2009, vol. 5, Article 338, pp. 1-13.
Javidan et al., "Synthesis of new spiro-oxindolo-(pyrrolizidines/pyrrolidines) via cycloaddition reactions of azomethine ylides and dibenzylideneacetone", Monatschefte für Chemie—Chemical Monthly, Feb. 2014, vol. 145, Issue 2, pp. 341-348.
Kauffman, "Treatment of candidemia and invasive candidiasis in adults", UpToDate Sep. 23, 2014. Marr, K. A. and Thorner, A. R., eds., 27 pgs.
Khodavandi et al., "In vitro investigation of antifungal activity of allicin alone and in combination with azoles against *Candida* species", Mycopathologia, 2010, vol. 169, pp. 287-295, published online Nov. 19, 2009.
Kia et al., "Synthesis and discovery of novel piperidone-grafted mono- and bis-spirooxindole-hexahydropyrrolizines as potent cholinesterase inhibitors", Bioorganic & Medicinal Chemistry, Feb. 8, 2013, vol. 21, Issue 7, pp. 1696-1707.
Klochkova et al., "Synthesis of Spiropyrrolidines and Spiropyrrolizidines from Azomethine Ylides", Chemistry of Heterocyclic Compounds, Apr. 2014, vol. 50, No. 4, pp. 479-488.
Komatsu et al., "Design and Synthesis of an Enzyme Activity-Based Labeling Molecule with Fluorescence Spectral Change", Journal of the American Chemical Society, Aug. 7, 2006, vol. 128, No. 50, pp. 15946-15947.
Kumar et al., "A facile synthesis and antimycobacterial evaluation of novel spiro-pyrido-pyrrolizines and pyrrolidines", European Journal of Medicinal Chemistry, May 21, 2009, vol. 44, Issue 9, pp. 3821-3829.
Kumar et al., "Discovery of Antimycobacterial Spiro-piperidin-4-ones: An Atom Economic, Stereoselective Synthesis, and Biological Intervention", J. Med. Chem, May 12, 2008, vol. 51, pp. 5731-5735.
Lafleur et al., "Novel high-throughput screen against *Candida albicans* identifies antifungal potentiators and agents effective against biofilms", Journal of Antimicrobial Chemotherapy, Apr. 2011, vol. 66, pp. 820-826, advance access publication Jan. 28, 2011.
Laihia et al., "1H, 13C, 15N NMR, ESI mass spectral and single crystal X-ray structural characterization of three spiro[pyrrolidine-2,3'-oxindoles]", Journal of Molecular Structure, May 11, 2006, pp. 100-105.
Lamb et al., "The mutation T315A in Candida albicans sterol 14α-demethylase causes reduced enzyme activity and fluconazole resistance through reduced affinity", Journal of Biological Chemistry, Feb. 28, 1997, vol. 272, Issue 9, pp. 5682-5688.
Leeson et al., "The influence of drug-like concepts on decision-making in medicinal chemistry", Nature Reviews, Drug Discovery, Nov. 2007, vol. 6, pp. 881-890.
Li et al., "Strategy for discovering chemical inhibitors of human cyclophilin A: focused library design, virtual screening, chemical synthesis and bioassay", J. Comb. Chem., Apr. 13, 2006, vol. 8, pp. 326-337.
Li et al., "Combinatorial Synthesis of Functionalized Spirooxindole-Pyrrolidine/Pyrrolizidine/Pyrrolothiazole Derivatives via Three-Component 1,3-Dipolar Cycloaddition Reactions", ACS Combinatorial Science, Jul. 17, 2014, vol. 16, No. 9, pp. 506-512.
Lindquist et al., "Summary of Broad Institute MLPCN Reversing Antifungal Drug Resistance Project", PubChem Bioassay AID, 2007. Deposit Date: Oct. 22, 2009, 15 pgs.
Liu et al., "Structural optimization of berberine as a synergist to restore antifungal activity of Fluconazole against drug-resistant *Candida albicans*", ChemMedChem, Jan. 2014, vol. 9, No. 1, pp. 207-216.
Maheswari et al., "A facile regio- and stereoselective synthesis of novel dispirooxindolyl-[acridine-2',3-pyrrolidine/thiapyrrolizidine]-1'-ones via 1,3-dipolar cycloaddition of azomethine ylides", Tetrahedron Letters, Jan. 18, 2012, vol. 53, Issue 3, pp. 349-353.
Marcheetti et al., "Potent synergism of the combination of fluconazole and cyclosporine in Candida albicans", Antimicrobial Agents and Chemotherapy, Sep. 2000, vol. 44, No. 9, pp. 2373-2381.
Marvel et al., "Isatin", Org. Synthesis Coll, vol. 1, 1941, p. 327 (4 pgs.).
Maurya et al., "Antifungal activity of novel synthetic peptides by accumulation of reactive oxygen species (ROS) and disruption of cell wall against Candida albicans", Peptides, Jun. 13, 2011, vol. 32, No. 8, pp. 1732-1740.
Maurya et al., "Mechanism of action of novel synthetic dodecapeptides against *Candida albicans*", Biochim. Biophys. Acta, Jul. 20, 2013, vol. 1830, pp. 5193-5203.
Menezes et al., "In vitro synergism of simvastatin and fluconazole against *Candida* species", Revista do Institute de Medicina Tropical de Sal Paulo, Aug. 2012, vol. 4, pp. 197-199.
Messer et al., "Activities of micafungin against 315 invasive clinical isolates of fluconazole-resistant *Candida* spp", Journal of Clinical Microbiology, Feb. 2006, vol. 44, No. 2, pp. 324-326.
Monge et al., "Managing, profiling and analyzing a library of 2.6 million compounds gathered from 32 chemical providers", Molecular Diversity, Aug. 2006, vol. 10, pp. 389-403.
Murugan et al., "Synthesis of Novel Spiroheterocycles Through 1,3-Dipolar Cycloaddition of Azomethine Ylides with Triarylideneacetylacetone Through Decarboxylation", Synthetic Communications, Oct. 4, 2010, vol. 40, Issue 21, pp. 3135-3151.
Nascimento-Junior et al., "Microwave-assisted synthesis and structureactivity relationships of neuroactive pyrazolo[3,4-b]pyrrolo[3,4-d]pyridine derivatives", Bioorg. Med. Chem. Lett., 2010, vol. 20, pp. 74-77.
Neuhaus et al., "Anaphylactic reaction after oral fluconazole", BMJ, Jun. 1991, vol. 302, pp. 1341.
Nishi et al., "In vitro antifungal combination effects of micafungin with fluconazole, voriconazole, amphoterecin B, and flucytosine against clinical isolates of *Candida* species", J. Infect Chemotherapy, May 2009, vol. 15, pp. 123-124.
Oliveira et al., "In vitro antifungal activities of leaf extracts of *Lippia alba* (Verbenaceae) against clinically important yeast species", Revista da Sociedade Brasileira de Medicina Tropical, March-Apr. 2014, vol. 47, No. 2, pp. 247-250.
Overman et al., "Enantioselective synthesis of (-)-isiospermuline", Tetrahedron, May 29, 2003, vol. 59, pp. 6905-6919.
Padwa et al., "Intramolecular dipolar cycloaddition reactions with azomethine ylides", Journal of Organic Chemistry, 1979, vol. 44, pp. 255-261.
Pangborn et al., "Safe and Convenient Procedure for Solvent Purification", Organometallics, 1996, vol. 15, No. 5, pp. 1518-1520.
Pavlovskaya et al., "The regioselective synthesis of spirooxindolo pyrrolidines and pyrrolizidines via three-component reactions of acrylamides and aroylacrylic acids with isatins and a-amino acids", Beilstein Journal of Organic Chemistry, 2014, vol. 10, pp. 117-126.

(56) References Cited

OTHER PUBLICATIONS

Pavlovskaya et al., "Acryl- and methacrylamides. New dipolarophiles in reactions of [2+3]-dipolar cycloadditions to 2-oxindolazomethine ylides", Russian Journal of Organic Chemistry, Nov. 2013, vol. 49, No. 11, pp. 1564-1566.

Pavlovskaya et al., "Synthesis and chemical properties of new derivatives of 3a',6a'-Dihydro-2'H-Spiro-[Indole-3,1'-Pyrrolo[3,4-c]Pyrrole]-2,4',6'(1H,3'H,5'H)-Trione", Chemistry of Heterocyclic Compounds, Sep. 2013, vol. 49, No. 6, pp. 882-896 (Russian original vol. 49, No. 6, Jun. 2013).

* cited by examiner

Prior Art and/or enantiomers and/or enantiomers

FIG. 6

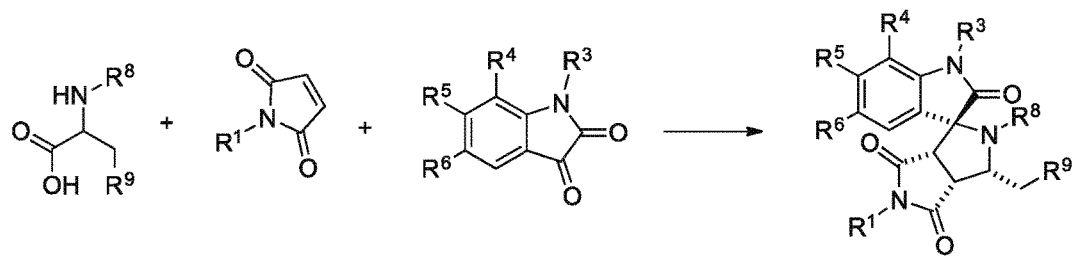

| Compound | R¹ | R⁸ | R⁹ | R⁶ | R⁵ | R⁴ | R³ | Yield |
|---|---|---|---|---|---|---|---|---|
| 1 | 4-fluorophenyl | H | Ph | H | Cl | CH$_3$ | H | 74% |
| 2 | Bn | H | Ph | H | H | H | H | 60% |
| 3 | Bn | H | 3-indolyl | H | H | H | H | 70% |
| 4 | Bn | H | (CH$_2$)$_3$NHBoc | H | H | H | H | 33% |
| 5 | Bn | H | Ph | MeO | H | H | H | 16% |
| 6 | Bn | H | Ph | H | H | H | Bn | 46% |
| 7 | Ph | H | Ph | H | H | H | Bn | 57% |
| 8 | Ph | H | Ph | H | Cl | CH$_3$ | H | 26% |
| 9 | Ph | CH$_2$CH$_2$N(Boc) | H | H | Cl | CH$_3$ | H | 60% |
| 10 | 4-fluorophenyl | CH$_2$CH$_2$N(Boc) | H | H | Cl | CH$_3$ | H | 49% |
| 11 | 3,5-bis(F$_3$C)phenyl | CH$_2$CH$_2$N(Boc) | H | H | Cl | CH$_3$ | H | 12% |
| 12 | Ph | CH$_2$CH$_2$N(Boc) | H | H | Cl | CH$_3$ | Bn | 82% |
| 13 | Bn | CH$_2$CH$_2$N(Boc) | H | H | H | H | Bn | 56% |
| 14 | Bn | CH$_2$CH$_2$N(Boc) | H | H | H | H | H | 53% |
| 15 | Ph | CH$_2$CH$_2$N(Boc) | H | H | H | H | Bn | 71% |
| 16 | Ph | CH$_2$CH$_2$N(Boc) | H | MeO | H | H | H | 27% |
| 17 | Bn | CH$_2$CH$_2$N(Boc) | H | MeO | H | H | H | 53% |
| 18 | Ph | CH$_2$CH$_2$N(Boc) | H | H | H | CH$_3$ | H | 60% |
| 19 | Ph | CH$_2$CH$_2$N(Boc) | H | H | CH$_3$ | CH$_3$ | H | 61% |
| 26 | cyclopropyl | H | Ph | H | Cl | CH$_3$ | H | 35% |
| 27 | cyclopentyl | H | Ph | H | Cl | CH$_3$ | H | 56% |
| 28 | cycloheptyl | H | Ph | H | Cl | CH$_3$ | H | 72% |
| 29 | 4-fluoro-2-methylphenyl | H | Ph | H | Cl | CH$_3$ | H | 16% |
| 30 | 5-methylisoxazol-3-yl | H | Ph | H | Cl | CH$_3$ | H | 16% |
| 31 | Ph | H | Ph | Cl | H | CH$_3$ | H | 59% |
| 32 | Ph | H | 4-bromophenyl | H | Cl | CH$_3$ | H | 28% |

(a) 1:1 TFA/CH$_2$Cl$_2$, 23 °C, 15 min, 90%, (b) 1.04 equiv methyl 10-chloro-10-oxodecanoate, 1.0 equiv Na$_2$CO$_3$, CH$_2$Cl$_2$, 23 °C, 30 min, 53%, (c) 1.3 equiv (S)-2-methoxy-2-phenylacetic acid, 2.1 equiv EDC, 3.5 equiv Et$_3$N, CH$_2$Cl$_2$, 23 °C, 20 min, 45%, (d)1.05 equiv 3-phenylpropanoyl chloride, 1.1 equiv Et$_3$N, CH$_2$Cl$_2$, 23 °C, 3 h, 64%, (e) 1.1 equiv (isocyanatomethyl)benzene, CH$_2$Cl$_2$, 23 °C, 4 h, 75%, (f) 1.1 equiv benzyl chloroformate, 2.1 equiv DIPEA, CH$_2$Cl$_2$, 0 - 23 °C, 2.5 h, 54%.

FIG. 10

| Compound | $R^1$ | $R^8$ | $R^9$ | $R^6$ | $R^5$ | $R^4$ | $R^3$ | $EC_{50}$ (μM) |
|---|---|---|---|---|---|---|---|---|
| 1 | 4-fluorophenyl | H | Ph | H | Cl | $CH_3$ | H | 0.011 |
| 2 | Bn | H | Ph | H | H | H | H | ~10 |
| 3 | Bn | H | 3-indolyl | H | H | H | H | ~10 |
| 4 | Bn | H | $(CH_2)_3$NHBoc | H | H | H | H | >100 |
| 5 | Bn | H | Ph | MeO | H | H | H | 3.936 |
| 6 | Bn | H | Ph | H | H | H | Bn | >10 |
| 7 | Ph | H | Ph | H | H | H | Bn | >100 |
| 8 | Ph | H | Ph | H | Cl | $CH_3$ | H | 0.001 |
| 9 | Ph | | $CH_2CH_2N(Boc)$ | H | Cl | $CH_3$ | H | 0.0056 |
| 10 | 4-fluorophenyl | | $CH_2CH_2N(Boc)$ | H | Cl | $CH_3$ | H | 0.037 |
| 11 | 3,5-bis($F_3C$)phenyl | | $CH_2CH_2N(Boc)$ | H | Cl | $CH_3$ | H | 0.0237 |
| 12 | Ph | | $CH_2CH_2N(Boc)$ | H | Cl | $CH_3$ | Bn | >100 |
| 13 | Bn | | $CH_2CH_2N(Boc)$ | H | H | H | Bn | 0.0318 |
| 14 | Bn | | $CH_2CH_2N(Boc)$ | H | H | H | H | >100 |
| 15 | Ph | | $CH_2CH_2N(Boc)$ | H | H | H | Bn | >100 |
| 16 | Ph | | $CH_2CH_2N(Boc)$ | MeO | H | H | H | >100 |
| 17 | Bn | | $CH_2CH_2N(Boc)$ | MeO | H | H | H | 230 |
| 18 | Ph | | $CH_2CH_2N(Boc)$ | H | H | $CH_3$ | H | 0.213 |
| 19 | Ph | | $CH_2CH_2N(Boc)$ | H | $CH_3$ | $CH_3$ | H | 0.0057 |
| 20 | Ph | | $CH_2CH_2NH$ | H | Cl | $CH_3$ | H | ~10 |
| 21 | Ph | | $CH_2CH_2N[CO(CH_2)_8CO_2Me$ | H | Cl | $CH_3$ | H | 0.0379 |
| 22 | Ph | | $CH_2CH_2N[COCH(OCH_3)C_6H_5]$ | H | Cl | $CH_3$ | H | 0.035 |
| 23 | Ph | | $CH_2CH_2N[CO(CH_2)_2Ph]$ | H | Cl | $CH_3$ | H | 0.0181 |
| 24 | Ph | | $CH_2CH_2N[CONHCH_2Ph]$ | H | Cl | $CH_3$ | H | 0.256 |
| 25 | Ph | | $CH_2CH_2N(Cbz)$ | H | Cl | $CH_3$ | H | 0.0003 | compound 25

SPIROINDOLINONES AND THERAPEUTIC USES THEREOF

CROSS REFERENCE TO RELATED APPLICATIONS

This application is a national stage of International Application No. PCT/US2016/037251, filed Jun. 13, 2016, which application claims priority to U.S. Provisional Application No. 62/175,202, filed Jun. 12, 2015.

STATEMENT REGARDING FEDERALLY SPONSORED RESEARCH

This invention was made with Governmental support under Grant No. R01GM117111 awarded by the National Institute of Health. The government has certain rights in the invention.

FIELD OF THE INVENTION

The invention is generally directed to spiroindolinone-containing small molecules and pharmaceutically acceptable salts thereof, methods of manufacturing such small molecules, and methods for the treatment of fungal or microbial disorders using such therapeutics.

BACKGROUND

*Candida* sp account for 80% of major systemic fungal infections. (Revankar, S. G.; Sobel, J. D., Eds. *Candidiasis* (Invasive). Merck Manual, 2014) The mortality rate for invasive candidiasis has been estimated around 40%. (Ahmadi, A., et al. *JRSM Open* 2014, 5, 1-10) Azoles remain a first-line treatment for many systemic fungal infections. All azole antifungal drugs act on the same fungal enzyme 14α-demethylase, but exhibit varying levels of activity against different species and strains. Fluconazole remains the most widely prescribed azole drug. Fluconazole has high bioavailability and is well tolerated; it is the first line antifungal treatment for candidiasis and is now available in generic form. (See, e.g., Kauffman, C. A. *UpToDate* Sep. 23, 2014. Marr, K. A. and Thorner, A. R., eds; Rex, J. H., et al. *N. Engl. J. Med.* 1994, 331, 1325-1330; Phillips, P., et al. *Eur. J. Clin. Microbiol. Infect. Dis.* 1997, 16, 337-345; Anaissie, E. J., et al. *Clin. Infect. Dis.* 1996, 23, 964-972; and Rex, J. H., et al. *Clin. Infect. Dis.* 2003, 36, 1221-1228.) However, there are reports of side effects, including hepatitis, leukopenia, thrombocytopenia, gastrointestinal distress, headache, anaphylaxis and rash. (See, e.g., Su, F. W., et al. *Allergy* 2003, 58, 1215-1216; Craig, T. J., et al. *J. Allergy Clin. Immunol.* 1996, 98, 845-846; Neuhaus, G., et al. *BMJ* 1991, 302, 1341; Gussenhoven, M. J. E., et al. *Lancet* 1991, 338, 120; Abbot, M., et al. *Lancet* 1991, 338, 633; and Slavin, M. A., et al. *J. Infect. Dis.* 1995, 171, 1545-1552.) Moreover, resistance to fluconazole and other azole drugs remains a major problem, particularly among immunocompromised patients, and resistant strains of *Candida* require higher doses of fluconazole. Higher doses of any drug, including fluconazole, can lead to an increased risk of adverse side effects. (See, e.g., Czaika, V., et al. *New Microbiol.* 2014, 37, 465-494; and Tobudic, S., et al. Mycoses 2012, 55, 24-32.)

Compounds that synergize with fluconazole at low concentrations (e.g., $MIC_{90}$<0.1 µg/mL) are unusual. The antifungal agents flucytosine, and fenpropimorph have been shown to potently synergize with fluconazole against various strains of *C. albicans*. (See, e.g., Scalarone, G. M., et al. *Mycoses* 1991, 34, 405-410; Sekine, Y., et al. *Chemotherapy* 1994, 42, 164-171; Te Dorsthorst, D. T., et al. *Antimicrob. Agents Chemother.* 2002, 46, 2982-2589; Pfaller, M. A., et al. *Antimicrob. Agents Chemother.* 2002, 46, 3518-3521; Jansen, G., et al. *Mol. Syst. Biol.* 2009, 5, 1-13; Nishi, I., et al. *J. Infect. Chemother.* 2009; 15, 1-5; Messer, S. A., et al. *J. Clin. Microbiol.* 2006, 44, 324-326; and Rodriguez, M. M., et al. *J. Antimicrob. Chemother.* 2007, 60, 188-190.) Micafungin and caspofungin are highly potent, but not synergistic with fluconazole, with FIC indices above 1.0. A number of drugs commonly used against non-fungal human diseases have also been shown to synergize with azoles against *C. albicans*. (See, e.g., Cruz, M. C., et al. *EMBO J.* 2002, 21, 546-559; and Sun, S., et al. *Antimicrob. Agents Chemother.* 2008, 52, 409-417.) The calcineurin inhibiting drug tacrolimus potently enhances the activity of fluconazole against *C. albicans*. Quite a few other compounds have been reported to inhibit the growth of *Candida* in synergy with fluconazole, with $MIC_{90}$s below 1 µg/mL, but not below 0.1 µg/mL: e.g., *T. broussonetii* extract, terbinafine, amlodarone, catechin, quercetin, epigallocatechin, simvastatin, tunicamycin, cationic peptides IJ3, IJ4 and VS3, ketorolac, cyclosporin A, nystatin, sanguinarine, allicin, declofenac, leaf extracts of *Lippia alba*, diphenyldiselenide, balcalein, geldanamycin, pseudolaric acid B, and doxycycline. Hundreds of other compounds have been reported to exhibit antifungal activity in concert with azoles but not below 1 µM.

(See, e.g., Saad, A., et al. *Phytomedicine* 2010, 17, 1057-1060; Barchiesi, F., et al. *Antimicrob. Agents Chemother.* 1997, 41, 1812-1814; da Silva, C. R., et al. *Antimicrob. Agents Chemother.* 2013, 57, 1691-1700; da Silva, C. R., et al. *Antimicrob. Agents Chemother.* 2014, 58, 1468-1478; Menezes, E. A., et al. *Rev. Inst. Med. Trop. Sao Paulo* 2012, 54, 197-199; Maurya, I. K., et al. *Biochim. Biophys. Acta.* 2013, 1830, 5193-5203; Maurya, I. K., et al. *Peptides* 2011, 32, 1732-1740; Abdelmegeed, E., et al. *J. Microbiol.* 2013, 51, 598-604; Marchetti, O., et al. *Antimicrob. Agents Chemother.* 2000, 44, 2373-2381; Guo, X.-J., et al. *The Chinese Journal of Dermatovenereology* 2007, 21, 277-279; Zhang, J., et al. *Mycopathologia* 2013, 175, 273-279; Ahodavandi, A., et al. *Mycopathologia* 2010, 169, 287-295; Oliveira, G. T., et al. *Rev. Soc. Bras. Med. Trop.* 2014, 47, 247-250; Denardi, L. B., et al. *Mycopathologia* 2013, 176, 165-169; Serpa, R., et al. *J. Med. Microbiol.* 2012, 61, 1704-1708; Guo, N., et al. *Mycoses* 2011, 54, e400-e406; Gao, Y., et al. *FEMS Yeast Res.* 2013, 13, 453-462; Quan, H., et al. *Antimicrob. Agents Chemother.* 2006, 50, 1096-1099; Xu, Y., et al. *J. Proteome Res.* 2009, 8, 5296-5304; Iwazaki, R. S., et al. *Antonie van Leeuwenhoek* 2010, 97, 201-205; Wei, G. X., et al. *Arch. Oral Biol.* 2011, 56, 565-572; and Liu, H., et al. *ChemMedChem* 2014, 9, 207-216.)

SUMMARY OF THE INVENTION

In many embodiments the invention is directed to small molecules in the nature of spiroindolinones, medicaments formed from these small molecules, methods for the treatment of disorders using such therapeutics are disclosed, and stereoselective methods for manufacturing such molecules.

Some embodiments are directed to compounds according to the following:

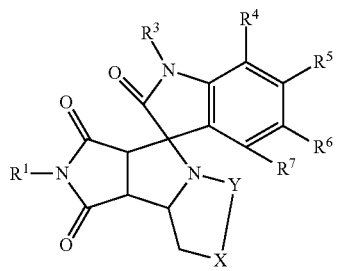

wherein:
R[1] is one of the following: an unsubstituted or substituted phenyl, an unsubstituted or substituted naphthyl, an unsubstituted or substituted heteroaryl, an unsubstituted or substituted benzyl, a C2-C6 alkyl, a C3-C6 alkynyl, a C2-C6 alkoxyalkyl, a C3-C7 cycloalkyl, or a C5-C7 cycloalkenyl;
Y—X is C=C as part of an aromatic or heteroaromatic ring; or Y is one of the following: $CH_2$, $CH_2CH_2$, or $C(O)CH_2$, and X is one of the following: O, S, $NR^2$, N—Z—$R^2$, $CR^2Q$, C=C as part of an aromatic or heteroaromatic ring;
Q is one of the following: $OR^{2'}$, $SR^{2'}$, $NHR^{2'}$, $NR^{2'}R^{2''}$, $N_3$, $NO_2$, CN, or $R^2$;
Z is one of the following: carbonyl, sulfur, an oxidized form of sulfur, an oxidized form of phosphorus;
R[2], R[2'] and R[2''] are each independently one of the following: H, an unsubstituted or substituted aryl, an unsubstituted or substituted heteroaryl, an unsubstituted or substituted benzyl, an unsubstituted or substituted phenethyl, a substituted or unsubstituted C1-C9 alkyl, a substituted or unsubstituted C3-C9 cycloalkyl, a substituted or unsubstituted C3-C9 cycloalkenyl, a substituted or unsubstituted C2-C9 alkenyl, a substituted or unsubstituted C2-C9 alkynyl, a substituted or unsubstituted C2-C9 alkoxyalkyl, a substituted or unsubstituted C1-C10 alkoxy, a substituted or unsubstituted C1-C10 acyloxy, a substituted or unsubstituted C1-C10 carbamoyl, an unsubstituted or substituted benzyloxy, a substituted or unsubstituted C4-C10 cycloalkoxy, a substituted or unsubstituted C1-C8 alkylamino, a substituted or unsubstituted C4-C7 cycloalkylamino, an unsubstituted or substituted benzylamino, an unsubstituted or substituted arylamino; R[3] is one of the following: H, an unsubstituted or substituted benzyl, a substituted or unsubstituted C2-C6 alkyl, a substituted or unsubstituted C2-C6 alkynyl, a substituted or unsubstituted C1-C6 alkoxyalkyl, a substituted or unsubstituted C3-C7 cycloalkyl, a substituted or unsubstituted C5-C7 cycloalkenyl, an alkanesulfonyl, an arenesulfonyl, hydroxyl or, a substituted or unsubstituted C1-C6 alkyloxy;
R[4], R[5], either form a five-membered or six-membered heteroaryl or heterocyclyl ring, or are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, an unsubstituted or substituted aryl group, an unsubstituted or substituted heteroaryl group, a substituted or unsubstituted an alkanesulfonyl, an unsubstituted or substituted arenesulfonyl, an unsubstituted or substituted arenesulfinyl, cyano, nitro, a substituted or unsubstituted amino group, a carboxylic acid, a substituted or unsubstituted carboxamide, or a substituted or unsubstituted C1-C6 carboxyalkyl; and
R[6] and R[7] are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, an optionally substituted aryl group, an optionally substituted heteroaryl group, a substituted or unsubstituted an alkanesulfonyl, an optionally substituted arenesulfonyl, an optionally substituted arenesulfinyl, cyano, nitro, a substituted or unsubstituted amino group, a carboxylic acid, a substituted or unsubstituted carboxamide, or a substituted or unsubstituted C1-C6 carboxyalkyl.

In other embodiments the indolone arene ring, the succinimide ring, and the $CH_2$ group of the ring comprised of CH—$CH_2$—X—Y—N are all disposed on the same face of the central spiropyrrolidine ring:

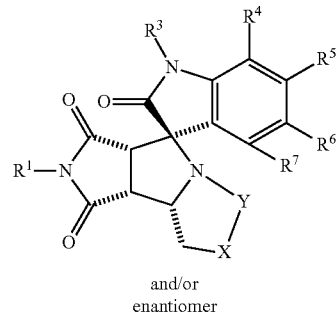

and/or enantiomer

In other embodiments the compound includes one of the following combinations of functional groups:
where Y is $CH_2$, X is CHQ and when Q is not H, but instead one of the following: hydroxy, F, Cl, a substituted or unsubstituted C1-C10 alkoxy, a substituted or unsubstituted C4-C6 cycloalkoxy, an optionally substituted benzyloxy, a substituted or unsubstituted C1-C10 acyloxy, cyano, a substituted or unsubstituted C1-C10 alkoxycarbonyl, a substituted or unsubstituted C1-C10 alkylaminocarbonyl, an optionally substituted aryl, an optionally substituted heteroaryl, an optionally substituted benzyl, an optionally substituted phenethyl, a substituted or unsubstituted C1-C9 alkyl, an optionally substituted heterocycle, a substituted or unsubstituted C3-C9 cycloalkyl, a substituted or unsubstituted C5-C6 cycloalkenyl, a substituted or unsubstituted C2-C9 alkenyl, a substituted or unsubstituted C2-C9 alkynyl, a substituted or unsubstituted C2-C9 alkoxyalkyl, a substituted or unsubstituted C1-C10 carbamoyl, a substituted or unsubstituted C1-C8 alkylamino, amino, a substituted or unsubstituted C4-C7 cycloalkylamino, an optionally substituted benzylamino, an optionally substituted arylamino;
In other embodiments where Y—X is C=C and part of an aromatic or heteroaromatic ring.

In other embodiments the compound includes one of the following combinations of functional groups:
- where X is C=C and is part of an aromatic or heteroaromatic ring that includes atom Y;
- where Y is $CH_2CH_2$, X is N, and Z is one of the following: carbonyl, sulfur, an oxidized form of sulfur, an oxidized form of phosphorus;
- where Y is $CH_2CH_2$, X is N, and Z is CO;
- where Y is $CH_2CH_2$, X is N, Z is CO, and $R^3$ is H;
- where Y is $CH_2CH_2$, X is N, Z is CO, and each of $R^3$, $R^6$, and $R^7$ are H;
- where Y is $CH_2CH_2$, X is N, Z is CO, each of $R^3$, $R^6$, and $R^7$ are H, $R^4$ is $CH_3$, and $R^5$ is either Cl or $CH_3$;
- where Y is $CH_2CH_2$, X is N, Z is CO, each of $R^3$, $R^6$, and $R^7$ are H, and $R^1$ is a substituted or unsubstituted aryl or heteroaryl;
- where Y is $CH_2CH_2$, X is N, Z is CO, each of $R^3$, $R^6$, and $R^7$ are H, and $R^2$ is either t-butoxy or benzyloxy; and
- where Y is $CH_2CH_2$, X is N, Z is CO, each of $R^3$, $R^6$, and $R^7$ are H, $R^4$ is $CH_3$, $R^5$ is Cl, $R^1$ is phenyl, and $R^2$ is benzyloxy.

In still other embodiments the compound is in the form of a pharmaceutically acceptable salt.

In yet other embodiments the compound is an enantiomer or a mixture of enantiomers.

Other embodiments are directed to a compound according to the following:

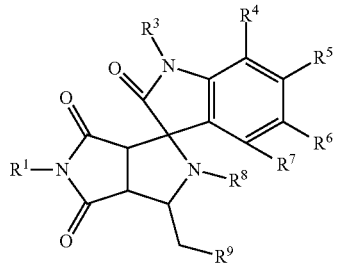

wherein:
- $R^1$ is one of the following: a substituted or unsubstituted phenyl, a substituted or unsubstituted naphthyl, a substituted or unsubstituted heteroaryl, a substituted or unsubstituted benzyl, C2-C6 alkyl, C3-C6 alkynyl, C2-C6 alkoxyalkyl, C3-C7 cycloalkyl, or C5-C7 cycloalkenyl;
- $R^3$ is one of the following: H, a substituted or unsubstituted benzyl, a substituted or unsubstituted C2-C6 alkyl, a substituted or unsubstituted C2-C6 alkynyl, a substituted or unsubstituted C1-C6 alkoxyalkyl, a substituted or unsubstituted C3-C7 cycloalkyl, a substituted or unsubstituted C5-C7 cycloalkenyl, an alkanesulfonyl, an arenesulfonyl, hydroxy, or a substituted or unsubstituted C1-C6 alkyloxy;
- $R^4$ and $R^5$ either form a five-membered or six-membered heteroaryl or heterocyclyl ring or are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, a substituted or unsubstituted aryl group, a substituted or unsubstituted heteroaryl group, a substituted or unsubstituted an alkanesulfonyl, a substituted or unsubstituted arenesulfonyl, a substituted or unsubstituted arenesulfinyl, cyano, nitro, a substituted or unsubstituted amino group, a carboxylic acid, a substituted or unsubstituted carboxamide, or a substituted or unsubstituted C1-C6 carboxyalkyl;
- $R^6$ and $R^7$ are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, a substituted or unsubstituted aryl group, a substituted or unsubstituted heteroaryl group, a substituted or unsubstituted an alkanesulfonyl, a substituted or unsubstituted arenesulfonyl, a substituted or unsubstituted arenesulfinyl, cyano, nitro, a substituted or unsubstituted amino group, a carboxylic acid, a substituted or unsubstituted carboxamide, or a substituted or unsubstituted C1-C6 carboxyalkyl; and
- $R^9$ is a substituted or unsubstituted aromatic or a substituted or unsubstituted heteroaromatic.

In other embodiments the compound further includes one of the following combinations of functional groups:
- where $R^4$ is methyl and each of $R^3$, $R^6$, $R^7$ and $R^8$ are H;
- where $R^1$ is a substituted or unsubstituted phenyl, $R^3$ is H, $R^4$ is methyl and $R^9$ is a substituted or unsubstituted aryl: phenyl, naphthyl, imidazole, pyrazole, furan, oxazole, isoxazole, isothiazole, thiophene, thiazole, triazole, furazan, oxadiazole, pyridine, pyrazine, pyrimidine, quinoline, isoquinoline, benzothiazole, benzimidazole, benzothiophene, benzotriazole;
- where $R^1$ is a substituted or unsubstituted phenyl, $R^3$ is H, $R^4$ is methyl and $R^9$ is a substituted or unsubstituted C1-C6 alkyl, a substituted or unsubstituted C3-C7 cycloalkyl, a substituted or unsubstituted C3-C7 cycloalkenyl, a substituted or unsubstituted C2-C6 alkenyl, a substituted or unsubstituted C2-C6 alkynyl, a substituted or unsubstituted C2-C6 alkoxyalkyl, a substituted or unsubstituted C1-C6 alkoxy, a substituted or unsubstituted C1-C6 acyloxy, a substituted or unsubstituted C1-C6 carbamoyl, an unsubstituted or substituted benzyloxy, a substituted or unsubstituted C4-C6 cycloalkoxy;
- where $R^1$ is a substituted or unsubstituted phenyl, $R^3$, $R^6$, and $R^7$ are H, $R^4$ is methyl, $R^5$ is Cl or methyl, and $R^9$ is a substituted or unsubstituted aryl: phenyl, naphthyl, imidazole, pyrazole, furan, oxazole, isoxazole, isothiazole, thiophene, thiazole, triazole, furazan, oxadiazole, pyridine, pyrazine, pyrimidine, quinoline, isoquinoline, benzothiazole, benzimidazole, benzothiophene, benzotriazole;
- where $R^1$ is a substituted or unsubstituted phenyl, $R^3$, $R^6$, and $R^7$ are H, $R^4$ is methyl, $R^5$ is Cl or methyl, and $R^9$ is a substituted or unsubstituted C1-C6 alkyl, a substituted or unsubstituted C3-C7 cycloalkyl, a substituted or unsubstituted C3-C7 cycloalkenyl, a substituted or unsubstituted C2-C6 alkenyl, a substituted or unsubstituted C2-C6 alkynyl, a substituted or unsubstituted C2-C6 alkoxyalkyl, a substituted or unsubstituted C1-C6 alkoxy, a substituted or unsubstituted C1-C6 acyloxy, a substituted or unsubstituted C1-C6 carbamoyl, an unsubstituted or substituted benzyloxy, a substituted or unsubstituted C4-C6 cycloalkoxy;
- where $R^3$, $R^6$, and $R^7$ are H, $R^4$ is methyl, $R^5$ is Cl and $R^9$ is a substituted or unsubstituted phenyl and $R^1$ is C3-C8 alkyl, C3-C8 cycloalkyl, C3-C8 alkenyl, C3-C8 alkynyl, C3-C8 alkynyl, or C3-C8 alkoxylalkyl;
where $R^1$ is a phenyl, $R^3$, $R^6$, $R^7$, and $R^8$ are H, $R^4$ is methyl, $R^5$ is Cl, and $R^9$ phenyl; and
where $R^1$ is a cycloheptyl, $R^3$, $R^6$, $R^7$, and $R^8$ are H, $R^4$ is methyl, $R^5$ is Cl, and $R^9$ phenyl.

In other embodiments the indolone arene ring, the succinimide ring, and the $CH_2$—$R^9$ group are all disposed on the same face of the central pyrrolidine ring:

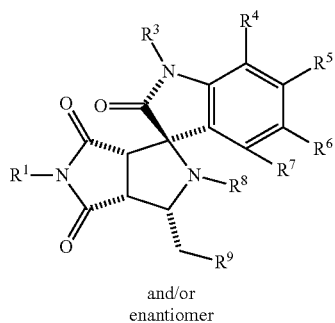

and/or
enantiomer wherein:
$R^1$ is one of the following: a substituted or unsubstituted phenyl, a substituted or unsubstituted naphthyl, a substituted or unsubstituted heteroaryl, a substituted or unsubstituted benzyl, C2-C6 alkyl, C3-C6 alkynyl, C2-C6 alkoxyalkyl, C3-C7 cycloalkyl, or C5-C7 cycloalkenyl;
$R^3$ is one of the following: H, a substituted or unsubstituted benzyl, a substituted or unsubstituted C2-C6 alkyl, a substituted or unsubstituted C2-C6 alkynyl, a substituted or unsubstituted C1-C6 alkoxyalkyl, a substituted or unsubstituted C3-C7 cycloalkyl, a substituted or unsubstituted C5-C7 cycloalkenyl, an alkanesulfonyl, an arenesulfonyl, hydroxy, or a substituted or unsubstituted C1-C6 alkyloxy;
$R^4$ and $R^5$ either form a five-membered or six-membered heteroaryl or heterocyclyl ring or are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, a substituted or unsubstituted aryl group, a substituted or unsubstituted heteroaryl group, a substituted or unsubstituted an alkanesulfonyl, a substituted or unsubstituted arenesulfonyl, a substituted or unsubstituted arenesulfinyl, cyano, nitro, a substituted or unsubstituted amino group, a carboxylic acid, a substituted or unsubstituted carboxamide, or a substituted or unsubstituted C1-C6 carboxyalkyl;
$R^6$ and $R^7$ are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, a substituted or unsubstituted aryl group, a substituted or unsubstituted heteroaryl group, a substituted or unsubstituted an alkanesulfonyl, a substituted or unsubstituted arenesulfinyl, cyano, nitro, a substituted or unsubstituted amino group, a carboxylic acid, a substituted or unsubstituted carboxamide, or a substituted or unsubstituted C1-C6 carboxyalkyl; and
$R^9$ is a substituted or unsubstituted aromatic or a substituted or unsubstituted heteroaromatic.

In other embodiments the compound further includes one of the following combinations of functional groups:
where $R^4$ is methyl and each of $R^3$, $R^6$, $R^7$ and $R^8$ are H;
where $R^1$ is a substituted or unsubstituted phenyl, $R^3$ is H, $R^4$ is methyl and $R^9$ is a substituted or unsubstituted aryl: phenyl, naphthyl, imidazole, pyrazole, furan, oxazole, isoxazole, isothiazole, thiophene, thiazole, triazole, furazan, oxadiazole, pyridine, pyrazine, pyrimidine, quinoline, isoquinoline, benzothiazole, benzimidazole, benzothiophene, benzotriazole;
where $R^1$ is a substituted or unsubstituted phenyl, $R^3$ is H, $R^4$ is methyl and $R^9$ is a substituted or unsubstituted C1-C6 alkyl, a substituted or unsubstituted C3-C7 cycloalkyl, a substituted or unsubstituted C3-C7 cycloalkenyl, a substituted or unsubstituted C2-C6 alkenyl, a substituted or unsubstituted C2-C6 alkynyl, a substituted or unsubstituted C2-C6 alkoxyalkyl, a substituted or unsubstituted C1-C6 alkoxy, a substituted or unsubstituted C1-C6 acyloxy, a substituted or unsubstituted C1-C6 carbamoyl, an unsubstituted or substituted benzyloxy, a substituted or unsubstituted C4-C6 cycloalkoxy;
where $R^1$ is a substituted or unsubstituted phenyl, $R^3$, $R^6$, and $R^7$ are H, $R^4$ is methyl, $R^5$ is Cl or methyl, and $R^9$ is a substituted or unsubstituted aryl: phenyl, naphthyl, imidazole, pyrazole, furan, oxazole, isoxazole, isothiazole, thiophene, thiazole, triazole, furazan, oxadiazole, pyridine, pyrazine, pyrimidine, quinoline, isoquinoline, benzothiazole, benzimidazole, benzothiophene, benzotriazole;
where $R^1$ is a substituted or unsubstituted phenyl, $R^3$, $R^6$, and $R^7$ are H, $R^4$ is methyl, $R^5$ is Cl or methyl, and $R^9$ is a substituted or unsubstituted C1-C6 alkyl, a substituted or unsubstituted C3-C7 cycloalkyl, a substituted or unsubstituted C3-C7 cycloalkenyl, a substituted or unsubstituted C2-C6 alkenyl, a substituted or unsubstituted C2-C6 alkynyl, a substituted or unsubstituted C2-C6 alkoxyalkyl, a substituted or unsubstituted C1-C6 alkoxy, a substituted or unsubstituted C1-C6 acyloxy, a substituted or unsubstituted C1-C6 carbamoyl, an unsubstituted or substituted benzyloxy, a substituted or unsubstituted C4-C6 cycloalkoxy;
where $R^3$, $R^6$, and $R^7$ are H, $R^4$ is methyl, $R^5$ is Cl and $R^9$ is a substituted or unsubstituted phenyl and $R^1$ is C3-C8 alkyl, C3-C8 cycloalkyl, C3-C8 alkenyl, C3-C8 alkynyl, C3-C8 alkynyl, or C3-C8 alkoxylalkyl;
where $R^1$ is a phenyl, $R^3$, $R^6$, $R^7$, and $R^8$ are H, $R^4$ is methyl, $R^5$ is Cl, and $R^9$ phenyl; and
where $R^1$ is a cycloheptyl, $R^3$, $R^6$, $R^7$, and $R^8$ are H, $R^4$ is methyl, $R^5$ is Cl, and $R^9$ phenyl.

In still other embodiments the compound is in the form of a pharmaceutically acceptable salt.

In yet other embodiments the compound is an enantiomer or a mixture of enantiomers.

Still other embodiments are directed to a medicament for the treatment of a disorder including a pharmaceutical formulation containing a therapeutically effective amount of one or more spiroindolinone small molecule compounds described above.

In still other embodiments the medicament is formulated for a form of administration selected from the group consisting of oral, parenteral, topical and transdermal.

In yet other embodiments the medicament is an active compound against eukaryotic cells.

In other embodiments the medicament is directed toward the treatment of a fungal disorder.

In still yet other embodiments the medicament is selected to inhibit Cdr1 in a pathogenic fungus.

In still yet other embodiments the medicament is administered against a pathogenic microorganism in conjunction with an antimicrobial drug.

In still yet other embodiments the medicament is administered in conjunction with an antifungal drug against a pathogenic fungus. In some such embodiments the antifungal drug is an azole drug or a pharmaceutically acceptable salt, and in some embodiments the drug or derived salt is selected from the group consisting of azoles, including triazoles: e.g., albaconazole, efinaconazole, itraconazole, fluconazole, terconazole, voriconazole, posaconazole, epoxiconazole, isavuconazole, ravuconazole, phosravuconazole; and imidazoles: clotrimazole, ketoconazole, bifonazole, butoconazole, econazole, fenticonazole, isoconazole, luliconazole, miconazole, omoconazole, oxiconazole, sertaconazole, sulconazole, tioconazole.

In still yet other embodiments the medicament is administered in conjunction with an antifungal drug selected from thiazoles: abafungin; naphthylmethylamines: butenafine, naftifine, terbinafine; and morpholines: amorolfine, fenpropimorph, dodemorph, tridemorph; flucytosine; tolnaftate; griseofulvin; cicloprimox; FK506; and cyclosporine.

In still yet other embodiments the pathogenic fungus is a strain of *Candida albicans, Candida glabrata, Cryptococcus* or *Aspergillus*.

Other embodiments provide a process for the stereoselective synthesis of spiroindolinones from isatins, maleimides, and cyclic amino acids containing a six-membered ring.

Yet other embodiments are directed to a method of treating disease in a patient including:

diagnosing a patient having a fungal disorder susceptible to treatment at least in part by eukaryotic cell regulation; and administering a therapeutically effective amount of one or more spiroindolinone small molecule compounds selected from those described above.

In other embodiments the method is directed toward the treatment of a fungal disorder.

In still other embodiments the method includes administering the small molecule compounds in a form selected from the group consisting of oral, topical, parenteral, and transdermal.

In yet other embodiments the method includes administering the small molecule compounds against a pathogenic microorganism in conjunction with an antimicrobial drug.

In still yet other embodiments the method includes administering the small molecule compounds to inhibit Cdr1.

In still yet other embodiments the method includes administering the small molecule compounds against a pathogenic fungus in conjunction with an antifungal drug. In some such embodiments the antifungal drug is an azole drug or a pharmaceutically acceptable salt, and in some embodiments the drug or derived salt is selected from the group consisting of triazoles: e.g., albaconazole, efinaconazole, itraconazole, fluconazole, terconazole, voriconazole, posaconazole, epoxiconazole, isavuconazole, ravuconazole, phosravuconazole; and imidazoles: clotrimazole, ketoconazole, bifonazole, butoconazole, econazole, fenticonazole, isoconazole, luliconazole, miconazole, omoconazole, oxiconazole, sertaconazole, sulconazole, tioconazole.

In still yet other embodiments the medicament is administered in conjunction with an antifungal drug selected from thiazoles: abafungin; naphthylmethylamines: butenafine, naftifine, terbinafine; and morpholines: amorolfine, fenpropimorph, dodemorph, tridemorph; flucytosine; tolnaftate; griseofulvin; cicloprimox; FK506; and cyclosporine.

In still yet other embodiments the pathogenic fungus is a strain of *Candida albicans, Candida glabrata, Cryptococcus* or *Aspergillus*.

Still yet other embodiments are directed to methods of screening for suitable antifungal drugs by examining the activity of the drug in the presence of a medicament using a Cdr1 efflux assay.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 6 provides a reaction pathway for the production of therapeutic small molecule analogues in accordance with various embodiments of the invention, and Table providing summaries of compounds made in accordance with embodiments.

FIG. 10 provides a Table summarizing studies on the structure-activity relationships of therapeutic small molecule analogues in accordance with the invention.

DETAILED DESCRIPTION

Figure 1:
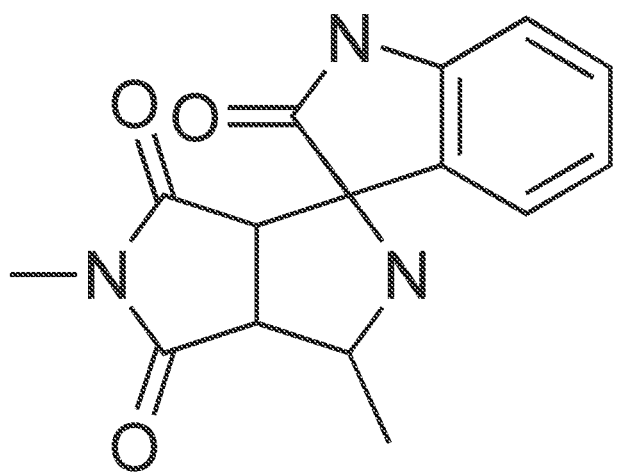
FIG. 1 provides a common core molecular structure of known spiroindolinones.
Figure 2A:
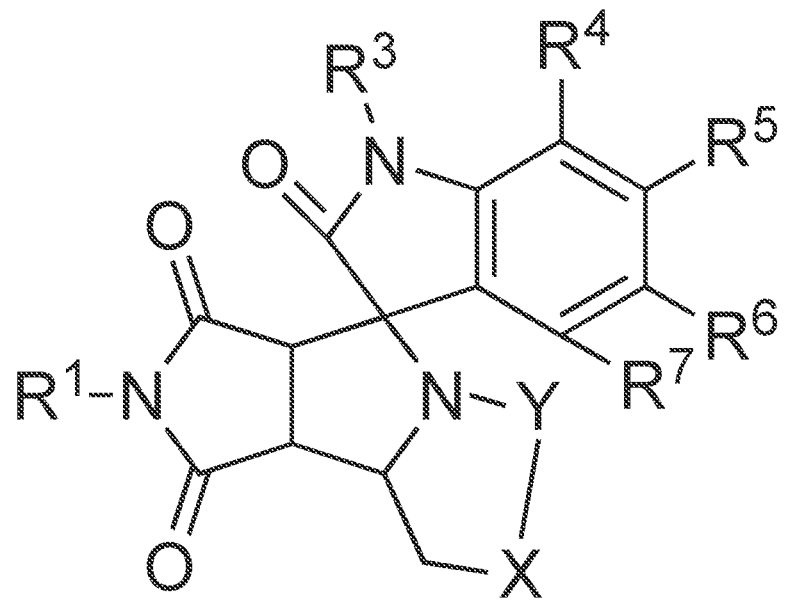
FIGS. 2a and 2b molecular structures of therapeutic spirocyclic small molecules in accordance with various embodiments of the invention.
Figure 2B:
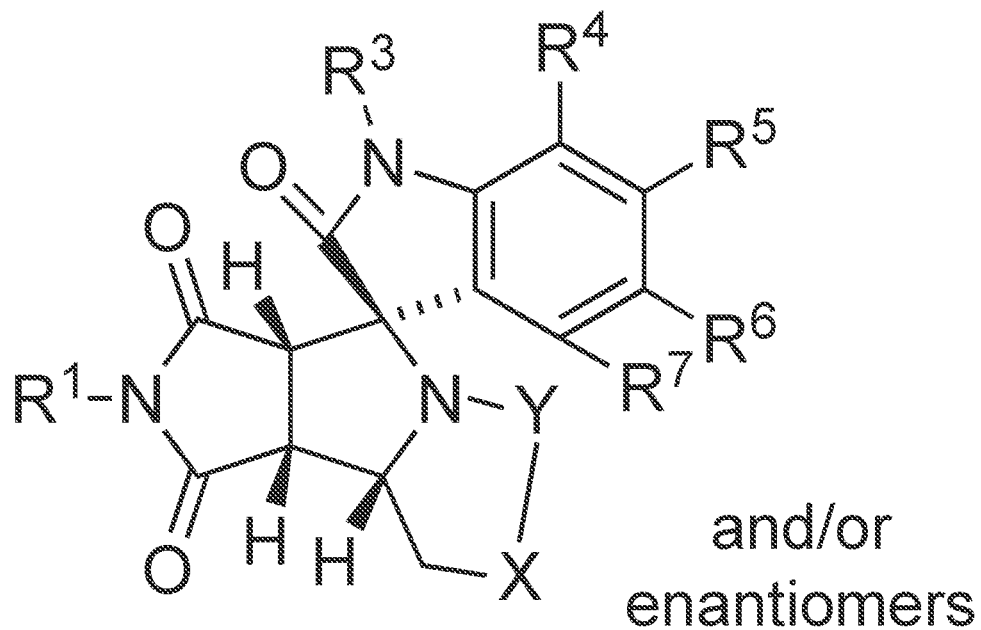
Figure 3A:
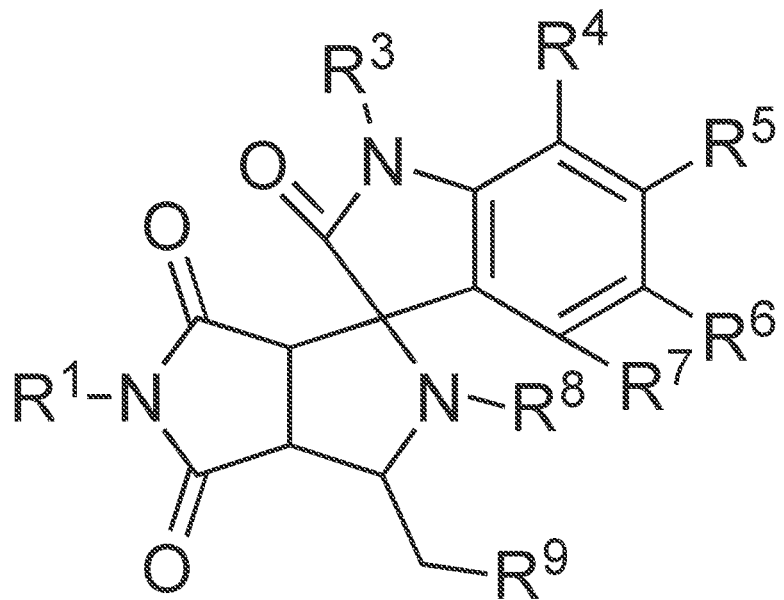
FIGS. 3a and 3b molecular structures of therapeutic spirocyclic small molecules in accordance with various embodiments of the invention.
Figure 3B:
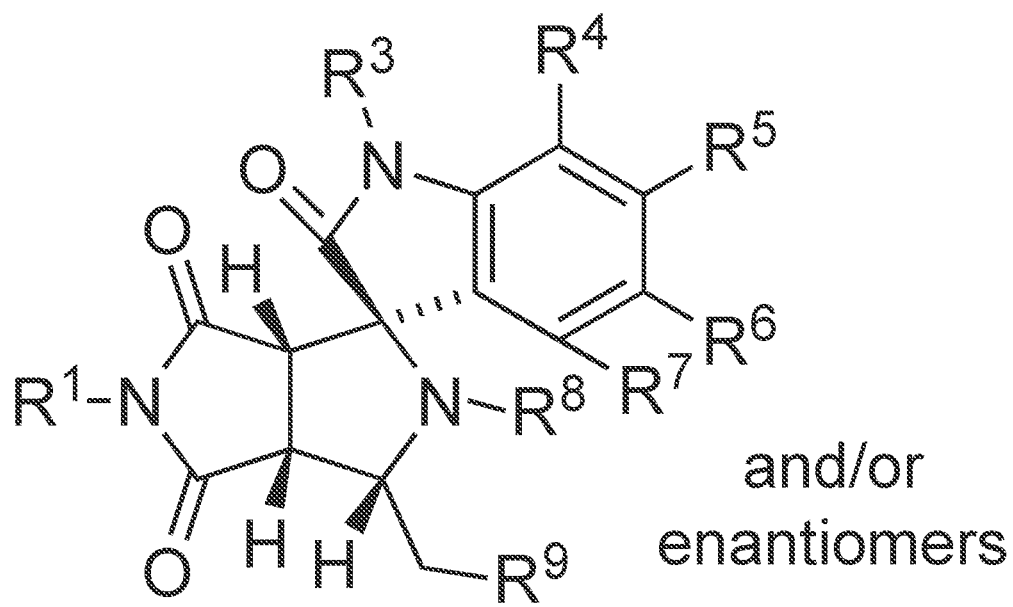

Turning now to the drawings and data, small molecules capable of treating disorders, including fungal and microbial infections, from a variety of therapeutic mechanisms including inhibiting the biochemical pathways in eukaryotic cells and enhancing the antifungal or antimicrobial activity of other antifungal or antimicrobial agents such as fluconazole, medicaments formed from these small molecules, methods for the treatment of fungal or microbial disorders using such therapeutics are disclosed, and stereoselective methods for preparing such compounds. The invention involves small molecules containing spiroindolinones attached to a central pyrrolidine ring that is fused to a succinimide (FIG. 1). In some embodiments, the small molecules are spiroindolinones containing an additional ring comprised of Y—X fused to the central pyrrolidine (FIGS. 2a and 2b). Additional embodiments of the spiroindolinone small molecules incorporate spirocyclic compounds in which the groups R8 and R9 are not part of the same ring (FIGS. 3a and 3b). Embodiments can exist in a pure compound form or in the form of pharmaceutically effective salts. Some embodiments are used alone or in combination with an active compound against eukaryotic cells. In other embodiments, formulations and medicaments are provided that are directed to the treatment of disease. In some such embodiments these formulations and medicaments target fungal or microbial infections, such as, for example, *C. albicans* and potentially other diseases. Many embodiments are directed to spiroindolinones that function through inhibiting Cdr1 (*Candida* Drug Resistance 1), a major drug efflux pump of the ATP-binding cassette (ABC) transporter superfamily, to enhance fluconazole activities. Therapeutic embodiments contain a therapeutically effective dose of one or more small molecule compounds, present either as a pharmaceutically effective salt or in pure form. Embodiments allow for various formulations, including, but not limited to, formulations for oral, intravenous, topical or intramuscular administration. Other additional embodiments provide treatment regimes for disorders using therapeutic amounts of the small molecules. In some treatment embodiments the small molecules, delivery systems and dosage regimes are directed to the treatment of fungal infections, such as, for example, *Candida, Candida glabrata* and *Cryptococcus* or *Aspergillus*, and potentially other diseases, such as microbial infections, including diseases in which the molecules are used in association with an azole drug, such as fluconazole.

Definitions

For the purposes of this description, the following definitions are used, unless otherwise described.

"Azoles" are a class of antifungal drugs that inhibit ergosterol biosynthesis; antifungal triazoles and antifungal imidazoles inhibit the enzyme lanosterol 14α-demethylase; thiazoles such as abafungin inhibit other enzymes in the ergosterol biosynthesis pathway.

"Lanosterol 14α-demethylase" (or CYP51A1) is a cytochrome P450 enzyme that is involved in the conversion of lanosterol to 4,4-dimethylcholesta-8(9),14,24-trien-3β-ol. In fungi, CYP51A1 catalyzes the demethylation of lanosterol to create an important precursor that is eventually converted into ergosterol, which then makes its way throughout the cell, where it alters the permeability and rigidity of plasma membranes much as cholesterol does in animals.

"Fluconazole" is an antifungal medication that is administered orally or intravenously. It is used to treat a variety of fungal infections, especially *Candida* infections of the vagina ("yeast infections'), mouth, throat, and bloodstream. It is also used to prevent infections in people with weak immune systems, including those with neutropenia due to cancer chemotherapy, transplant patients, and premature babies.

"Spiroindolinone" or spirocyclic pyrrolidinoindolinone is a 2',3',3a'-6a'-tetrahydro-4'H-spiro[indoline-3,1'-pyrrolo[3,4-c]pyrrole]-2,4',6'(5'H)-trione, including chemical analogues and stereoisomers.

Terms of Art

"CI" refers to clinical isolate.

"*C. albicans*" refers to *Candida albicans*.

"DIPEA" refers to N,N-diisopropylethylamine.

"DMSO" refers to dimethyl sulfoxide.

"EC" refers to effective concentration.

"EDC" refers to 1-ethyl-3-(3-dimethylaminopropyl)carbodiimide.

"FIC" refers to fractional inhibitory concentration.

"FICI" refers to fractional inhibitory concentration index.

"Halogen" or "halo" means fluoro (F), chloro (Cl), bromo (Br), or iodo (I).

"MIC" refers to minimum inhibitory concentration.

"OD" refers to optical density.

"R" in the chemical structures above and throughout are meant to indicate any suitable functional group.

"*T. broussonetii*" refers to *Thymus broussonetii*.

"TPSA" refers to topological polar surface area.

INTRODUCTION

Fluconazole is a first-generation triazole antifungal medication. It differs from other azole antifungals (such as ketoconazole) in that its structure contains a triazole ring instead of an imidazole ring. While the imidazole antifungals are mainly used topically, fluconazole and certain other triazole antifungals are preferred when systemic treatment is required because of their improved safety and predictable absorption when administered orally. However, there are reports of side effects, including hepatitis, leukopenia, thrombocytopenia, gastrointestinal distress, headache, anaphylaxis and rash. Moreover, resistance to fluconazole and other azole drugs remains a major problem particularly among immunocompromised patients. There is a compelling need for compositions that can increase the efficacy of existing antifungal and antimicrobial azole agents such as fluconazole.

Several groups have screened large libraries of compounds in search of small molecules that synergize with azoles such as fluconazole. In 2011, Spitzer and coworkers screened the Prestwick library of off-patent drugs and demonstrated that sertraline and thiethylperazine synergize with fluconazole. (Spitzer, M., et al. *Mol. Syst. Biol.* 2011, 21, 1-14.) The MIC for sertraline was as low as 0.5 µg/mL in the presence of fluconazole. More recently, Robbins and coworkers screened a larger collection of about 3600 small molecules to identify antifungal drug enhancers and identified chlorhexidine, hypocrelin A, and tomatidine to synergize in the micromolar range with fluconazole against a resistant clinical isolate of *C. albicans*. (Robbins, N., et al. *Cell Rep.* 2015, 13, 1481-1492.) Also in 2011, LaFleur and coworkers screened a library of 120,000 compounds in search of molecules that could act in synergy with clotrimazole against *C. albicans* biofilms, but none were active below 1 µM. (LaFleur, M. D., et al. *J. Antimicrob. Chemother.* 2011, 66, 820-826.) Starting in 2010 Lindquist, Schreiber, and others at the Broad Institute reported a screening campaign to identify small molecules capable of inhibiting growth of *C. albicans* in synergy with fluconazole with a particular interest in Hsp90 and calcineurin pathways. (See, National Center for Biotechnology Information. PubChem BioAssay Database; AID=2007, Source=Broad Institute.) After an initial screen of over 300,000 compounds and a subsequent rescreening, 296 compounds were found to have fluconazole dependent potency against a partially resistant clinical strain CaCi-8, and lack of cytotoxicity against mammalian fibroblasts. Three of those compounds were selected for further optimization but none of the resulting compounds (ML189, ML212, and ML229) were active below 0.7 µM against CaCi-8. (See, Youngsaye, W., et al. *J. Org. Chem.* 2013, 9, 1501-1507; Youngsaye, W., et al. *Bioorg. Med. Chem. Lett.* 2011, 21, 5502-5505; and Youngsaye, W., et al. *Bioorg. Med. Chem. Lett.* 2012, 22, 3362-3365.)

Figure 4A:
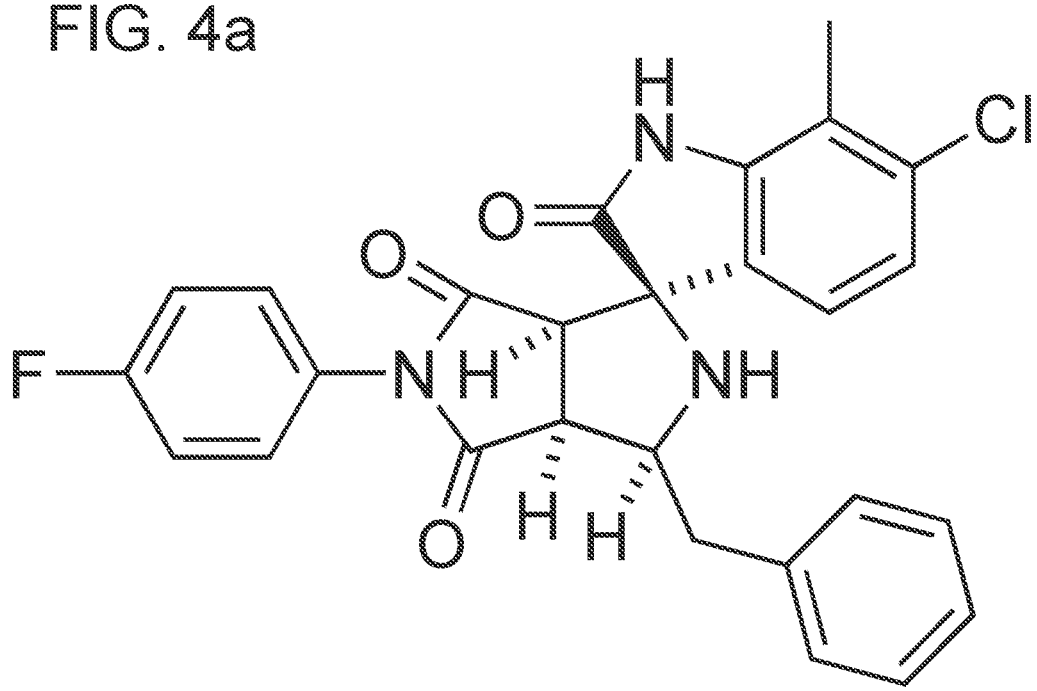
FIGS. 4a and 4b compares the molecular structure of the antifungal spiroindolinone in the prior art with spiroindolinone 1 embodied in this invention, respectively.

A survey of the PubChem database revealed 15,472 spiroindolinones with the core structure shown in FIG. 1 including charge variants. Thus far among the 15,472 spiroindolinones, only 34 were tested for antifungal synergy and of those only two spiroindolinones have been found to exhibit antifungal synergy with fluconazole. In these previous studies the complete relative stereochemistry of the spiroindolinones have typically not been described. Accordingly, it has not been possible to determine which combination of stereochemical configuration and functional groups are important for biological activity by comparing active compounds with inactive compounds. Indeed, most of the functional groups that were present on the two active spiroindolinones were also present on spiroindolinones with no measurable activity, and while the relative stereochemistry of the more active spiroindolinone (1S,3R,3aR,6aS)-1-benzyl-6'-chloro-5-(4-fluorophenyl)-7'-methylspiro[1,2,3a,6a-tetrahydropyrrolo[3,4-c]pyrrole-3,3'-1H-indole]-2',4,6-trione (FIG. 4a, PubChem CID 6584729) was fully specified, the full relative stereochemistry of the less active spiroindolinone was not fully specified.

It has now been discovered (Premachandra, et al. *ChemMedChem* 2015, 10, 1672-1686) that the stereochemistry of these spiroindolinones can have an impact on their activity, and some embodiments describe spiroindolinones with a relative stereochemistry different from the most active compound previously reported. In particular, some embodiments identify a stereochemical genus of spiroindolinone analogues (FIGS. 2b and 3b) in which the indolone carbonyl is on the same face as all three protons on the central spiropyrrolidine ring that are capable of potently inhibiting the growth of *C. albicans* in the presence of fluconazole; the relative stereochemistry of that genus of spiroindolinones is different from that of the active spiroindolinone from the prior art (PubChem CID 6584729, FIG. 4a). Spiroindolinones with a relative stereochemical configuration like those in FIGS. 2b and 4a can not be efficiently synthesized by methods known in the prior art. Accordingly, presented below are embodiments of small molecule spiroindolinone analogues and synthetically accessible diastereomers, therapeutics based on such small molecules, and treatment regimes incorporating such therapeutics for use in treating fungal infections and other disorders.

Exemplary Molecules

Compounds in accordance with embodiments of the invention are based on Spirocyclic Pyrrolidinoindolinones or spiroindolinones. Chemical compounds in accordance with embodiments of the invention are illustrated in FIGS. 2a, 2b and 3a, 3b as pictured below, and include their analogs or stereoselective diastereomers (including embodiments that have a relative configuration in which the indolone carbonyl is on the same face as all three protons on the central spiropyrrolidine ring), and include enantiomers, mixtures of enantiomers and pharmaceutically acceptable salts thereof. Two embodiments of the spirocyclic molecules in accordance with embodiments are provided in FIGS. 2a and 3a (Formulas I and II), below.

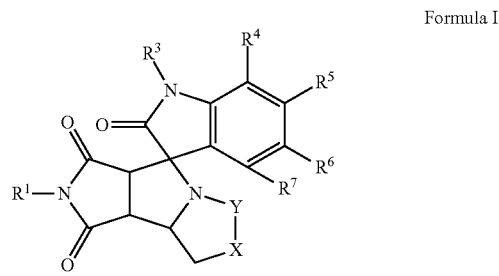

Formula I

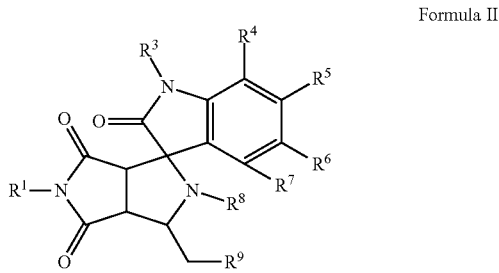

Formula II

Other embodiments of the spirocyclic compound in accordance with inventions are provided in accordance with the following exemplary structure where N—Y—X is part of a ring, and where the indolone arene ring, the succinimide ring, and the ring comprised of N—Y—X in Formula I are all disposed on the same face of the central spiropyrrolidine ring:

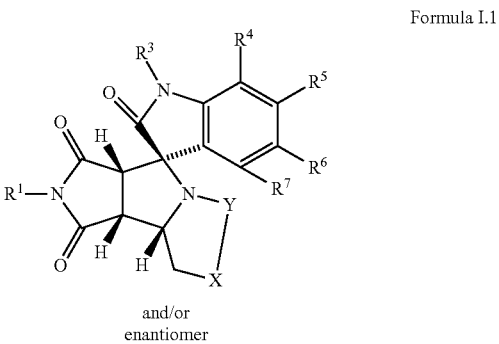

and/or enantiomer

Formula I.1

In either such embodiment the various elements of the molecule are as follows:

$R^1$ is one of the following: an unsubstituted or substituted phenyl, an unsubstituted or substituted naphthyl, an unsubstituted or substituted heteroaryl, an unsubstituted or substituted benzyl, a C2-C6 alkyl, a C3-C6 alkynyl, a C2-C6 alkoxyalkyl, a C3-C7 cycloalkyl, or a C5-C7 cycloalkenyl;

Y is one of the following: $CH_2$, $CH_2CH_2$, or $C(O)CH_2$;

X is one of the following: O, S, $NR^2$, N—Z—$R^2$, $CR^2Q$, or C=C as part of an aromatic or heteroaromatic ring that includes atom Y;

Q is one of the following: $OR^{2'}$, $SR^{2'}$, $NHR^{2'}$, $NR^{2'}R^{2''}$, $N_3$, $NO_2$, CN, or $R^2$;

Z is one of the following: carbonyl, sulfur, an oxidized form of sulfur, an oxidized form of phosphorus;

$R^2$, $R^{2'}$ and $R^{2''}$ are each independently one of the following: H, an unsubstituted or substituted aryl, an unsubstituted or substituted heteroaryl, an unsubstituted or substituted benzyl, an unsubstituted or substituted phenethyl, a substituted or unsubstituted C1-C9 alkyl, a substituted or unsubstituted C3-C9 cycloalkyl, a substituted or unsubstituted C3-C9 cycloalkenyl, a substituted or unsubstituted C2-C9 alkenyl, a substituted or unsubstituted C2-C9 alkynyl, a substituted or unsubstituted C2-C9 alkoxyalkyl, a substituted or unsubstituted C1-C10 alkoxy, a substituted or unsubstituted C1-C10 acyloxy, a substituted or unsubstituted C1-C10 carbamoyl, an unsubstituted or substituted benzyloxy, a substituted or unsubstituted C4-C10 cycloalkoxy, a substituted or unsubstituted C1-C8 alkylamino, a substituted or unsubstituted C4-C7 cycloalkylamino, an unsubstituted or substituted benzylamino, an unsubstituted or substituted arylamino; $R^3$ is one of the following: H, an unsubstituted or substituted benzyl, a substituted or unsubstituted C2-C6 alkyl, a substituted or unsubstituted C2-C6 alkynyl, a substituted or unsubstituted C1-C6 alkoxyalkyl, a substituted or unsubstituted C3-C7 cycloalkyl, a substituted or unsubstituted C5-C7 cycloalkenyl, an alkanesulfonyl, an arenesulfonyl, hydroxyl or, a substituted or unsubstituted C1-C6 alkyloxy;

$R^4$ and $R^5$, either form a five-membered or six-membered heteroaryl or heterocyclyl ring, or are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, an unsubstituted or substituted aryl group, an unsubstituted or substituted heteroaryl group, a substituted or unsubstituted an alkanesulfonyl, an unsubstituted or substituted arenesulfonyl, an unsubstituted or substituted arenesulfinyl, cyano, nitro, a substituted or unsubstituted amino group, a carboxylic acid, a substituted or unsubstituted carboxamide, or a substituted or unsubstituted C1-C6 carboxyalkyl; and $R^6$ and $R^7$ are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, an optionally substituted aryl group, an optionally substituted heteroaryl group, a substituted or unsubstituted an alkanesulfonyl, an optionally substituted arenesulfonyl, n optionally substituted arenesulfinyl, cyano, nitro, a substituted or unsubstituted amino group, a carboxylic acid, a substituted or unsubstituted carboxamide, or a substituted or unsubstituted C1-C6 carboxyalkyl.

In further embodiments Y is $CH_2$, X is CHQ, and Q is one of the following: hydroxy, F, Cl, a substituted or unsubstituted C1-C10 alkoxy, a substituted or unsubstituted C4-C6 cycloalkoxy, an optionally substituted benzyloxy, a substituted or unsubstituted C1-C10 acyloxy, cyano, a substituted or unsubstituted C1-C10 alkoxycarbonyl, a substituted or unsubstituted C1-C10 alkylaminocarbonyl, an optionally substituted aryl, an optionally substituted heteroaryl, an optionally substituted benzyl, an optionally substituted phenethyl, a substituted or unsubstituted C1-C9 alkyl, an optionally substituted heterocycle, a substituted or unsubstituted C3-C9 cycloalkyl, a substituted or unsubstituted C5-C6 cycloalkenyl, a substituted or unsubstituted C2-C9 alkenyl, a substituted or unsubstituted C2-C9 alkynyl, a substituted or unsubstituted C2-C9 alkoxyalkyl, a substituted or unsubstituted C1-C10 carbamoyl, a substituted or unsubstituted C1-C8 alkylamino, amino, a substituted or unsubstituted C4-C7 cycloalkylamino, an optionally substituted benzylamino, or an optionally substituted arylamino.

In still other embodiments, X is C=C and is part of an aromatic or heteroaromatic ring. A diagram exemplary of these embodiments is provided below.

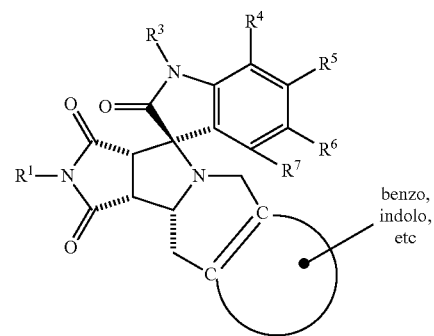

Formula I.2

In yet other embodiments, Y—X is C=C and part of an aromatic or heteroaromatic ring. A diagram exemplary of these embodiments is provided below.

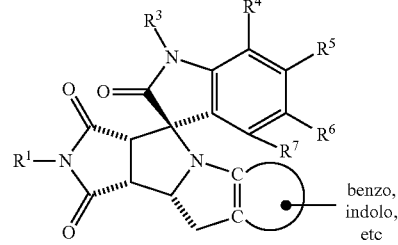

Formula I.3

In still yet other embodiments Y is $CH_2CH_2$, X is N, and Z is one of the following: carbonyl, sulfur, an oxidized form of sulfur, an oxidized form of phosphorus. A diagram exemplary of these embodiments is provided below.

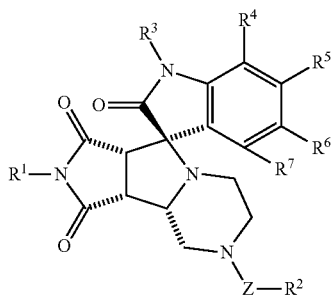

Formula I.4

In still yet other embodiments Y is $CH_2CH_2$, X is N, and Z is CO. A diagram exemplary of these embodiments is provided below.

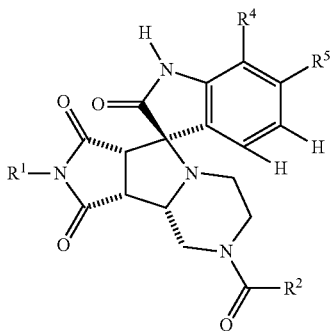

Formula I.8

In still yet other embodiments Y is $CH_2CH_2$, X is N, Z is CO, each of $R^3$, $R^6$, and $R^7$ are H, $R^4$ is $CH_3$, and $R^5$ is either Cl or $CH_3$. A diagram exemplary of these embodiments is provided below.

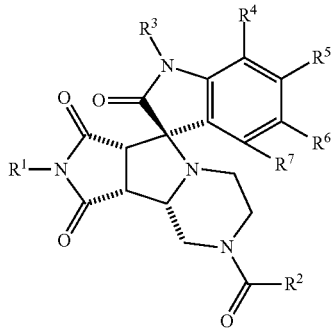

Formula I.6

In still yet other embodiments Y is $CH_2CH_2$, X is N, Z is CO, and $R^3$ is H. A diagram exemplary of these embodiments is provided below.

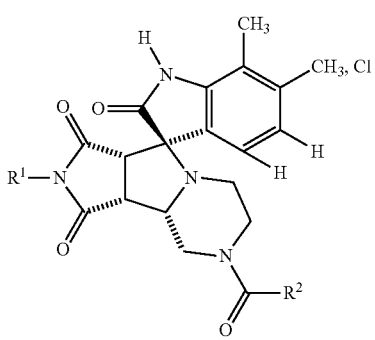

Formula I.9

In still yet other embodiments Y is $CH_2CH_2$, X is N, Z is CO, each of $R^3$, $R^6$, and $R^7$ are H, and $R^1$ is a substituted or unsubstituted aryl or heteroaryl. A diagram exemplary of these embodiments is provided below.

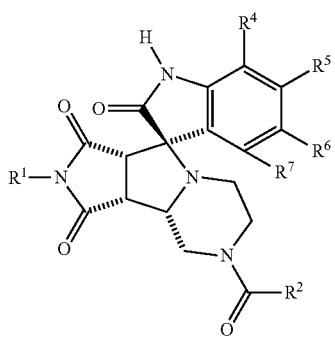

Formula I.7

In still yet other embodiments Y is $CH_2CH_2$, X is N, Z is CO, and each of $R^3$, $R^6$, and $R^7$ are H. A diagram exemplary of these embodiments is provided below.

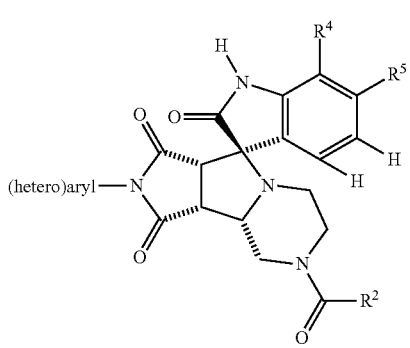

Formula I.10

In still yet other embodiments Y is $CH_2CH_2$, X is N, Z is CO, each of $R^3$, $R^6$, and $R^7$ are H, and $R^2$ is either t-butoxy or benzyloxy. A diagram exemplary of these embodiments is provided below.

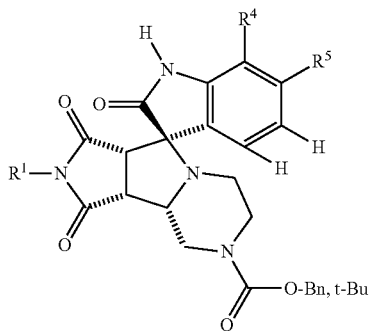

Formula I.11

In still yet other embodiments Y is CH$_2$CH$_2$, X is N, Z is CO, each of R$^3$, R$^6$, and R$^7$ are H, R$^4$ is CH$_3$, R$^5$ is Cl, R$^1$ is phenyl, and R$^2$ is benzyloxy. A diagram exemplary of these embodiments is provided below.

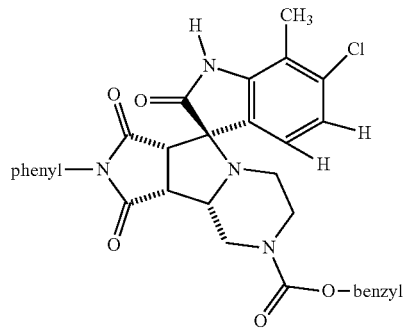

Formula I.12

Many embodiments of the spirocyclic compound are provided in accordance with the following exemplary structure where groups R$^8$ and R$^9$ are not part of the same ring as shown in Formula II:

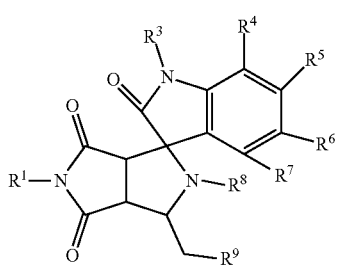

Formula II

In some such embodiments the succinimide ring, the indolone arene ring, and the CH$_2$—R$^9$ group in Formula II are on the same face of the central pyrrolidine ring. A diagram exemplary of these embodiments is provided below.

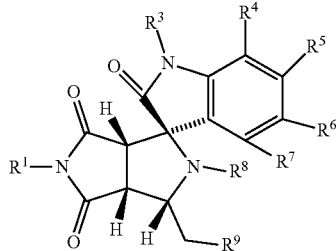

Formula II.1

In either such embodiment the various elements of the molecule are as follows:

R$^1$ is one of the following: a substituted or unsubstituted phenyl, a substituted or unsubstituted naphthyl, a substituted or unsubstituted heteroaryl, a substituted or unsubstituted benzyl, C2-C6 alkyl, C3-C6 alkynyl, C2-C6 alkoxyalkyl, C3-C7 cycloalkyl, or C5-C7 cycloalkenyl;

R$^3$ is one of the following: H, a substituted or unsubstituted benzyl, a substituted or unsubstituted C2-C6 alkyl, a substituted or unsubstituted C2-C6 alkynyl, a substituted or unsubstituted C1-C6 alkoxyalkyl, a substituted or unsubstituted C3-C7 cycloalkyl, a substituted or unsubstituted C5-C7 cycloalkenyl, an alkanesulfonyl, an arenesulfonyl, hydroxy, or a substituted or unsubstituted C1-C6 alkyloxy;

R$^4$ and R$^5$ either form a five-membered or six-membered heteroaryl or heterocyclyl ring or are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, a substituted or unsubstituted aryl group, a substituted or unsubstituted heteroaryl group, a substituted or unsubstituted an alkanesulfonyl, a substituted or unsubstituted arenesulfonyl, a substituted or unsubstituted arenesulfinyl, cyano, nitro, a substituted or unsubstituted amino group, a carboxylic acid, a substituted or unsubstituted carboxamide, or a substituted or unsubstituted C1-C6 carboxyalkyl;

R$^6$ and R$^7$ are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, a substituted or unsubstituted aryl group, a substituted or unsubstituted heteroaryl group, a substituted or unsubstituted an alkanesulfonyl, a substituted or unsubstituted arenesulfonyl, a substituted or unsubstituted arenesulfinyl, cyano, nitro, a substituted or unsubstituted amino group, a carboxylic acid, a substituted or unsubstituted carboxamide, or a substituted or unsubstituted C1-C6 carboxyalkyl; and R$^9$ is a substituted or unsubstituted aromatic or a substituted or unsubstituted heteroaromatic.

In other embodiments R$^4$ is methyl and each of R$^3$, R$^6$, R$^7$ and R$^8$ are H. A diagram exemplary of these embodiments is provided below.

Formula II.2

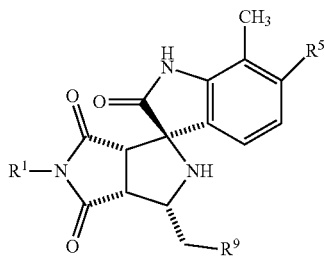

In still other embodiments $R^1$ is a substituted or unsubstituted phenyl, $R^3$ is H, $R^4$ is methyl and $R^9$ is a substituted or unsubstituted aryl: phenyl, naphthyl, imidazole, pyrazole, furan, oxazole, isoxazole, isothiazole, thiophene, thiazole, triazole, furazan, oxadiazole, pyridine, pyrazine, pyrimidine, quinoline, isoquinoline, benzothiazole, benzimidazole, benzothiophene, benzotriazole. A diagram exemplary of these embodiments is provided below.

Formula II.3

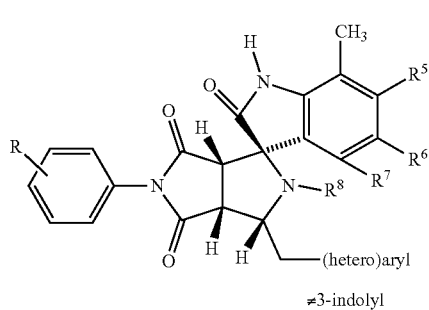

In still other embodiments $R^1$ is a substituted or unsubstituted phenyl, $R^3$ is H, $R^4$ is methyl and $R^9$ is a substituted or unsubstituted C1-C6 alkyl, a substituted or unsubstituted C3-C7 cycloalkyl, a substituted or unsubstituted C3-C7 cycloalkenyl, a substituted or unsubstituted C2-C6 alkenyl, a substituted or unsubstituted C2-C6 alkynyl, a substituted or unsubstituted C2-C6 alkoxyalkyl, a substituted or unsubstituted C1-C6 alkoxy, a substituted or unsubstituted C1-C6 acyloxy, a substituted or unsubstituted C1-C6 carbamoyl, an unsubstituted or substituted benzyloxy, a substituted or unsubstituted C4-C6 cycloalkoxy. A diagram exemplary of these embodiments is provided below.

Formula II.4

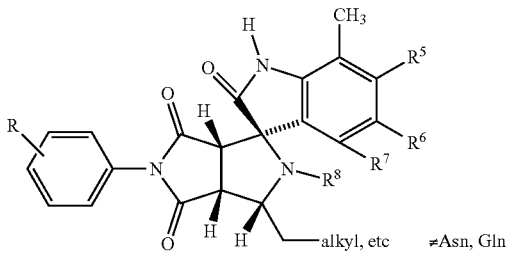

In still other embodiments $R^1$ is a substituted or unsubstituted phenyl, $R^3$, $R^6$, and $R^7$ are H, $R^4$ is methyl, $R^5$ is Cl or methyl, and $R^9$ is a substituted or unsubstituted aryl: phenyl, naphthyl, imidazole, pyrazole, furan, oxazole, isoxazole, isothiazole, thiophene, thiazole, triazole, furazan, oxadiazole, pyridine, pyrazine, pyrimidine, quinoline, isoquinoline, benzothiazole, benzimidazole, benzothiophene, benzotriazole. A diagram exemplary of these embodiments is provided below.

Formula II.5

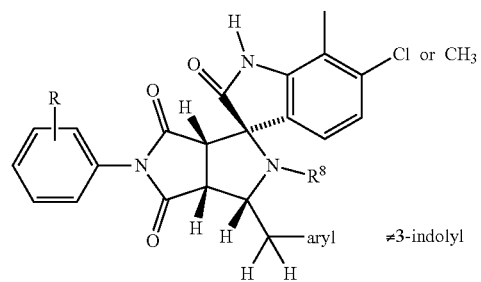

In still other embodiments $R^1$ is a substituted or unsubstituted phenyl, $R^3$, $R^6$, and $R^7$ are H, $R^4$ is methyl, $R^5$ is Cl or methyl, and $R^9$ is a substituted or unsubstituted C1-C6 alkyl, a substituted or unsubstituted C3-C7 cycloalkyl, a substituted or unsubstituted C3-C7 cycloalkenyl, a substituted or unsubstituted C2-C6 alkenyl, a substituted or unsubstituted C2-C6 alkynyl, a substituted or unsubstituted C2-C6 alkoxyalkyl, a substituted or unsubstituted C1-C6 alkoxy, a substituted or unsubstituted C1-C6 acyloxy, a substituted or unsubstituted C1-C6 carbamoyl, an unsubstituted or substituted benzyloxy, a substituted or unsubstituted C4-C6 cycloalkoxy. A diagram exemplary of these embodiments is provided below.

Formula II.6

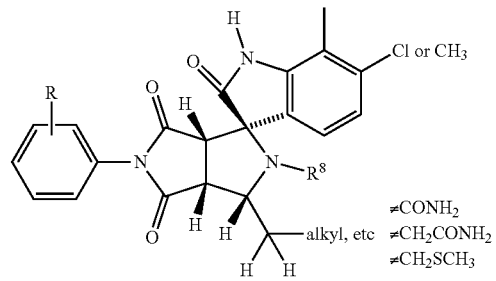

In still other embodiments $R^3$, $R^6$, and $R^7$ are H, $R^4$ is methyl, $R^5$ is Cl and $R^9$ is a substituted or unsubstituted phenyl and $R^1$ is C3-C8 alkyl, C3-C8 cycloalkyl, C3-C8 alkenyl, C3-C8 alkynyl, C3-C8 alkynyl, or C3-C8 alkoxylalkyl. A diagram exemplary of these embodiments is provided below.

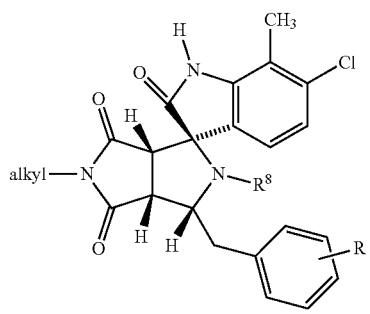

Formula II.7

In still other embodiments R¹ is a phenyl, R³, R⁶, R⁷, and R⁸ are H, R⁴ is methyl, R⁵ is Cl, and R⁹ phenyl. A diagram exemplary of these embodiments is provided below.

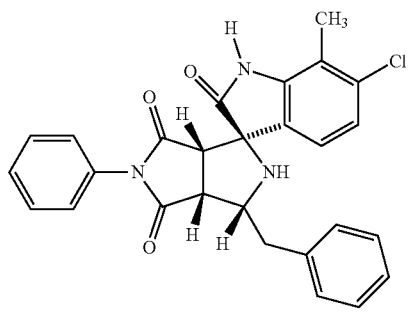

Formula II.8

In still other embodiments R¹ is a cycloheptyl, R³, R⁶, R⁷, and R⁸ are H, R⁴ is methyl, R⁵ is Cl, and R⁹ phenyl. A diagram exemplary of these embodiments is provided below.

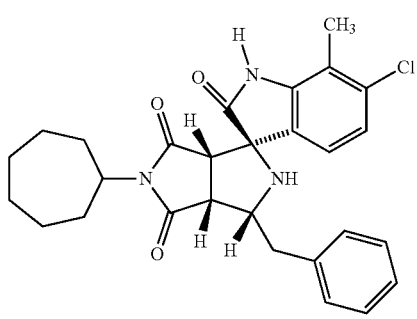

Formula II.9

It will be understood that any of the compounds in accordance with embodiments may exist in either enantiomeric form or as mixtures of enantiomers, solvates (including hydrates), tautomers, isotopic substitutions, and mixtures thereof, and are contemplated in the compounds presented.

Embodiments can also be included in/relate to pharmaceutically acceptable salts. A "pharmaceutically acceptable salt" retains the desirable biological activity of the compound without undesired toxicological effects. Salts can be salts with a suitable acid, including, but not limited to, hydrochloric acid, hydrobromic acid, sulfuric acid, phosphoric acid, nitric acid and the like; acetic acid, oxalic acid, tartaric acid, succinic acid, malic acid, benzoic acid, pamoic acid, alginic acid, methanesulfonic acid, naphthalenesulphonic acid, and the like. Also, incorporated cations can include ammonium, sodium, potassium, lithium, zinc, copper, barium, bismuth, calcium, and the like; or organic cations such as tetraalkylammonium and trialkylammonium cations. Also useful are combinations of acidic and cationic salts. Included are salts of other acids and/or cations, such as salts with trifluoroacetic acid, chloroacetic acid, and trichloroacetic acid.

Method of Action

Embodiments can also be understood with respect to the method of action. In many embodiments therapeutic compounds in accordance with embodiments function by inhibiting Cdr1, as described in greater detail in the Exemplary Embodiments, below.

Formulations

In other embodiments, the small molecule spirocyclic compounds and analogues are formulated into a therapeutic medicament for treatment of disorders, such as, for example, fungal or microbial infections particularly associated with eukaryotic cells either alone or in combination with antifungal or antimicrobial drugs, including azole drugs such as fluconazole. In such embodiments, the modes of administration for the therapeutics include, but are not limited to, oral, topical, transdermal, transmucosal (e.g., sublingual, nasal, vaginal or rectal), or parenteral (e.g., subcutaneous, intramuscular, intravenous, bolus or continuous infusion). The actual amount of drug needed will depend on factors such as the size, age and severity of disease in the afflicted individual. The actual amount of drug needed will also depend on the effective inhibitory concentration ranges of the various spirocylic compounds and analogues. Different analogues have different effective inhibitory concentration ranges, as shown and described in greater detail in Tables 1 to 4 and FIGS. 8 and 10, below.

Embodiments of therapeutics may be administered at dosages and for periods of time effective to reduce, ameliorate or eliminate the symptoms of diseases or pathological conditions susceptible to such treatment, such as, for example, fungal infections caused by *Candida albicans, Candida glabrata, Cryptococcus neoformans, Aspergillus fumigatus*, or other fungal species susceptible to Cdr1 inhibition.

For example, in embodiments where eukaryotic cells are implicated, using various embodiments of the spirocyclic small molecule compounds may be used in combination with an antifungal drug against pathogenic fungi. Alternatively, the therapeutics may be administered against a pathogenic microorganism in conjunction with an antimicrobial drug. Any suitable antifungal or antimicrobial drug may be used in conjunction with the spirocyclic compounds. In many embodiments the antifungals are selected from the azoles including: triazoles: albaconazole, efinaconazole, itraconazole, fluconazole, terconazole, voriconazole, posaconazole, epoxiconazole, isavuconazole, ravuconazole, phosravuconazole; and imidazoles: clotrimazole, ketoconazole, bifonazole, butoconazole, econazole, fenticonazole, isoconazole, luliconazole, miconazole, omoconazole, oxiconazole, sertaconazole, sulconazole, tioconazole. In many other embodiments the antifungals are selected from: thiazoles: abafungin; naphthylmethylamines: butenafine, naftifine, terbinafine; and morpholines: amorolfine, fenpropimorph, dodemorph, tridemorph; flucytosine; tolnaftate; griseofulvin; cicloprimox; FK506; and cyclosporine.

Dose regimens may be adjusted for purposes of improving the therapeutic or prophylactic response of the compound. For example, several divided doses may be administered daily, one dose, or cyclic administration of the compounds to achieve the desired therapeutic result. A single spirocyclic small molecule compound may be administered, or combinations of various spirocyclic small molecule compounds in combination with one or more azole drugs may also be administered.

It is also possible to add agents that improve the solubility of these compounds. For example, the claimed compounds can be formulated with one or more adjuvants and/or pharmaceutically acceptable carriers according to the selected route of administration. For oral applications, gelatin, flavoring agents, or coating material can be added. In general, for solutions or emulsions, carriers may include aqueous or alcoholic/aqueous solutions, emulsions or suspensions, including saline and buffered media. Parenteral vehicles can include sodium chloride and potassium chloride, among others. In addition, intravenous vehicles can include fluid and nutrient replenishers, electrolyte replenishers and the like.

Preservatives and other additives, like antimicrobial, antioxidant, chelating agents, and inert gases, can also be present. (See generally, Remington's Pharmaceutical Sciences, 16th Edition, Mack, (1980), the disclosure of which is incorporated herein by reference.)

Exemplary Embodiments

Biological data supports the use of the aforementioned spirocyclic small compounds in a variety of embodiments to treat fungal infections. Above, are described embodiments incorporating small molecule compounds, medicaments, and as part of treatment regimes. Previous studies have established that some small compounds can work synergistically with azole drugs to enhance their antifungal effect. It is noted that embodiments of the spirocyclic compounds in accordance with the disclosure dramatically increase the potency of azole drugs such as fluconazole in the treatment of fungal infections such as *C. albicans*, thereby reducing the dosage needed for treatment and reducing the likelihood of deleterious side effects. Accordingly, embodiments using these compounds to treat various fungal infections avoid the pitfalls associated with prior approaches. As will be discussed, data supports the proposition that small molecule spirocyclic embodiments according to the disclosure are superior to existing synergistic azole compounds and related treatment methods.

The expected therapeutic efficacy of the spirocyclic small molecule embodiments stems from their demonstrated biological activity in preliminary studies using *C. albicans*, *Candida glabrata*, and *Cyrptococcus neoformans*. As discussed below, minor chemical and structural modifications, including changes to substituents, may have an effect on spirocyclic small molecule activity. The most preferred embodiments show therapeutic advantages over the previously known spirocyclic control compounds.

Synthetic Materials and Methods

Synthesis Overview: Many of the spiroindolinone compounds according to embodiments (FIG. 3b) can be directly synthesized from isatin, maleimides, and acyclic amino acids using a stereoselective one-pot, 3-component reaction (Pavlovskaya, T. L., et al. *Chem. Heterocycl. Compd.* 2013, 49, 882-896). However, the previously published one-pot reaction for synthesis of spiroindolinones from isatins, maleimides, and cyclic amino acids (the five-membered ring amino acid proline; Azizian, J., et al. *Synth. Commun.* 2001, 31, 2727-2733 and Rehn, S., et al. *Eur. J. Org. Chem.* 2004, 413-418) affords spiroindolinones with a relative stereochemistry different from that of FIG. 2b (where N—Y—X is part of a five-membered ring). The previously published route (Ardill, H., et al. *Tetrahedron* 1990, 46, 6433-6448) for synthesis of spiroindolinones related to FIG. 2a (where N—Y—X is part of a six-membered ring) generates a mixture of diastereomers, disfavoring stereoisomer depicted in FIG. 2b. Thus, spiroindolinones like those in FIG. 2b, with a relative stereochemistry that is correlated with potent antifungal synergy, could not be efficiently synthesized using methods known in the prior art.

Now a stereoselective one-pot, 3-component synthesis of spiroindolinones (FIG. 2b and Formula I where N—Y—X is part of a six-membered ring) from isatins, maleimides, and six-membered ring amino acids is provided in accordance with embodiments. Another aspect according to embodiments is that sidechain-protected amino acids can be used in the three-component, one-pot synthesis of spiroindolinones. The protecting groups can be removed using standard methods and the spiroindolinones can be further functionalized by acylation, sulfonylation, phosphorylation, and related reactions.

Synthesis of Spiroindolinones (Formula II, FIG. 3b)

Figure 5:
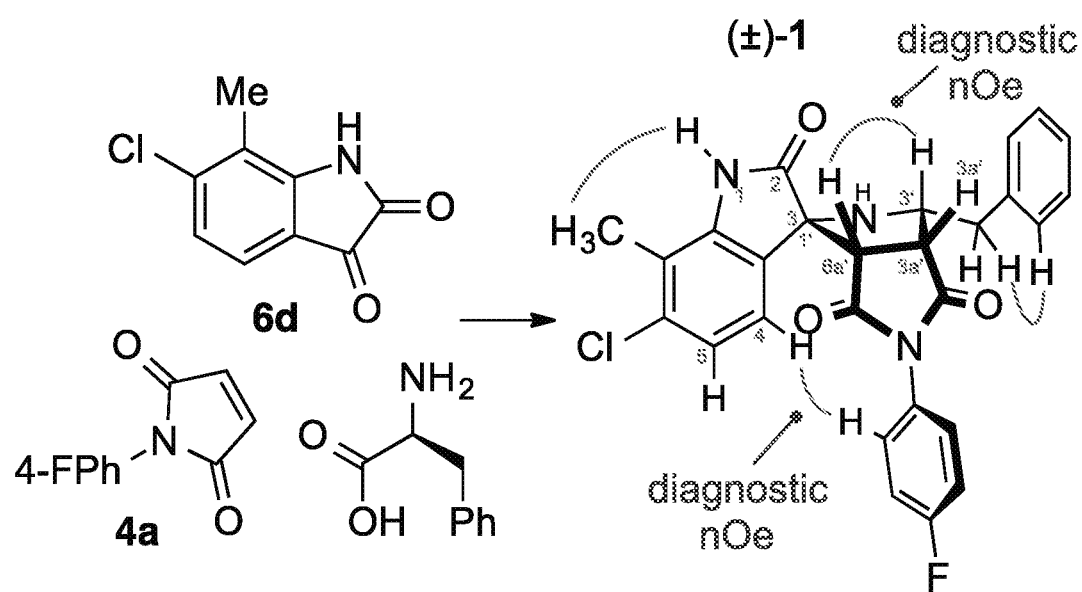
FIG. 5 provides a reaction pathway for the production of therapeutic small molecule analogues in accordance with various embodiments of the invention.

Spiroindolinones 1-8 (FIG. 6) related to Formula II and FIG. 3b are readily accessible through one-pot three-component reactions of isatins, maleimides and acyclic amino acids. (See, e.g., Pavlovskaya, T. L., et al. *Chem. Heterocycl. Compd.* 2013, 49, 882-896) In particular the reaction of 6-chloro-7-methylindoline-2,3-dione, L-phenylalanine and N-(4-fluorophenyl)maleimide generated compound (±)-1 as a single diastereomer (FIG. 5). Compound 1 is a diastereomer of CID 6584729 from the prior art. The amino acid undergoes decarboxylation during the reaction to give an achiral reactive intermediate, so spiroindolinones 1-8 were isolated and tested as racemates. The relative stereochemistry of Compound 1 was secured through a NOESY experiment (FIG. 5) The strong nOe between protons on C3' and C6a' of the pyrrolidine ring indicate that they are on the same face and conversely that the benzyl group and succinimide ring are both on the opposing face. Furthermore, the strong nOe between the fluorophenyl proton and the proton on C4 of the indolone ring is consistent with the stereochemistry assigned to Compound 1.

Synthesis of Spirocyclic Exemplary Compound 1

Figure 4B:
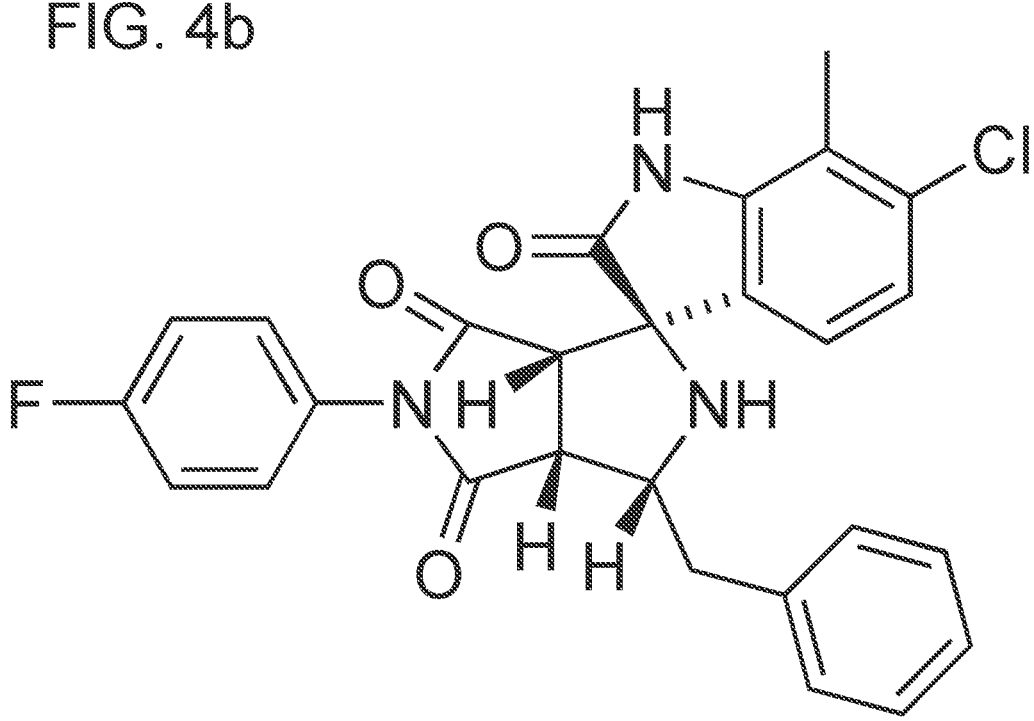

Spirocyclic compound (±)-(3R,3'R,3a'R,6a'S)-3'-benzyl-6-chloro-5'-(4-fluorophenyl)-7-methyl-2',3',3a',6a'-tetrahydro-4'H-spiro[indoline-3,1'-pyrrolo[3,4-c]pyrrole]-2,4',6'(5'H)-trione, (Compound 1, FIG. 4b), was synthesized in accordance with the following reaction.

A 100 mL round bottom flask was charged with 1-(4-fluorophenyl)-1H-pyrrole-2,5-dione (0.50 g, 2.55 mmol, 1.0 equiv), p-fluoro-N-phenylmaleimide (0.53 g, 2.8 mmol, 1.1 equiv), L-phenylalanine (0.46 g, 2.8 mmol, 1.1 equiv) and a stir bar. A 3:1 (v/v) mixture of water and methanol (11 mL) was added to the reaction flask. The content of the reaction flask was heated at reflux by immersing the reaction flask in a hot oil bath up to the level of the flask's contents. Initially a clear solution was obtained and $CO_2$ was expelled. After few hours a cloudy solution was observed.

Upon consumption of the substituted isatin (16 h), the reaction was allowed to cool to room temperature. Next, the reaction mixture was quenched by pouring it into a mixture of ice and sat. aq. $NaHCO_3$. The resulting solid was washed thoroughly with water in Büchner funnel to afford a grey solid. The solid was then dissolved in minimum amount of $CH_2Cl_2$ and purified by flash chromatography with different combinations of EtOAc/hex to afford the racemic spiroindolinone Compound 1 as a white solid (0.93 mg, 1.9 mmol, 74%). R$_f$=0.35 (1:1 EtOAc/hex); mp 212-215° C. The $^1$H NMR chemical shifts were concentration-dependent in CDCl$_3$, particularly within the range 0.5-2 mM. $^1$H NMR (600 MHz, CDCl$_3$) δ 8.00 (s, 1H), 7.41-7.38 (m, 2H), 7.27-7.16 (m, 6H), 7.02 (d, J=8.0 Hz, 2H), 6.81 (d, J=8.5 Hz, 1H), 4.72-4.71 (m, 1H), 3.75-3.69 (m, 1H), 3.45 (dd, J=14.0, 4.0 Hz, 1H), 2.73 (dd, J=13.8, 10.5 Hz, 1H), 2.16 (s, 1H), 1.99 (s, 3H); $^{13}$C NMR (500 MHz, CDCl$_3$) δ 180.4, 175.1, 174.4, 163.4, 161.4, 140.5, 139.1, 136.2, 128.9, 128.8, 128.3, 127.6, 126.7, 124.6, 124.5, 123.5, 118.2, 116.6, 116.4, 68.2, 58.9, 51.6, 47.6, 37.9, 13.5; IR (thin film) 3201, 3065, 1710, 1696, 1623, 1601, 1510; HRMS (ESI): m/z calculated for C$_{28}$H$_{29}$ClN$_4$O$_5$Na [M+Na]$^+$ 559.1724, found 559.1743.

Synthesis of Spiroindolinones (Formula I, FIG. 2b)

When the one-pot three-component coupling was applied to the protected six-membered ring amino acid (S)—Nε-Boc-piperazine-2-carboxylic acid it generated spirocyclic piperazine Compound 9 with the relative configuration shown in FIG. 2b (Formula I) and different from the stereochemistry obtained from proline in the prior art. The relative stereochemistry of spiroindolinone 9 was secured with nOes after removal of the Boc (FIG. 6). The reaction was applied to a variety of isatins and maleimides to afford compounds 10-19 as shown in FIG. 6.

Exemplary Synthesis of Spirocyclic Compound 9 from a Cyclic Six-Membered Ring Amino Acid Spirocyclic compound (±)-tert-Butyl (3R,3a'R,3b'S,9a'S)-6-chloro-7-methyl-1',2,3'-trioxo-2'-phenyl-2',3',3a',3b',4',6',7',9a'-octahydrospiro[indoline-3,9'-pyrrolo[3',4':3,4]pyrrolo[1,2-a]pyrazine]-5'(1'H)-carboxylate,

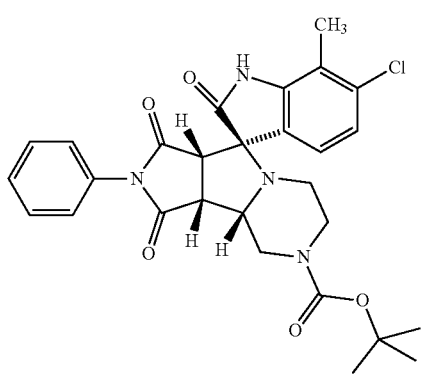

9

A 100 mL round bottom flask was charged with substituted isatin 6-chloro-7-methylindoline-2,3-dione (0.81 g, 4.1 mmol, 1.0 equiv), N-phenylmaleimide (1.1 equiv), the N$_ε$-Boc-piperazine-2-carboxylic acid (1.1 equiv) and a stir bar. A 3:1 (v/v) mixture of water and methanol was added to the reaction flask such that the concentration of isatin was 0.25 M. The reaction was heated at reflux by immersing the reaction flask in a hot oil bath at 90° C. up to the level of the flask's contents. Initially a clear solution was obtained and CO$_2$ evolution was observed. However, after a few hours the reaction mixture became cloudy. The reaction was monitored for consumption of the substituted isatin by TLC (EtOAc/hex).

Upon consumption of the substituted isatin, the reaction was cooled to room temperature. Next, the reaction mixture was quenched by pouring it into a mixture of ice and sat. aq. NaHCO$_3$. The resulting solid was washed thoroughly with water in Büchner funnel to afford a grey solid. The solid was then dissolved in minimum amount of CH$_2$Cl$_2$ and purified by flash chromatography with ethyl acetate/hexanes (1:1) to afford the racemic spiroindolinone Compound (±)-9 as a light pink solid (1.3 g, 2.5 mmol, 60%). R$_f$=0.35 (4:6 EtOAc/hexanes); mp 201-205° C.; $^1$H NMR (600 MHz, DMSO-d$_6$, 400 K) δ 10.90 (s, 1H), 7.54-7.51 (m, 2H), 7.47-7.46 (m, 1H), 7.31 (d, J=7.8 Hz, 2H), 7.06 (d, J=7.8 Hz, 1H), 6.73 (d, J=7.8 Hz, 1H), 4.31 (br s, 1H), 3.85 (t, J=7.5 Hz, 2H), 3.64-3.65 (m, 1H), 3.55 (d, J=7.8 Hz, 1H), 2.74-2.58 (m, 2H) 2.25 (app s, 4H), 2.13-2.08 (m, 1H), 1.41 (s, 9H); $^{13}$C NMR (500 MHz, DMSO-d$_6$, 313 K) δ 177.9, 174.7, 173.4, 153.6, 142.8, 134.6, 132.1, 128.9, 128.5, 126.9, 124.6, 123.2, 122.8, 117.3, 79.1, 71.7, 62.3, 58.7, 57.6, 50.4, 45.9, 44.9, 27.9, 13.7; IR (thin film) 3840, 3708, 3626, 2971, 2843, 1713, 1695, 1032; HRMS (ESI): m/z calculated for C$_{28}$H$_{29}$ClN$_4$O$_5$Na [M+Na]+559.1724, found 559.1743.

Modification Spiroindolinones (Formula II, FIG. 3b)

Figure 7:
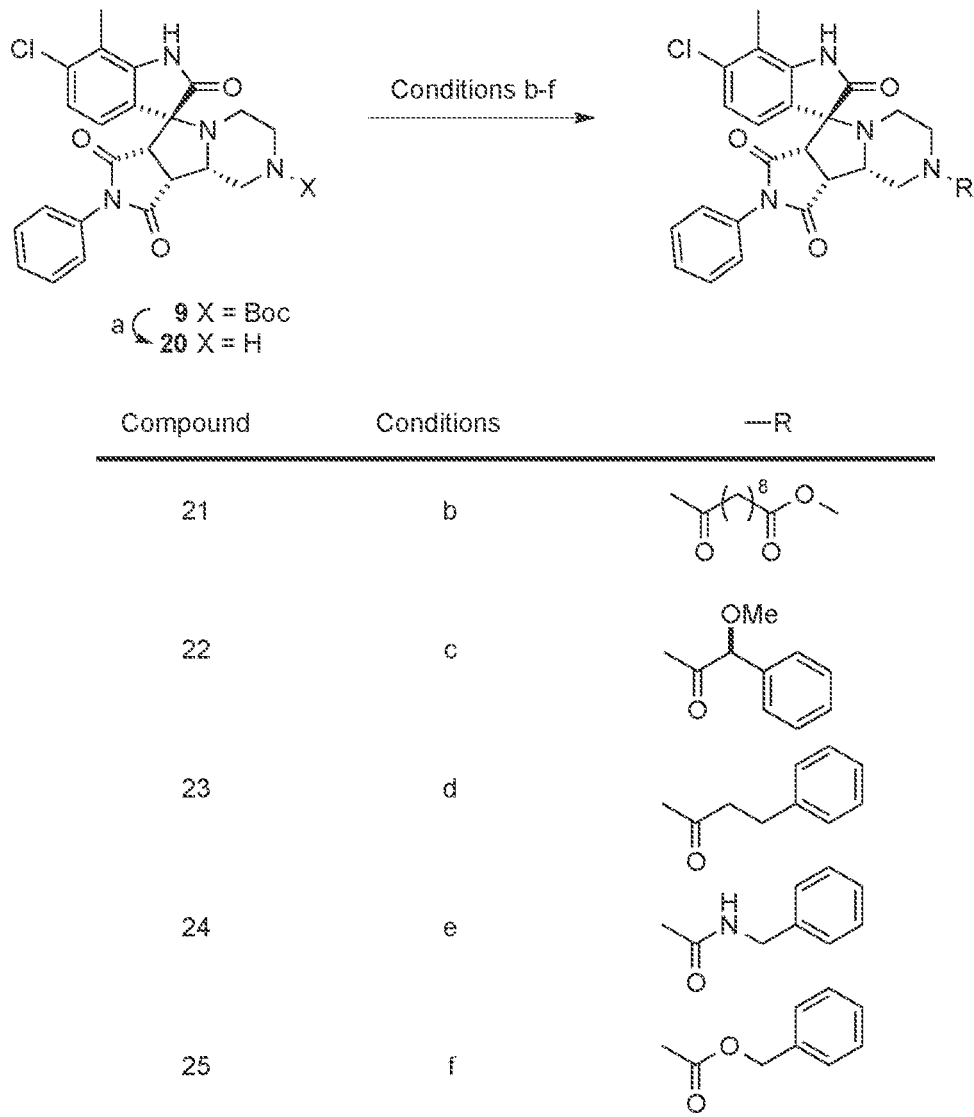
FIG. 7 provides reaction pathways for the production of therapeutic small molecule analogues incorporating pentacyclic pyrrolidines in accordance with various embodiments of the invention.

By employing amino acids protected with, for example, t-butoxycarbonyl (Boc), 9-fluorenylmethoxycarbonyl, and trifluoroacetyl, in the one-pot three-component reaction allows for deprotection and further functionalization of the spiroindolinone. For example, the Boc group was removed from the spirocyclic piperazine 9 using trifluoroacetic acid under standard conditions (1:1 trifluoroacetic acid/CH$_2$Cl$_2$, 23°) to give a 90% yield of the piperazine compound 20 (FIG. 7) which was then acylated with acid chlorides, activated carboxylic acids, isocyanates, and chloroformates using standard procedures to afford spiroindolinones 21-25 (FIG. 7).

Synthesis of Exemplary Spirocyclic Compound (±)-25

Spirocyclic compound (±)-benzyl (3R,3a'R,3b'S,9a'S)-6-chloro-7-methyl-1',2,3'-trioxo-2'-phenyl-2',3',3a',3b',4',6',7',9a'-octahydrospiro[indoline-3,9'-pyrrolo[3',4':3,4]pyrrolo[1,2-a]pyrazine]-5'(1'H)-carboxylate, (Compound (±)-25, see FIG. 7), shown below, was synthesized in accordance with the following reaction.

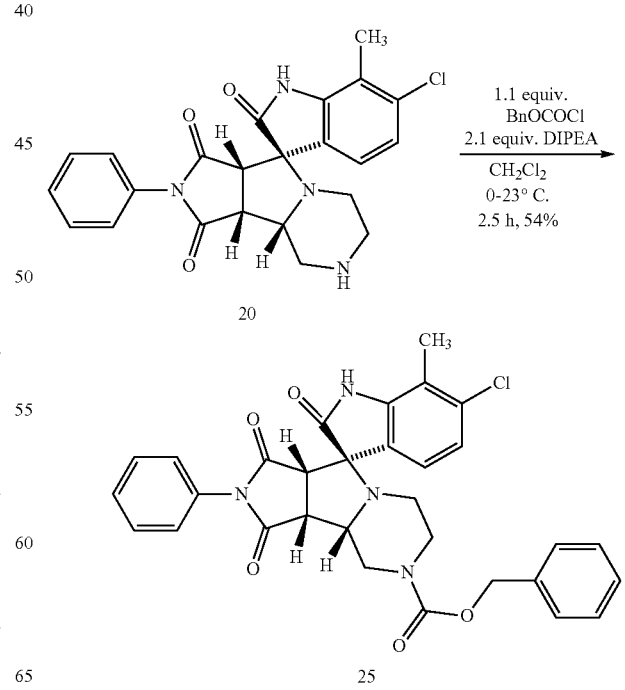

A 5 mL round bottom flask was charged with pyrrolidine Compound (±)-20 (0.20 g, 0.45 mmol, 1.0 equiv), N,N-diisopropylethylamine (0.17 mL, 0.96 mmol, 2.1 equiv) and a stir bar. The flask was fitted with a septum and purged with nitrogen. Then 0.92 mL of $CH_2Cl_2$ was added to the round bottom flask by syringe. The reaction mixture was cooled to 0° C. with an ice bath. Meanwhile another 5 mL pear-shaped flask was charged with benzyl chloroformate (0.07 mL, 0.50 mmol, 1.1 equiv) and the flask was fitted with a septum and purged with nitrogen. Then 0.34 mL of $CH_2Cl_2$ was added to the pear shaped vial containing the benzyl chloroformate and stirred for 10 min. Next the contents of the 5 mL pear shaped vial was slowly added to the 5 mL round bottom flask containing Compound 20. The ice bath was removed and the reaction mixture was allowed to stir for 2.5 h at room temperature. The reaction was monitored for consumption of Compound 28 by TLC (50:50:5 ethyl acetate/hexanes/Et3N).

Upon consumption of Compound 20, the reaction mixture was quenched with 5 mL of saturated aqueous $NaHCO_3$ and the aqueous layer was then extracted with (3×5 mL) $CH_2Cl_2$. The combined organic layers were then washed with brine and dried over $Na_2SO_4$. The resulting organic solution was concentrated under vacuum to give a yellow oil. The oil was then purified by flash chromatography with ethyl acetate/hexanes/Et$_3$N (60:40:5) to afford the pyrrolidine compound (±)-25, a white solid, (0.14 g, 0.25 mmol, 54%). $R_f$=0.81 (1:1 EtOAc/hex); mp 209-211° C.; $^1$H NMR (600 MHz, DMSO-d$_6$, 400 K) δ 10.40 (s, 1H), 7.53-7.51 (m, 2H), 7.45-7.42 (m, 1H), 7.37-7.35 (m, 6H), 7.32-7.31 (m, 1H), 7.03 (d, J=8.0 Hz, 1H), 6.80 (d, J=8.0 Hz, 1H), 5.16 (s, 2H), 4.48 (d, J=12.7 Hz, 1H), 3.99 (d, J=13.1 Hz, 1H), 3.89-3.87 (m, 1H), 3.82-3.79 (m, 1H), 3.61 (d, J=8.0 Hz, 1H), 2.91-2.86 (m, 2H), 2.78-2.75 (m, 1H), 2.34-2.25 (m, 5H); $^{13}$C NMR (500 MHz, DMSO-d$_6$) δ 178.5, 175.3, 173.9, 154.9, 143.4, 137.3, 135.2, 132.6, 129.5, 129.0, 128.9, 128.3, 128.1, 127.4, 72.3, 66.9, 58.2, 51.0, 47.2, 43.5, 30.9, 21.1, 14.3; IR (thin film) 3850, 3678, 3262, 2966, 2864, 1715, 1694, 1032; HRMS (ESI): m/z calculated for $C_{31}H_{27}ClN_4O_5Na$ [M+Na]$^+$ 593.1567, found 593.1584.

Biological Evaluation Materials And Methods

Strains and growth condition. The wild-type *Candida albicans* strains used were SC5314 and CaSS1. Cdr1 heterozygous were from Merck Sharp & Dohme Corp. Double Barcoded (DBC) library of heterozygous *Candida albicans* mutants (version 2013A). Cdr1 deficient mutant was obtained by counterselection of the GRACE library strain on 5-Fluoroorotic Acid (5-FOA) containing plate. Clinical isolated resistant *C. albicans* were from Dr. David Rogers. *Cryptococcus neoformans* var. grubii H99 (ATCC 208821) and *Candida glabrata* BG2, a fluconazole-resistant clinical isolate, were used. Yeast strains were cultured at 30° C. in synthetic complete (SC) medium containing 2% glucose.

Chemicals. Fluconazole (FLC), ketoconazole (KTC), itraconazole (ICZ), miconazol (MCZ), voriconazole (VCZ), clotrimazole (CLZ), cyclohexmide (CHX), anisomycin (ANI), thiolutin (THI), and 2-deoxy-D-glucose were purchased from Sigma-Aldrich Co. (St. Louis, Mo.). Rhodamine 6 G (R6G) is product of Thermo Fisher Scientific (Waltham, Mass.). Fluconazole was dissolved in double-distilled water; all other compounds were dissolved in dimethyl sulfoxide (DMSO).

Drug susceptibility assay. All the assays were carried out with SC medium in 24-well plates. Fresh overnight cultures were diluted 1:100 in SC medium and incubated about 4 h at 30° C. with constant shaking, then diluted again to OD600 nm=0.0625 and cells were aliquoted to 24-well plate (1 ml per well) and compounds were added along or combined with fluconazole. Plates were incubated at 30° C. for 15 h. Cell growth was measured by reading absorbance at 600 nm. The effective concentrations (EC) for selected compounds were determined using a ten-fold dilution of the compound from 30 μM to 0.003 μM with 0.25 μg/ml FLC measured by optical density. EC50 values were calculated by nonlinear regression curve fit of log (concentration) versus the % cell growth.

Whole genome Haploinsufficiency Profiling (HIP) analysis. Haplo-Insufficiency Profiling (HIP) with the Double BarCoded (DBC) library was used. A pool of 5,470 heterozygous deletion *C. albicans* strains constructed by Merck, to identify potential targets for the azole-synergizer, Compound 1. The collection, obtained from Merck Sharp & Dohme Corp in 96-well plates, were transferred to YPD (2% peptone, 1% yeast extract, and 2% glucose) agar plates and grown at 30° C. for 72 h. All colonies were collected from plates and pooled in SC medium, add glycerol to 15% and adjust to the final concentration of 50 OD600 nm per milliliter, store in aliquot at −80° C.

Stock pools were diluted into SC medium to an OD600 nm of 0.0875 and drug treatments were performed in a 1 ml SC medium in 24-well plates. The appropriate drug treatment concentrations were determined before screening. Cells were grown at 30° C. for 15 h, then diluted back to OD600 nm=0.0875 and grown for a further 23 h with fresh compounds. At the end point, cells were harvest and genomic DNA were extracted by using smash and grab protocol. Final genomic DNA concentration was adjusted to 50 ng/μl and 4 μl was used for PCR amplifications of the unique molecular barcodes present in each strain in 50 μl volume. The primers used were as follow:

```
UP-tag: Forward:
                                       (SEQ. ID #1)
5'-CAAGCAGAAGACGGCATACGAGCTCTTCCGATCTGATGTCCACGAGG TCTCT-3'
and, Reverse:
                                       (SEQ. ID #2)
5'-AATGATACGGCGACCACCGAGATCTACACTCTTTCCCTACACGACGC

TCTTCCGATCTNNNNNNNGTCGACCTGCAGCGTACG-3';

DOWN-tag: Forward:
                                       (SEQ. ID #3)
5'-CAAGCAGAAGACGGCATACGAGCTCTTCCGATCTCGAGCTCGAATTC ATCGAT-3'
And, Reverse:
                                       (SEQ. ID #4)
5'-AATGATACGGCGACCACCGAGATCTACACTCTTTCCCTACACGACGC

TCTTCCGATCTNNNNNNNCGGTGTCGGTCTCGTAG-3'.
```

The variable 7-mer indexing tag (italics N) used in multiplexing read-out was according to M. Meyer and M. Kircher (cited below). The PCR condition was as following: 94° C. 3 min; 94° C. 30 s, 55° C. 30 s, 72° C. 30 s (24 cycles); 72° C. 3 min, hold at 4° C. The 155-bp PCR products were checked on a 2% agarose gel. Similar amount of PCR products from different treatments were pooled together and purified by using Qiagen PCR cleanup columns (Qiagen, Germany). Sequencing was performed on Illumina Hi-Seq 2500 instrument using standard Illumina primer:

(SEQ. ID #5)
5'-ACACTCTTTCCCTACACGACGCTCTTCCGATCT-3'.

Bioinformatics analysis of HIP. Sequencing reads were first separated by their experimental tags into treatments and then filtered by UPTAG or DNTAG. Among the reads mapped with experimental tags, more than 95% can be filtered exclusively by UPTAG or DNTAGs. Filtered reads were mapped to an artificial genome containing each individual gene in the library identified by UPTAG or DNTAG using bowtie 1.0.

Read counts per gene were calculated using a weighted arithmetic mean of mapped UPTAG and DNTAG read counts. This was done to increase robustness in cases where one count is unexpectedly low due to experimental artifacts. Genes with <50 weighted reads mapped in the control conditions were omitted from further analyses. Weighted means were then quantile normalized with respect to the control conditions using R to adjust for the difference in total reads between different treatments.

Pairwise Bayesian regularized t-tests were performed between each treatment and the corresponding control condition using Cyber-T: secondary drugs in addition to FLC were compared to treatment of FLC alone; single treatments were compared to no treatment. In each pairwise analysis, normalized reads were processed using Variance Stabilizing Normalization (VSN) and values in similar regimes were used for regularization to obtain Bayes t-statistics in an attempt to reduce the effect of noise. Finally fitness was quantified by Bayes t-statistics and shown in plots.

Manually Screening. Of the DBC library was carried out in 96-well flat bottom plates. Briefly, BDC library grown in YPD agar were transferred to SC medium in 96-well flat bottom plates with a 96-well pin tool and grown overnight at 30° C. Cell cultures were diluted 1:800 in fresh SC medium with or without compounds and incubated at 30° C. for 24 h. Cell growth was measured with Tecan GENios Plus microplate reader (Tecan, Switzerland).

Efflux of Rhodamine 6 G. Efflux of R6G was measured generally base on a method described previously by Shukla (cited below). Briefly, C. albicans SC5314 grown overnight at 30° C. in SC medium were transferred to fresh SC medium with a 1:50 dilution and grown at 30° C. with constant shaking for about 5 h. Cells were then pelleted, washed twice with phosphate-buffered saline (PBS), and resuspended in PBS as about 3 OD600 nm. The cells were then deenergized for 45 min in 10 µM 2-deoxy-D-glucose. The cells were pelleted, washed and resuspended in PBS as 3 OD600 nm, to which compounds (30 µM or noted) and R6G (10 µM) were added successively and incubated at 30° C. for 40 min. Cells were collected, washed and resuspended in PBS with or without compounds and incubated at 30° C. Two percent glucose was added at time point 20 min to initiate the energy-dependent efflux. Samples were taken out every 10 min and the absorption of the supernatant was detected at 527 nm.

Dose-Response Curves for Test Compounds Against C. albicans with and without Fluconazole C. albicans was grown in SC medium overnight and then diluted to an effective OD600 of 0.0625. Serial ten-fold dilutions of the test compounds (0.15-1500 µM) were prepared in DMSO in 1.5 mL Eppendorf tubes. To each well in columns B-D (triplicate analysis) of a 24-well Palcon plate was added 2.5 µL of fluconazole solution. To each well in all four columns of the plate was added 1 mL of cells in SC medium such that the column A served as a control to assess the $EC_{50}$ of the compound in the absence of fluconazole. Then to each well in rows 2-5 was added a solution of the compound in DMSO (2 µL each) such that the final solution fluconazole in columns 2-4 was 0.25 µg/mL and the concentration of compound in each row varied from 0.003 µM to 30 µM. The plates were incubated in a rotary shaker/incubator at 30° C. for 16 h. The contents of each well was resuspended with a micropipettor and a 20 µL aliquot was added to a polystyrene cuvette and diluted with 680 µL of deionized water. The suspension was triturated again immediately before measuring the absorbance at 600 nm (OD600) for cell densities. $EC_{50}$ values were determined by fitting to the Hill equation using the Excel-based tool ED50PLUS v1.0 (Mario H. Vargas) or using Mathematica. Similar procedures were used for Candida glabrata and Cryptococcus neoformans.

Determination of $FIC_{90}$s with a Checkerboard Assay

Checkerboard assays were carried out using four 24-well plates. The results on each plate were normalized by duplication of one row and one column with a row and column on another plate. C. albicans was grown in SC medium overnight and then diluted to an effective $OD_{600}$ of 0.0625. Serial ten-fold dilutions of the test compounds (150 mM) were prepared in DMSO in 1.5 mL Eppendorf tubes. Serial two-fold dilutions of the fluconazole (6.53 µM) were prepared in sterile water in 1.5 mL Eppendorf tubes. To each well was added 2 µL of a stock solution of compound in DMSO and 2.5 µL of a stock solution of fluconazole in water. Concentrations of compound in rows 1-11 varied from 300 µM to 0.0003 nM; the last row 12 contained no compound. Concentrations of fluconazole in each column B-H varied from 0.0625 to 2 µM; the first column A contained no fluconazole. The plates were incubated in a rotary shaker/incubator at 30° C. for 16 h. The contents of each well was resuspended with a micropipettor and a 20 µL aliquot was added to a polystyrene cuvette and diluted with 680 µL of deionized water. The suspension was triturated again immediately before measuring the absorbance at 600 nm. The $MIC_{90}$ values were determined as the lowest concentrations of the drugs (alone or in combination) that inhibited fungal growth by 90% compared with that of the drug-free wells.

Molecular Properties

Physicochemical properties were calculated from the SMILES representation of Compound 25 using the Molinspiration Property Calculation Service.

Summary of Biological Studies

Mechanism of Activity

Figure 8A:
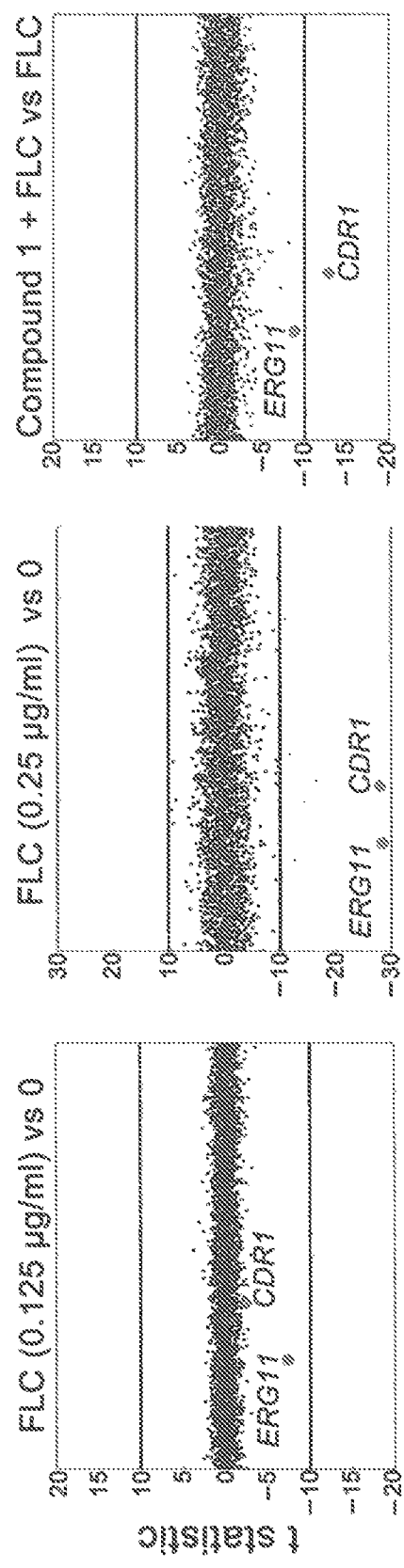
FIG. 8A provides data plots showing whole genome Haploinsufficiency Profiling (HIP) results.

Some spiroindolinones are potent enhancers of fluconazole against Candida albicans. To identify potential targets of the spiroindolinones, a chemical genomic approach was used. Specifically, Haplo-Insufficiency Profiling (HIP) with the Double BarCoded (DBC) library, a pool of 5,470 heterozygous deletion C. albicans strains constructed by Merck was used. The heterozygous deletion of the target gene of a compound is expected to be hypersensitive to that compound and its relative abundance should decrease after growth in the presence of the compound. In the HIP profiling, cdr1/CDR1 emerged as the only mutant that showed a significant change in abundance in pairwise comparisons of Compound 1+FLC vs. FLC, as shown in FIG. 8A. Specifically, in this study fitness as measured by significance of change, indicated by t statistic between treatment groups over non-treatment group is plotted. Each panel shows the distribution of t statistics with the indicated treatments. 0.05 µM of Compound 1 in the presence of 0.125 µg/ml FLC were used as treatments and compared to 0.125 µg/ml FLC.

The x-axis is genes ordered alphabetically by names. Erg11 and Cdr1 are significant targets in FLC 0.25 µg/ml vs. no-drug control. Cdr1 is the common significant target in test compound with 0.125 µg/ml FLC vs. 0.125 µg/ml FLC.

Figure 8B:
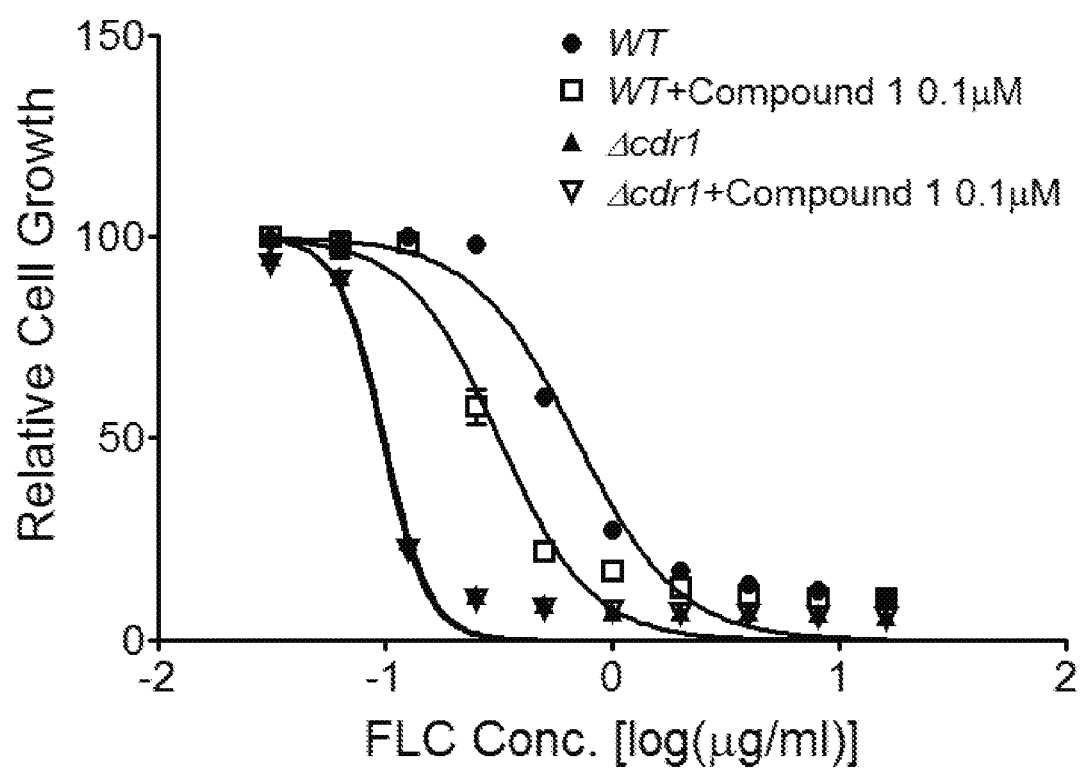
FIG. 8B provides data plots showing dose-dependent growth inhibition by Compound 1 & 25.

It was further confirmed that the effect the spiroindolinone as an azole-synergizer was significantly enhanced in the cdr1/CDR1 heterozygous mutant but blocked in the cdr1/cdr1 deletion strain, as shown in FIG. 8B. The genetic results suggest that the spiroindolinone may function by inhibiting Cdr1 directly as no other mutants were identified from the HIP profiling. Small number of outliers in the HIP profiling indicates few off-targets for the compound. To avoid missing genes due to the bias of PCR and sequencing, a manual screening of the DBC library with Compound 1 and FLC in 96 well plates was also carried out. Again, the cdr1/CDR1 heterozygous showed the highest sensitivity to the spiroindolinone, and the cdr1/cdr1 was the only homozygous mutant that blocked the synergy effect of the spiroindolinone.

Figure 8C:
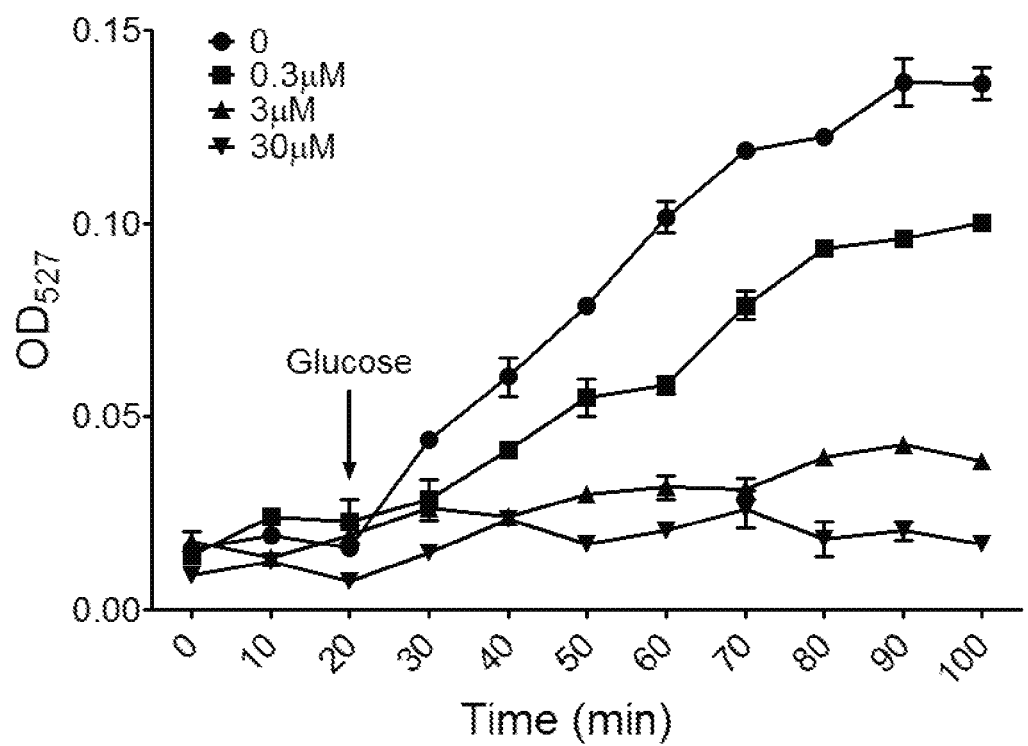
FIG. 8C provides data plots showing the effect of Compound 1 on R6G efflux.

To further determine if the spiroindolinone functions by inhibiting Cdr1, the activity of efflux pumps was determined by monitoring the efflux of R6G, a fluorescent compound that is used for Cdr1 efflux assay in *C. albicans*. Specifically, *C. albicans* wild type strain SC5314 was incubated either with R6G (10 µM) alone or with R6G plus Compound 1 (0.3, 3 and 30 µM). The energy-dependent R6G efflux was initiated by adding 2% glucose. Extracellular R6G concentrations were quantified by measuring the absorbance of the supernatant at 527 nm. Compound-free control (labeled as 0) was included. As shown in FIG. 8C, the energy dependent efflux of R6G was almost totally inhibited by the spiroindolinone.

Figure 9:
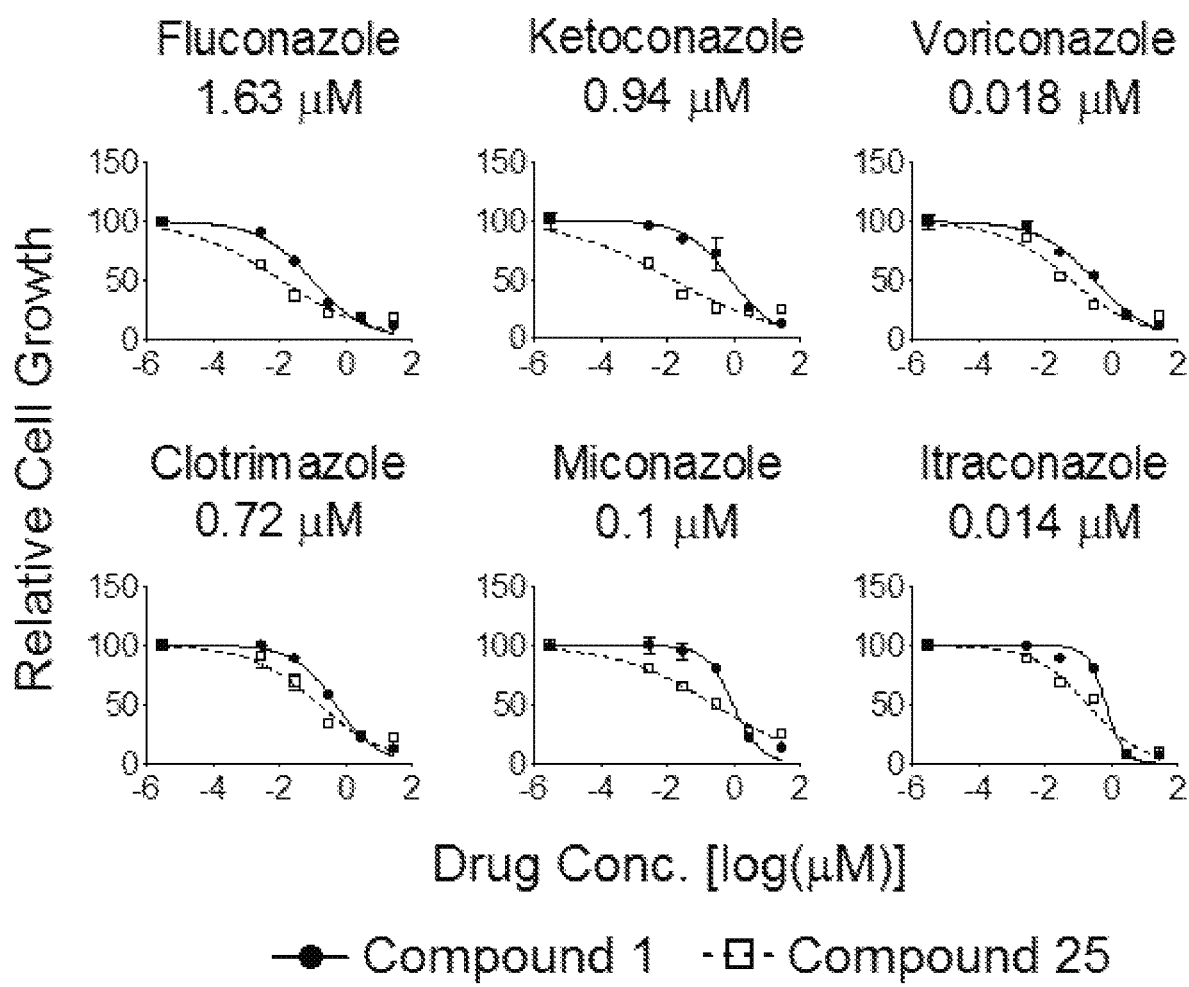
FIG. 9 provides data plots shown dose-dependent growth inhibition by Compounds 1 and 25.

Compound 1 was also studied to determine if it can synergize with all azole antifungals and non-azole drugs that are known Cdr1 substrates. It was found that the spiroindolinone could increase the susceptibility of *C. albicans* to all azole antifungals tested, as shown in FIG. 9. It could also enhance the growth inhibitory activity of cycloheximide, an inhibitor of protein biosynthesis and a substrate of the Cdr1 efflux pump. This result further confirms the function of the spiroindolinone as a Cdr1 inhibitor. The results of FIG. 9 are summarized in Table 1, below. The effective concentrations of the spiroindolinone used are at nM levels, much lower than that of substrates (azoles for example), therefore ruling out competitive inhibition as the mechanism. Compound 1 did not enhance the growth inhibitory activity of thiolutin, a substrate of the major facilitator superfamily transporter Mdr1. With further study it is possible to determine drug-target interaction sites on Cdr1.

TABLE 1

Activity of Sprioindolinones with Azole Antifungal Drugs

| c | [azole] (µg/mL) | $EC_{50}$ (µM) | $MIC_{50}$ (µM) |
|---|---|---|---|
| Compound 1 | | | |
| miconazole | 0.031 | 0.99 | 3.6 |
| ketoconazole | 0.289 | 0.83 | 7.4 |
| clotrimazole | 0.221 | 0.50 | 3.7 |
| fluconazole | 0.500 | 0.10 | 1.3 |
| itraconazole | 0.004 | 0.70 | 1.7 |
| vorizonazole | 0.006 | 0.31 | 4.5 |
| Compound 25 | | | |
| miconazole | 0.031 | 0.24 | 25 |
| ketoconazole | 0.289 | 0.014 | 2.3 |
| clotrimazole | 0.221 | 0.15 | 4.1 |
| fluconazole | 0.500 | 0.011 | 0.84 |
| itraconazole | 0.004 | 0.19 | 2.5 |
| vorizonazole | 0.006 | 0.062 | 1.9 |
| isavuconazole | 0.0006 | 0.004 | 0.11 |

Structure-Activity Relationships

Previous spirocyclic compounds have been reported to enhance the effect of fluconazole against the partially resistant clinical isolate of *C. albicans* CaCi-8 at relatively high concentrations of $EC_{50}$ 0.12 µM. (See, National Center for Biotechnology Information. PubChem BioAssay Database; AID=2423, Source=Broad Institute.) The antifungal potency of the new spiroindolinones in combination with fluconazole (0.25 µg/mL) were tested against a susceptible strain (HLY4123) derived from a commonly used laboratory strain of *C. albicans*. As shown in FIG. 10, the activity of the compounds varies significantly depending on the chemical structure of the spiroindolinone. The structure-activity relationships favor two groups of compounds corresponding to Formula I and Formula II. The original Compound 1 has an $EC_{50}$ of 0.011 µM. Comparing compounds 2-4, activity is better when $R^9$ is an aromatic group. Compound 8 derived where $R^4$ is methyl, $R^5$ is chloro and $R^1$ is a phenyl group was exceedingly potent with an $EC_{50}$ of 1 nM.

Figure 11:
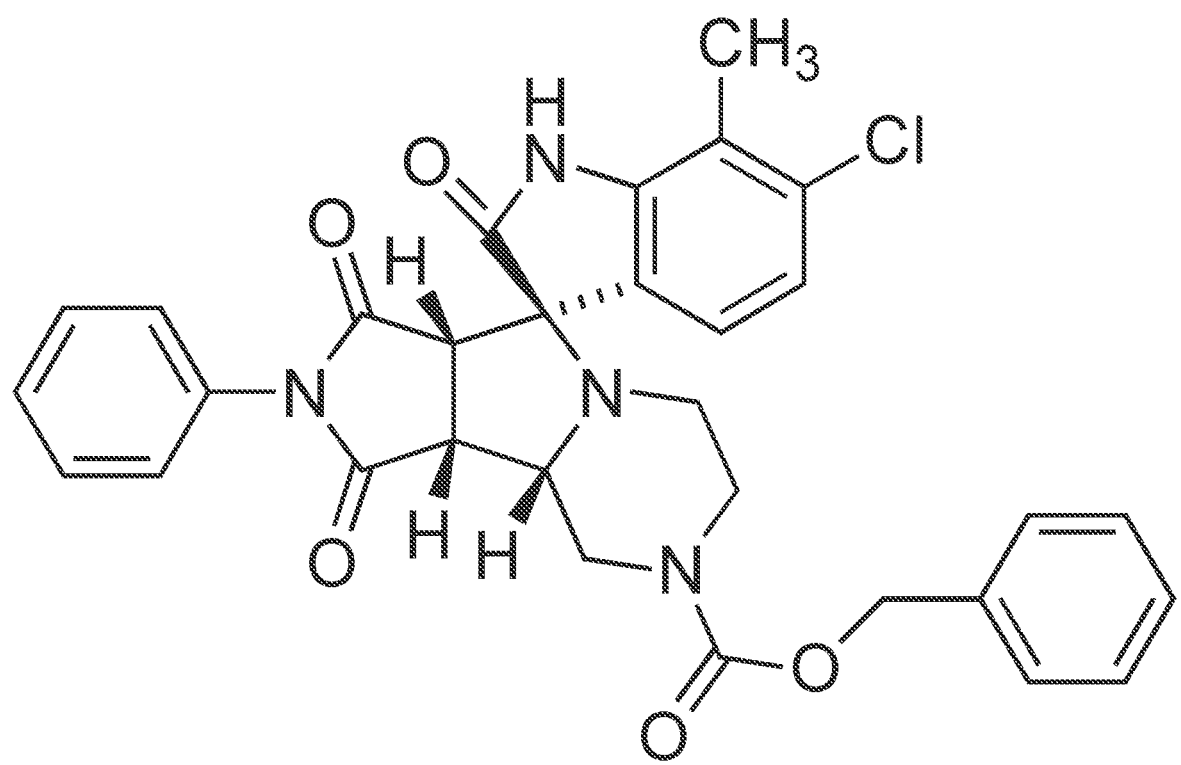
FIG. 11 provides one of the enantiomers of the molecular structure of compound 25 in accordance with the invention.

Compound 9 was highly active with an $EC_{50}$ of 5.6 nM. N-Benzylsuccinimide derivatives (Compounds 13, 14, and 17) were not highly active. The substituents on the indolone ring were still important, even with the pentacyclic piperazine core (Compounds 12, 15, 16, 18, 19). The unacylated piperazine 20 had low activity. The carboxyl oxygen of the carbamate moiety in compound 9 shows some degree of impact on the potency; because carbamate Compounds 9 and 25 were more potent than amide Compounds 21 and 22. Even more revealing, the isosteric amide Compound 23 and urea Compound 24 were two and three orders of magnitude less active, respectively, than benzyloxycarbamate Compound 25. Ultimately, benzyloxycarbamate Compound 25 (FIG. 11) proved to be exquisitely active in improving the efficacy of fluconazole with an $EC_{50}$ of 300 pM.

Activity Against Resistant Cell Lines

A variety of resistant clinical isolates of *C. albicans* were screened with 64 µg/ml fluconazole and Compound 25 at a single dose (3 µM) in a broth microdilution assay (see Table 2, below). (Flowers, S. A., et al. *Eukaryotic Cell* 2012, 11, 1289-1299.) The strains grow at dramatically different rates. The published fluconazole MICs for these isolates convey the level of resistance. Strains for which growth in the presence of Compound 25 and fluconazole was less than 25% of growth in the presence of fluconazole alone (*C. albicans* clinical isolates 17, 23, 26, 33, 36, and 45) were selected for determination of $EC_{50}$s. Compound 25 was particularly active against clinical isolates 17, 26 and 36 and exhibited good activity against the highly resistant isolate 45.

TABLE 2

| Clinical Isolate[a] | $MIC_{Flc}$[a] | Growth $(OD_{600})$[b] +Fluc[c] | +Cpd25[d] + Fluc[c] | Potency Cpd 25 $EC_{50}$[c] |
|---|---|---|---|---|
| 15 | 16 | 5.58 | 2.64 | nd |
| 16 | 16 | 0.64 | 0.43 | nd |
| 17 | 32 | 3.96 | 0.79 | 5 nM |
| 21 | 32 | 6.46 | 2.02 | nd |
| 22 | 32 | 3.27 | 1.28 | nd |
| 23 | 32 | 6.77 | 0.60 | 53 nM |
| 25 | 32 | 2.90 | 1.59 | nd |
| 26 | 32 | 6.44 | 0.83 | 2 nM |
| 30 | 64 | 9.40 | 5.38 | nd |
| 33 | 64 | 7.38 | 0.88 | 11 nM |
| 36 | 64 | 5.08 | 1.07 | 5 nM |
| 41 | 128 | 9.47 | 6.52 | nd |
| 45 | 128 | 9.17 | 1.03 | 16 nM |
| 49 | 256 | 11.31 | 11.29 | nd |

[a]Taken from Flowers, et al, J. Antimicrob. Chemother. 2004, 54, 854-869.
[b]Growth of susceptible strain HLY4123 measured after 16 h in SC at 30° C.
[c][fluconazole] = 64 μg/mL.
[d][compound 25] = 3 μM.

A checkerboard assay was used to determine the fractional inhibitory concentrations for Compound 25 and fluconazole against the fluconazole-susceptible strain (HLY4123) and two fluconazole-resistant clinical isolates 26 and 45 (Table 3). In all of the strains tested, the FIC index was below 0.5, fitting the classical definition of synergy. (Cuenca-Estrella, M., J. Antimicrob. Chemother. 2004, 54, 854-869.) Compound 25 alone did not have measurable toxicity against any of the strains at the solubility limit (between 30 and 300 μM). In the strains tested, fluconazole dramatically enhances the activity of Compound 25 against C. albicans. Conversely Compound 25 makes fluconazole more potent against those same strains but the effect is less dramatic.

TABLE 3

| Strain | $MIC_{cpd}$ | $MIC_{cpd}$ (+Flc) | $MIC_{Flc}$ | $MIC_{Flc}$ (+cpd) | FICI |
|---|---|---|---|---|---|
| HLY4123 | >300 | 0.03 | 0.5 | 0.125 | 0.25 |
| 26 | >30 | 0.3 | 836 | 105 | 0.14 |
| 45 | >30 | 0.03 | 836 | 105 | 0.13 |

$MIC_{90}$ measured in μM

Greater than 90% inhibition of C. albicans sterol α-demethylase (a.k.a. Erg11 or CYP51) would be expected at ten times the $K_i$ for fluconazole; the $K_i$ has been determined to be 0.03 μM. (Lamb, D. C., et al. J. Biol. Chem. 1997, 272, 5682-5688; and Warrilow, A. G., et al. Antimicrob. Agents Chemother. 2013, 57, 1352-1360.) When Compound 25 is present at 300 nM in the susceptible strain, the $MIC_{90}$ for fluconazole is reduced from 0.5 μM to 0.125 μM, consistent with the theoretical limit for fluconazole potency of around 0.3 μM.

Figure 12:
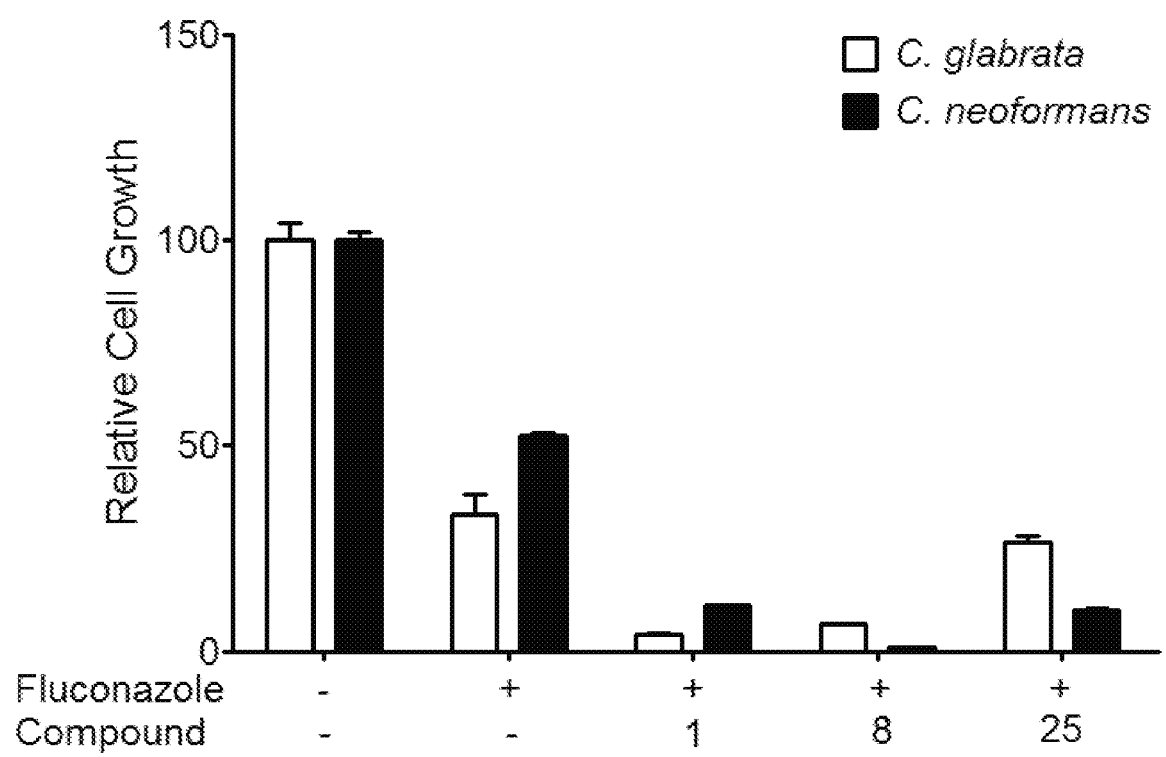
FIG. 12 provides a data plots for the growth inhibition of *Candida glabrata* and *Cryptococcus neoformans* by spiroindolinones+FLC vs. FLC alone.

Because fungal drug-efflux ABC transporters are conserved, Cdr1 inhibitors that target the conserved regions of the pumps are expected to inhibit the drug efflux pumps in all fungi including C. albicans. In support of this notion, preliminary experiments showed that several spiroindolinones are active azole-synergizers against not only Candida albicans, but also Candida glabrata and Cryptococcus neoformans, as shown in FIG. 12. The levels of fluconazole-synergy activities against these fungi are different for different spiroindolinones, as summarized in Table 4 ($EC_{50}$s for spiroindolinones in combination with fluconazole) below. A number of structure-activity trends are revealed in the data for compounds related to formula II: i) a comparison of compound 29 with compounds 1 and 8 suggests that when $R^1$ is a phenyl group, a substituent ortho to the succinimide improves activity against C. albicans, ii) a comparison of in compounds 31 and 8 reveals that non-hydrogen substituents at $R^5$ are better than non-hydrogen substituents at $R^6$, iii) a comparison of compounds 32 and 8 suggests that cross-species activity can be improved when $R^9$ is a substituted aryl rather than an unsubstituted aryl, iv) when $R^1$ is a cycloalkyl group, larger rings are better than smaller rings. Therefore, those spiroindolinones are candidates for combination antifungal therapy with azoles against invasive infections of not only C. albicans, but also other pathogenic fungi.

TABLE 4

| compound | Resistant Candida albicans (nM)[a] | Candida glabrata (nM)[b] | Cryptococcus neoformans (nM)[c] |
|---|---|---|---|
| 1 | 440 | 640 | >30000 |
| 8 | 490 | 1720 | 11300 |
| 11 | 750 | 236 | >30000 |
| 25 | 400 | >30000 | 192 |
| 26 | >30000 | >30000 | >30000 |
| 27 | 216 | 1010 | >30000 |
| 28 | 62 | 530 | >30000 |
| 29 | 220 | 530 | >30000 |
| 30 | >30000 | >30000 | >30000 |
| 31 | >30000 | 770 | >30000 |
| 32 | 215 | 370 | 900 |

Figure 13:
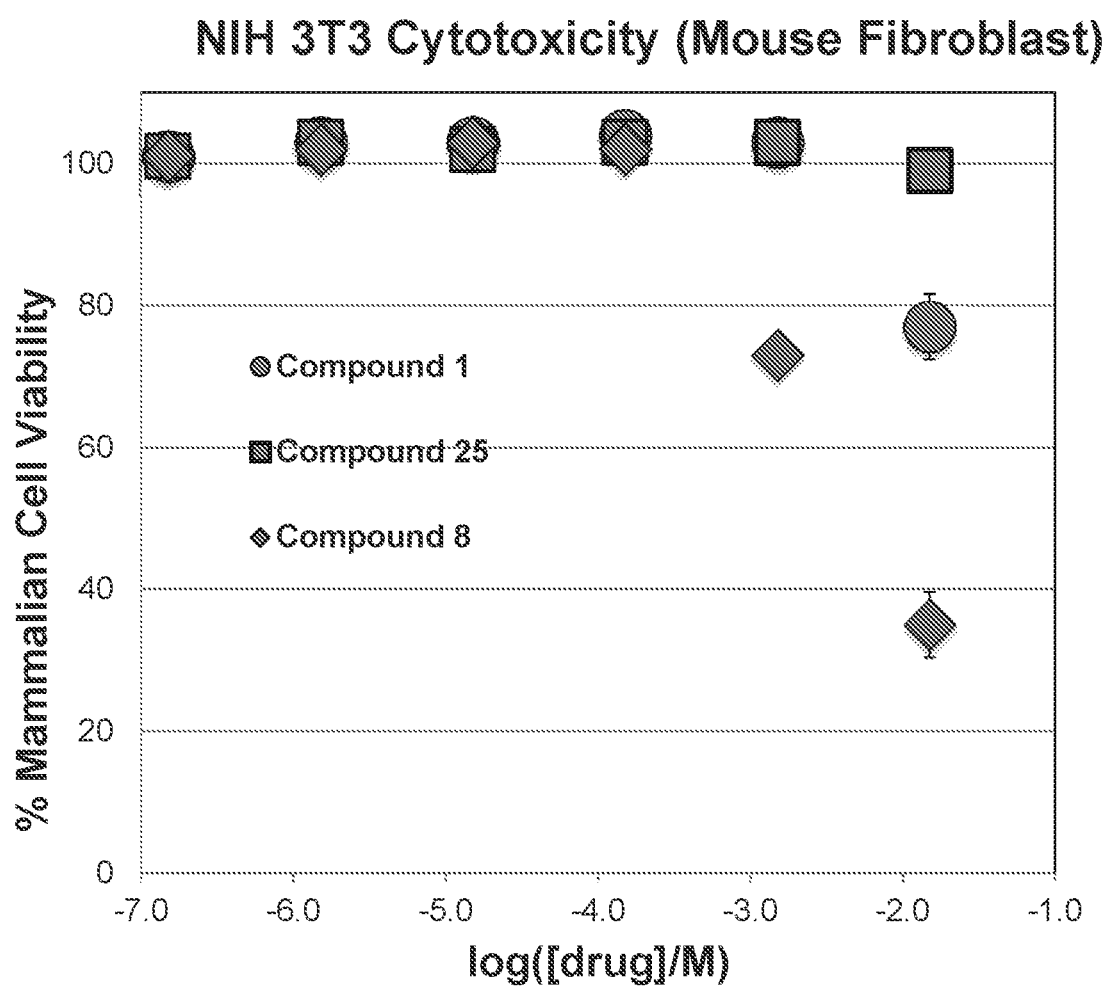
FIG. 13 provides a data plot providing the results of studies on the cytotoxicity of exemplary therapeutic small molecule analogues in accordance with the invention.

[a]C. albicans clinical isolate-45 [fluconazole] = 64 μg/mL
[b][fluconazole] = 128 μg/mL
[c][fluconazole] = 4 μg/mL Cytotoxicity of Compound 25 Against Mammalian Cells The cytotoxicity of spiroindoline Compounds 1, 8 and 25 were tested against NIH 3T3 cells at concentrations up to 1.5 mM (FIG. 13) using an LDH assay. The compounds exhibited weak to negligible cytotoxicity.

Drug-Like Parameters for Compound 25

A wide range of readily calculated properties are often used as indicators of oral bioavailability. The calculated physicochemical properties of Compound 25 were compared with typical ranges for lead-like molecules. (Monge, A., et al. Mol. Div. 2006, 10, 389-1403; and Li, J., et al. J. Comb. Chem. 2006, 8, 326-337.) Compounds 25 and 8 flag just one of the common warnings for drug lead-like properties (Table 5, below)—molecular weight. For comparison, the orally available azole posoconazole is outside the range on four of the parameters. It is widely recognized that the average molecular weight and complexity of newly approved oral drugs has been increasing with each year. (Proudfoot, J. R., Bioorg. Med. Chem. Lett. 2005, 15, 1087-1090; and Leeson, P. D. and Springthorpe, B., Nat. Rev. Drug Discovery 2007, 6, 881-890.)

TABLE 5

| Property | Range | Compound 25 | Compound 8 |
|---|---|---|---|
| milogP | −4.0 to 4.2 | 4.17 | 4.40 |
| TPSA | ≤120 Å² | 99.3 Å² | 78.5 Å² |
| molecular weight | ≤460 | 571.0 | 471.9 |
| N + O | ≥1 | 9 | 6 |
| H-bond donors | ≤5 | 1 | 2 |
| rotatable bonds | ≤10 | 4 | 3 |
| halogens | ≤7 | 1 | 1 |
| fraction sp³ | 0.15-0.80 | 0.20 | 0.22 |
| H-bond acceptors | ≤9 | 5 | 4 |

Effect of Stereochemistry on Biological Activity

Figure 14:
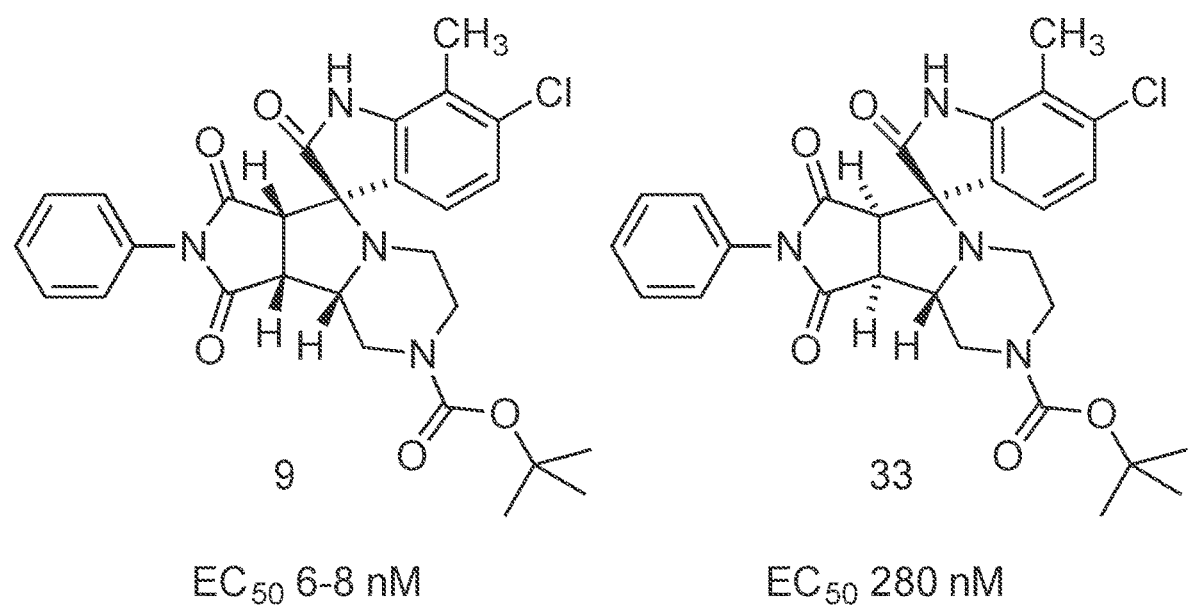
FIG. 14 compares the activity of two diastereomeric spiroindolinones exemplary therapeutic small molecule analogues in accordance with the invention.

To study the importance of relative stereochemistry as it relates to biological activity, a diastereomer of compound 9 was prepared using a known method (Ardill, H., et al. *Tetrahedron* 1990, 46, 6433-6448). When the antifungal activity of diastereomeric compound 33 was compared with that of compound 9 (FIG. 14), compound 9 (embodied in this invention) was shown to be over 35 times more potent than compound 33 with an $EC_{50}$ of 6-8 nM vs an $EC_{50}$ of 180 nM for compound 33.

SUMMARY

Analogues of a spiroindolinone that was previously reported to exhibit activity against *C. albicans* in combination with fluconazole have been developed, synthesized and tested. The relative stereochemistry of the analogues was secured through 2D NMR experiments. The three-component, one-pot [3+2] dipolar cycloaddition of isatins, amino acids, and maleimides was found to proceed through endo addition of maleimides to a syn-anti azomethine ylide in all cases except for a proline derivative. A number of the new spiroindolinones were substantially more potent against *C. albicans* than any previously reported synergistic spiroindolinone when used in combination with fluconazole. Embodiments are provided that are exquisitely potent with an $EC_{50}$ below 1 nM against a susceptible strain. Embodiments also exhibited low nanomolar activity against a number of resistant isolates of *Candida*. When tested in both susceptible and resistant strains of *C. albicans*, embodiments were shown to be true synergizers with an FIC index below 0.5. The calculable parameters associated with many embodiments of orally-available drug molecules represent promising candidate for development as antifungal synergizers.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

---

What is claimed is:

1. A compound of the formula:

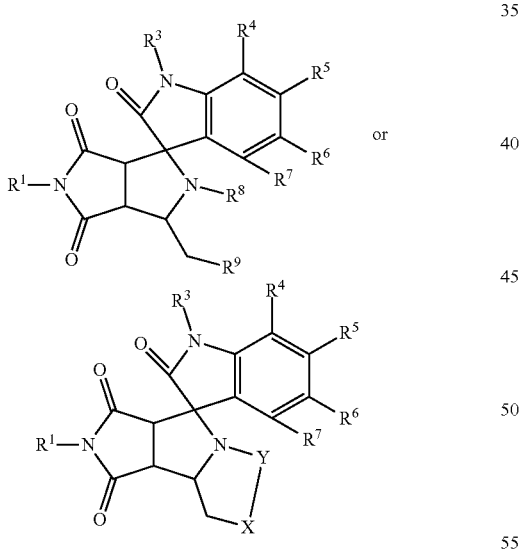

wherein:
  $R^1$ is one of the following: a substituted or unsubstituted phenyl, a substituted or unsubstituted naphthyl, a substituted or unsubstituted heteroaryl, a substituted or unsubstituted benzyl, C2-C6 alkyl, C3-C6 alkynyl, C2-C6 alkoxyalkyl, C3-C7 cycloalkyl, or C5-C7 cycloalkenyl;
  Y—X is C=C as part of an aromatic or heteroaromatic ring that is fused to the five-membered ring containing N—Y—X; or Y is $CH_2$, and X is one of the following: O, S, $NR^2$, N—Z—$R^2$, $CR^2Q$, or C=C as part of an aromatic or heteroaromatic ring that is fused to the six-membered ring containing N—Y—X; or Y is $CH_2CH_2$, or $C(O)CH_2$ and X is one of the following: O, S, $NR^2$, N—Z—$R^2$, $CR^2Q$, or C=C as part of an aromatic or heteroaromatic ring that is fused to the seven-membered ring containing N—Y—X;
  Q is one of the following: $OR^{2'}$, $SR^{2'}$, $NHR^{2'}$, $NR^{2'}R^{2''}$, $N_3$, $NO_2$, CN, or $R^2$;
  Z is one of the following: carbonyl, sulfur, an oxidized form of sulfur, or an oxidized form of phosphorus;
  $R^2$, $R^{2'}$ and $R^{2''}$ are each independently one of the following: H, an unsubstituted or substituted aryl, an unsubstituted or substituted heteroaryl, an unsubstituted or substituted benzyl, an unsubstituted or substituted phenethyl, a substituted or unsubstituted C1-C9 alkyl, a substituted or unsubstituted C3-C9 cycloalkyl, a substituted or unsubstituted C3-C9 cycloalkenyl, a substituted or unsubstituted C2-C9 alkenyl, a substituted or unsubstituted C2-C9 alkynyl, a substituted or unsubstituted C2-C9 alkoxyalkyl, a substituted or unsubstituted C1-C10 alkoxy, a substituted or unsubstituted C1-C10 acyloxy, a substituted or unsubstituted C1-C10 carbamoyl, an unsubstituted or substituted benzyloxy, a substituted or unsubstituted C4-C10 cycloalkoxy, a substituted or unsubstituted C1-C8 alkylamino, a substituted or unsubstituted C4-C7 cycloalkylamino, an unsubstituted or substituted benzylamino, or an unsubstituted or substituted arylamino;
  $R^3$ is one of the following: H, a substituted or unsubstituted benzyl, a substituted or unsubstituted C2-C6 alkyl, a substituted or unsubstituted C2-C6 alkynyl, a substituted or unsubstituted C1-C6 alkoxyalkyl, a substituted or unsubstituted C3-C7 cycloalkyl, a substituted or unsubstituted C5-C7 cycloalkenyl, an alkanesulfonyl, an arenesulfonyl, hydroxy, or a substituted or unsubstituted C1-C6 alkyloxy;

$R^4$ and $R^5$ either together form a five-membered or six-membered heteroaryl or heterocyclyl ring or are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, a substituted or unsubstituted aryl group, a substituted or unsubstituted heteroaryl group, a substituted or unsubstituted an alkanesulfonyl, a substituted or unsubstituted arenesulfonyl, a substituted or unsubstituted arenesulfinyl, cyano, nitro, a substituted or unsubstituted amino group, a carboxylic acid, a substituted or unsubstituted carboxamide, or a substituted or unsubstituted C1-C6 carboxyalkyl;

$R^6$ and $R^7$ are each independently any combination of the following: H, halogen, a substituted or unsubstituted C1-C6 alkyl, hydroxy, a substituted or unsubstituted C1-C6 alkoxy, a substituted or unsubstituted C2-C6 alkynyl, a substituted or unsubstituted C3-C7 cycloalkyl, a substituted or unsubstituted C5-C7 cycloalkenyl, a substituted or unsubstituted C2-C6 alkoxyalkyl, a substituted or unsubstituted aryl group, a substituted or unsubstituted heteroaryl group, a substituted or unsubstituted an alkanesulfonyl, a substituted or unsubstituted arenesulfonyl, a substituted or unsubstituted arenesulfinyl, cyano, nitro, a substituted or unsubstituted amino group, a carboxylic acid, a substituted or unsubstituted carboxamide, or a substituted or unsubstituted C1-C6 carboxyalkyl;

$R^8$ is H; and $R^9$ is a substituted or unsubstituted aromatic or a substituted or unsubstituted heteroaromatic;

wherein the compound is in the form of a pharmaceutically acceptable salt; and wherein the indolone arene ring, the succinimide ring, and the $CH_2$—$R^9$ group are all disposed on the same face of the central pyrrolidine ring, as shown in the following formula:

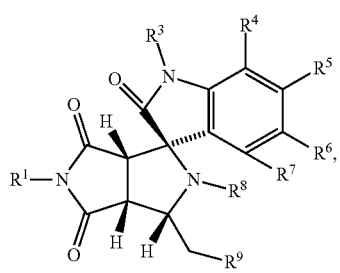

and $R^4$ is methyl.

2. The compound as described in claim 1, wherein the indolone arene ring, the succinimide ring, and the ring comprised of N—Y—X are all disposed on the same face of the central spiropyrrolidine ring, as shown in the following formula:

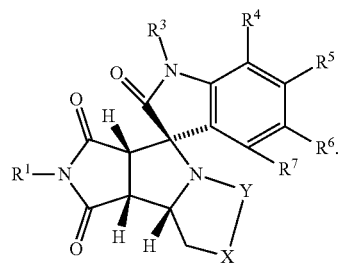

3. The compound, as described in claim 1, wherein Y is $CH_2$, X is CHQ and when Q is not H but instead one of the following: hydroxy, a substituted or unsubstituted C1-C10 alkoxy, a substituted or unsubstituted C4-C6 cycloalkoxy, an optionally substituted benzyloxy, a substituted or unsubstituted C1-C10 acyloxy, cyano, a substituted or unsubstituted C1-C10 alkylaminocarbonyl, an optionally substituted aryl, an optionally substituted heteroaryl, an optionally substituted benzyl, an optionally substituted phenethyl, a substituted or unsubstituted C1-C9 alkyl, a substituted or unsubstituted C3-C9 cycloalkyl, a substituted or unsubstituted C5-C6 cycloalkenyl, a substituted or unsubstituted C2-C9 alkenyl, a substituted or unsubstituted C2-C9 alkynyl, a substituted or unsubstituted C2-C9 alkoxyalkyl, a substituted or unsubstituted C1-C10 carbamoyl, a substituted or unsubstituted C1-C8 alkylamino, amino, a substituted or unsubstituted C4-C7 cycloalkylamino, an optionally substituted benzylamino, and an optionally substituted arylamino.

4. The compound, as described in claim 1, wherein the compound is selected from one of the following combinations of functional groups:
where Y is $CH_2CH_2$, and Z is one of the following: carbonyl, sulfur, an oxidized form of sulfur, an oxidized form of phosphorus;
where Y is $CH_2CH_2$, and Z is CO;
where Y is $CH_2CH_2$, Z is CO, and $R^3$ is H;
where Y is $CH_2CH_2$, Z is CO, and each of $R^3$, $R^6$, and $R^7$ are H;
where Y is $CH_2CH_2$, Z is CO, each of $R^3$, $R^6$, and $R^7$ are H, $R^4$ is $CH_3$, and $R^5$ is either Cl or $CH_3$;
where Y is $CH_2CH_2$, Z is CO, each of $R^3$, $R^6$, and $R^7$ are H, and $R^1$ is a substituted or unsubstituted heteroaryl;
where Y is $CH_2CH_2$, Z is CO, each of $R^3$, $R^6$, and $R^7$ are H, and $R^2$ is either t-butoxy or benzyloxy; and
where Y is $CH_2CH_2$, Z is CO, each of $R^3$, $R^6$, and $R^7$ are H, $R^4$ is $CH_3$, $R^5$ is Cl, $R^1$ is phenyl, and $R^2$ is benzyloxy.

5. The compound, as described in claim 1, wherein the compound is selected from one of the following combinations of functional groups:
where $R^4$ is methyl and each of $R^3$, $R^6$, $R^7$ and $R^8$ are H;
where $R^1$ is a substituted or unsubstituted phenyl, $R^3$ is H, $R^4$ is methyl and $R^9$ is a substituted or unsubstituted aryl: phenyl, naphthyl, imidazole, pyrazole, furan, oxazole, isoxazole, isothiazole, thiophene, thiazole, triazole, furazan, oxadiazole, pyridine, pyrazine, pyrimidine, quinoline, isoquinoline, benzothiazole, benzimidazole, benzothiophene, or benzotriazole;
where $R^1$ is a substituted or unsubstituted phenyl, $R^3$ is H, and $R^4$ is methyl;
where $R^1$ is a substituted or unsubstituted phenyl, $R^3$, $R^6$, and $R^7$ are H, $R^4$ is methyl, $R^5$ is Cl or methyl, and $R^9$ is a substituted or unsubstituted aryl: phenyl, naphthyl, imidazole, pyrazole, furan, oxazole, isoxazole, isothiazole, thiophene, thiazole, triazole, furazan, oxadiazole, pyridine, pyrazine, pyrimidine, quinoline, isoquinoline, benzothiazole, benzimidazole, benzothiophene, or benzotriazole;

where $R^1$ is a substituted or unsubstituted phenyl, $R^3$, $R^6$, and $R^7$ are H, $R^4$ is methyl, and $R^5$ is Cl or methyl;

wherein the compound is selected from one of the following combinations of functional groups: $R^3$, $R^6$, and $R^7$ are H, $R^4$ is methyl, $R^5$ is Cl, $R^9$ is a substituted or unsubstituted phenyl, and $R^1$ is C5-C6 alkyl, C3-C7 cycloalkyl, C3-C6 alkynyl, or C3-C6 alkoxylalkyl;

wherein the compound is selected from one of the following combinations of functional groups: $R^1$ is a phenyl, $R^3$, $R^6$, $R^7$, and $R^8$ are H, $R^4$ is methyl, $R^5$ is Cl, and $R^9$ phenyl; and wherein the compound is selected from one of the following combinations of functional groups: $R^1$ is a cycloheptyl, $R^3$, $R^6$, $R^7$, and $R^8$ are H, $R^4$ is methyl, $R^5$ is Cl, and $R^9$ phenyl.

6. The compound, as described in claim 1, wherein the compound is an enantiomer or a mixtures of enantiomers.

7. The compound, as described in claim 1, wherein the compound inhibits Cdr1.

8. A medicament comprising a pharmaceutical formulation containing a therapeutically effective amount of one or more spiroindolinone small molecule compounds selected from claim 1.

9. The medicament of claim 8, wherein the medicament is an active compound against eukaryotic cells.

10. The medicament of claim 8, wherein the compound inhibits Cdr1.

11. The medicament of claim 8, wherein the medicament is administered against a pathogenic microorganism in conjunction with an antimicrobial drug, or a pathogenic fungi in conjunction with an antifungal drug.

12. The medicament of claim 11, wherein the antifungal drug is selected from the group consisting of azoles; albaconazole, efinaconazole, itraconazole, fluconazole, terconazole, voriconazole, posaconazole, epoxiconazole, isavuconazole, ravuconazole, phosravuconazole; and imidazoles: clotrimazole, ketoconazole, bifonazole, butoconazole, econazole, fenticonazole, isoconazole, luliconazole, miconazole, omoconazole, oxiconazole, sertaconazole, sulconazole, tioconazole; thiazoles: abafungin; naphthylmethylamines: butenafine, naftifine, terbinafine; and morpholines: amorolfine, fenpropimorph, dodemorph, tridemorph; flucytosine; tolnaftate; griseofulvin; cicloprimox; FK506; and cyclosporine.

13. The medicament of claim 11, wherein the pathogenic fungi is a strain of *Candida albicans, Candida glabrata*, or *Cryptococcus neoformans*.

14. A method of treating a fungal infection in a patient comprising:
diagnosing a patient having a fungal infection susceptible to treatment at least in part by eukaryotic cell regulation; and
administering a therapeutically effective amount of one or more spiroindolinone small molecule compounds selected from claim 1.

15. The method of claim 14, wherein the small molecule compounds are one or more spiroindolinone small molecule compounds active against eukaryotic cells.

16. The method of claim 14, wherein the small molecule compounds are administered against a pathogenic microorganism in conjunction with an antimicrobial drug.

17. The method of claim 16, wherein the antifungal drug is selected from the group consisting of azoles; albaconazole, efinaconazole, itraconazole, fluconazole, terconazole, voriconazole, posaconazole, epoxiconazole, isavuconazole, ravuconazole, phosravuconazole; and imidazoles: clotrimazole, ketoconazole, bifonazole, butoconazole, econazole, fenticonazole, isoconazole, luliconazole, miconazole, omoconazole, oxiconazole, sertaconazole, sulconazole, tioconazole; thiazoles: abafungin; naphthylmethylamines: butenafine, naftifine, terbinafine; and morpholines: amorolfine, fenpropimorph, dodemorph, tridemorph; flucytosine; tolnaftate; griseofulvin; cicloprimox; FK506; and cyclosporine.

18. The method of claim 16, wherein the pathogenic microorganism is a strain of *Candida*.

19. The method of claim 14, wherein the one or more compounds inhibit Cdr1.

20. The compound as described in claim 1, where Y is $CH_2CH_2$, Z is CO, each of $R^3$, $R^6$, and $R^7$ are H, $R^4$ is $CH_3$, $R^5$ is Cl, $R^1$ is phenyl, and $R^2$ is benzyloxy.

21. The compound as described in claim 1, wherein $R^1$ is a phenyl, $R^3$, $R^6$, $R^7$, and Fe are H, $R^4$ is methyl, $R^5$ is Cl, and $R^9$ phenyl.

* * * * *

SEQUENCE LISTING

```
<160> NUMBER OF SEQ ID NOS: 5

<210> SEQ ID NO 1
<211> LENGTH: 52
<212> TYPE: DNA
<213> ORGANISM: Artificial Sequence
<220> FEATURE:
<223> OTHER INFORMATION: Synthetic Oligo

<400> SEQUENCE: 1
caagcagaag acggcatacg agctcttccg atctgatgtc cacgaggtct ct          52

<210> SEQ ID NO 2
<211> LENGTH: 83
<212> TYPE: DNA
<213> ORGANISM: Artificial Sequence
<220> FEATURE:
<223> OTHER INFORMATION: Synthetic Oligo
<220> FEATURE:
<221> NAME/KEY: variation
<222> LOCATION: (59)..(65)
<223> OTHER INFORMATION: "NNNNNNNN" = varibale 7-mer index tag to
      barcode sample
<220> FEATURE:
<221> NAME/KEY: misc_feature
<222> LOCATION: (59)..(65)
<223> OTHER INFORMATION: n is a, c, g, or t

<400> SEQUENCE: 2
aatgatacgg cgaccaccga gatctacact ctttccctac acgacgctct tccgatctnn    60
nnnnngtcga cctgcagcgt acg                                            83

<210> SEQ ID NO 3
<211> LENGTH: 53
<212> TYPE: DNA
<213> ORGANISM: Artificial Sequence
<220> FEATURE:
<223> OTHER INFORMATION: Synthetic Oligo

<400> SEQUENCE: 3
caagcagaag acggcatacg agctcttccg atctcgagct cgaattcatc gat           53
```

```
<210> SEQ ID NO 4
<211> LENGTH: 82
<212> TYPE: DNA
<213> ORGANISM: Artificial Sequence
<220> FEATURE:
<223> OTHER INFORMATION: Synthetic Oligo
<220> FEATURE:
<221> NAME/KEY: variation
<222> LOCATION: (59)..(65)
<223> OTHER INFORMATION: "NNNNNNNN" = varibale 7-mer index tag to
      barcode sample
<220> FEATURE:
<221> NAME/KEY: misc_feature
<222> LOCATION: (59)..(65)
<223> OTHER INFORMATION: n is a, c, g, or t

<400> SEQUENCE: 4
aatgatacgg cgaccaccga gatctacact ctttccctac acgacgctct tccgatctnn     60
nnnnncggtg tcggtctcgt ag                                              82

<210> SEQ ID NO 5
<211> LENGTH: 33
<212> TYPE: DNA
<213> ORGANISM: Artificial Sequence
<220> FEATURE:
<223> OTHER INFORMATION: Synthetic Oligo

<400> SEQUENCE: 5
acactctttc cctacacgac gctcttccga tct                                  33
```